United States Patent
Kishkovich et al.

(10) Patent No.: US 7,092,077 B2
(45) Date of Patent: Aug. 15, 2006

(54) SYSTEM AND METHOD FOR MONITORING CONTAMINATION

(75) Inventors: Oleg P. Kishkovich, Greenville, RI (US); Anatoly Grayfer, Newton, MA (US); William M. Goodwin, Medway, MA (US); Devon Kinkead, Holliston, MA (US)

(73) Assignee: Entegris, Inc., Chaska, MN (US)

( * ) Notice: Subject to any disclaimer, the term of this patent is extended or adjusted under 35 U.S.C. 154(b) by 0 days.

(21) Appl. No.: 10/662,892

(22) Filed: Sep. 15, 2003

(65) Prior Publication Data

US 2004/0166679 A1 Aug. 26, 2004

Related U.S. Application Data

(63) Continuation-in-part of application No. 10/395,834, filed on Mar. 24, 2003, which is a continuation-in-part of application No. 10/253,401, filed on Sep. 24, 2002, now Pat. No. 6,759,254, which is a continuation-in-part of application No. 09/961,802, filed on Sep. 24, 2001, now Pat. No. 6,620,630.

(51) Int. Cl.
*G01N 1/00* (2006.01)
*H01L 21/66* (2006.01)

(52) U.S. Cl. .......................... 356/36; 438/14

(58) Field of Classification Search .............. 257/66, 257/629, 687, 700, 713, 78–80, 99; 250/306, 250/440.11, 441.11, 442.11, 443.11, 336.1, 250/338.5, 305, 338, 339, 343, 345, 373, 250/504, 339.01, 370.01, 374; 438/7, 14, 438/16, 102, 115, 101, 166, 22, 365, 482, 438/509, 513, 540, 57, 597, 603, 618, 680, 438/635, 783–784, 795; 356/246, 432, 437, 356/499

See application file for complete search history.

(56) References Cited

U.S. PATENT DOCUMENTS

| | | | |
|---|---|---|---|
| 3,834,122 A | 9/1974 | Allison et al. | 55/33 |
| 4,170,901 A | 10/1979 | Conkle et al. | 73/421.5 |
| 4,429,736 A | 2/1984 | Turner | 165/61 |
| 4,474,051 A | 10/1984 | Fukuda et al. | 73/19 |
| 4,645,516 A | 2/1987 | Doshi | 55/16 |
| 4,998,433 A | 3/1991 | Stumpf et al. | 73/25.01 |
| 5,054,046 A | 10/1991 | Shoulders | 378/119 |
| 5,108,178 A * | 4/1992 | Oishi et al. | 356/312 |
| 5,122,355 A | 6/1992 | Prasad et al. | 423/351 |

(Continued)

FOREIGN PATENT DOCUMENTS

DE 198 41 814 3/2000

(Continued)

OTHER PUBLICATIONS

Ogawa & Company, company website, www.ogawausa.com, About Ogawa & Company, Jul. 24, 2003.

(Continued)

*Primary Examiner*—Michael Lebentritt
*Assistant Examiner*—Andre' Stevenson
(74) *Attorney, Agent, or Firm*—Weingarten, Schurgin, Gagnebin & Lebovici LLP

(57) ABSTRACT

The present invention provides passive sampling systems and methods for monitoring contaminants in a semiconductor processing system. In one embodiment, that passive sampling system comprises a collection device in fluid communication with a sample line that provides a flow of gas from a semiconductor processing system. The collection device is configured to sample by diffusion one or more contaminants in the flow of gas.

16 Claims, 42 Drawing Sheets

U.S. PATENT DOCUMENTS

| | | | |
|---|---|---|---|
| 5,153,901 A | 10/1992 | Shoulders | 378/119 |
| 5,168,068 A | 12/1992 | Yanagisawa et al. | 436/134 |
| 5,274,434 A | 12/1993 | Morioka et al. | 356/237 |
| 5,481,110 A | 1/1996 | Krishnaswamy et al. | 250/288 |
| 5,574,230 A | 11/1996 | Baugh | 73/863.23 |
| 5,676,760 A * | 10/1997 | Aoki et al. | 134/1.3 |
| 5,725,634 A | 3/1998 | Takasuga et al. | 95/45 |
| 5,773,713 A | 6/1998 | Barber et al. | 73/61.41 |
| 5,841,022 A | 11/1998 | Hase | 73/23.22 |
| 5,856,198 A | 1/1999 | Joffe et al. | 436/100 |
| 5,898,114 A | 4/1999 | Basch et al. | 73/863.23 |
| 5,935,302 A | 8/1999 | Ju et al. | 96/4 |
| 5,983,704 A | 11/1999 | Park et al. | 73/28.01 |
| 6,009,739 A | 1/2000 | Fujiwara et al. | 73/1.02 |
| 6,096,267 A | 8/2000 | Kishkovich et al. | 422/52 |
| 6,119,532 A | 9/2000 | Park et al. | 73/864.34 |
| 6,139,801 A | 10/2000 | Kawachi et al. | 422/88 |
| 6,168,948 B1 | 1/2001 | Anderson et al. | 435/287.2 |
| 6,239,038 B1 | 5/2001 | Wen | 438/745 |
| 6,287,023 B1 | 9/2001 | Yaegashi et al. | 396/565 |
| 6,290,779 B1 | 9/2001 | Saleh et al. | 134/2 |
| 6,295,864 B1 | 10/2001 | You et al. | 73/53.01 |
| 6,310,356 B1 | 10/2001 | Yuhara et al. | 250/574 |
| 6,467,333 B1 | 10/2002 | Lewis et al. | 73/31.05 |
| 6,470,760 B1 | 10/2002 | Shinozaki et al. | 73/863.33 |
| 6,491,885 B1 * | 12/2002 | Tokunaga et al. | 423/212 |
| 6,497,136 B1 | 12/2002 | Satou | 73/23.22 |
| 6,620,630 B1 | 9/2003 | Kishkovich et al. | 438/7 |
| 2002/0121148 A1 | 9/2002 | Shinozaki t al. | 73/863.33 |

FOREIGN PATENT DOCUMENTS

| | | |
|---|---|---|
| DE | 198 47 697 | 4/2000 |
| EP | 0 298 000 | 1/1989 |
| EP | 0 692 297 | 1/1996 |
| EP | 1 166 845 | 6/2001 |
| EP | 1 190 945 | 3/2002 |
| JP | 11-20034 | 1/1999 |
| JP | 11-57346 | 3/1999 |
| JP | 11-64316 | 5/1999 |

OTHER PUBLICATIONS

Ogawa & Company, company website, www.ogawausa.com, Passive Sampler, Jul. 24, 2003.

Dallas, et al., "Characterization and Control of Organic Airborne Contamination in Lithographic Processing", Paper presented at SPIE Microlithography 2002.

* cited by examiner

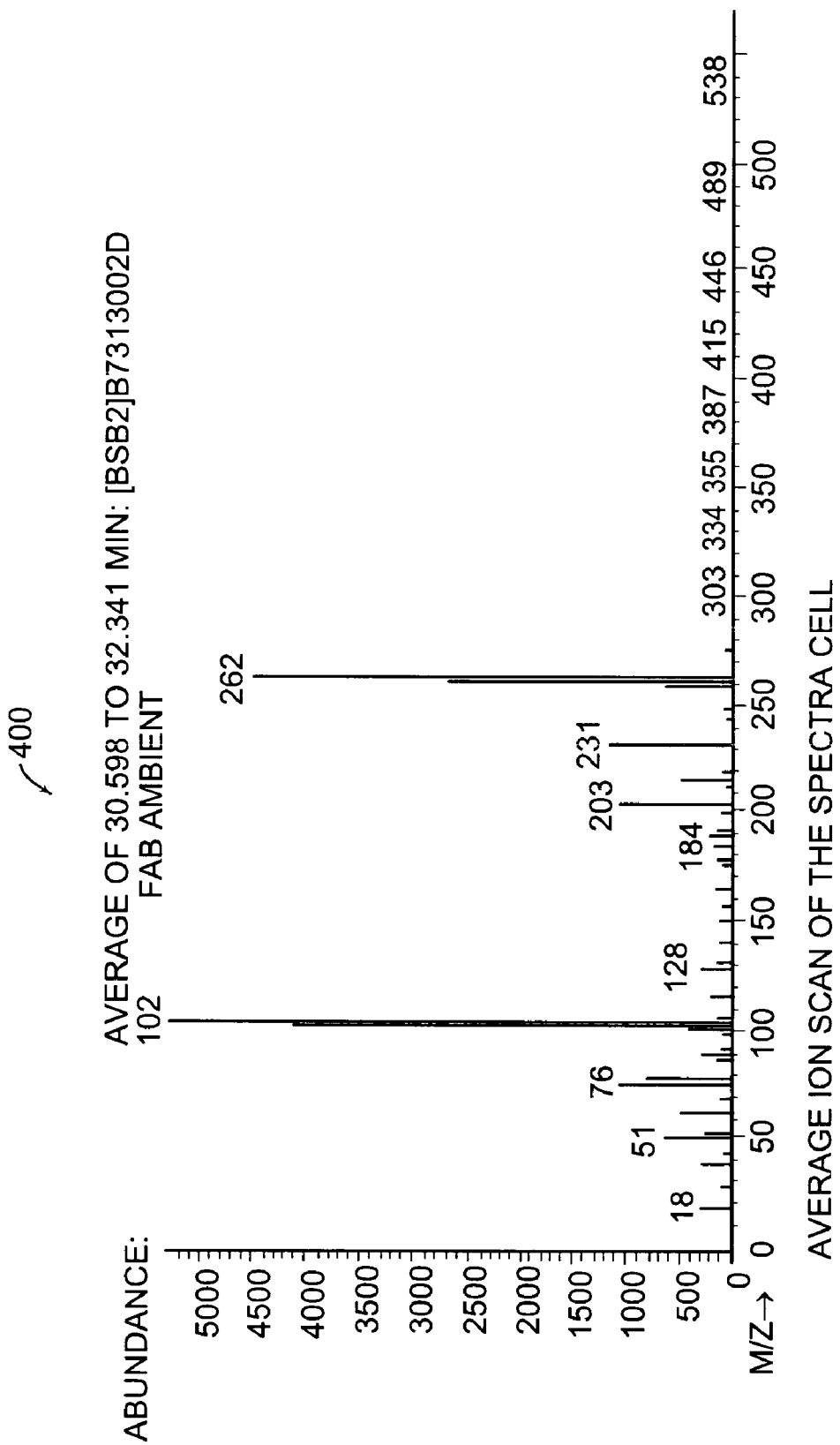

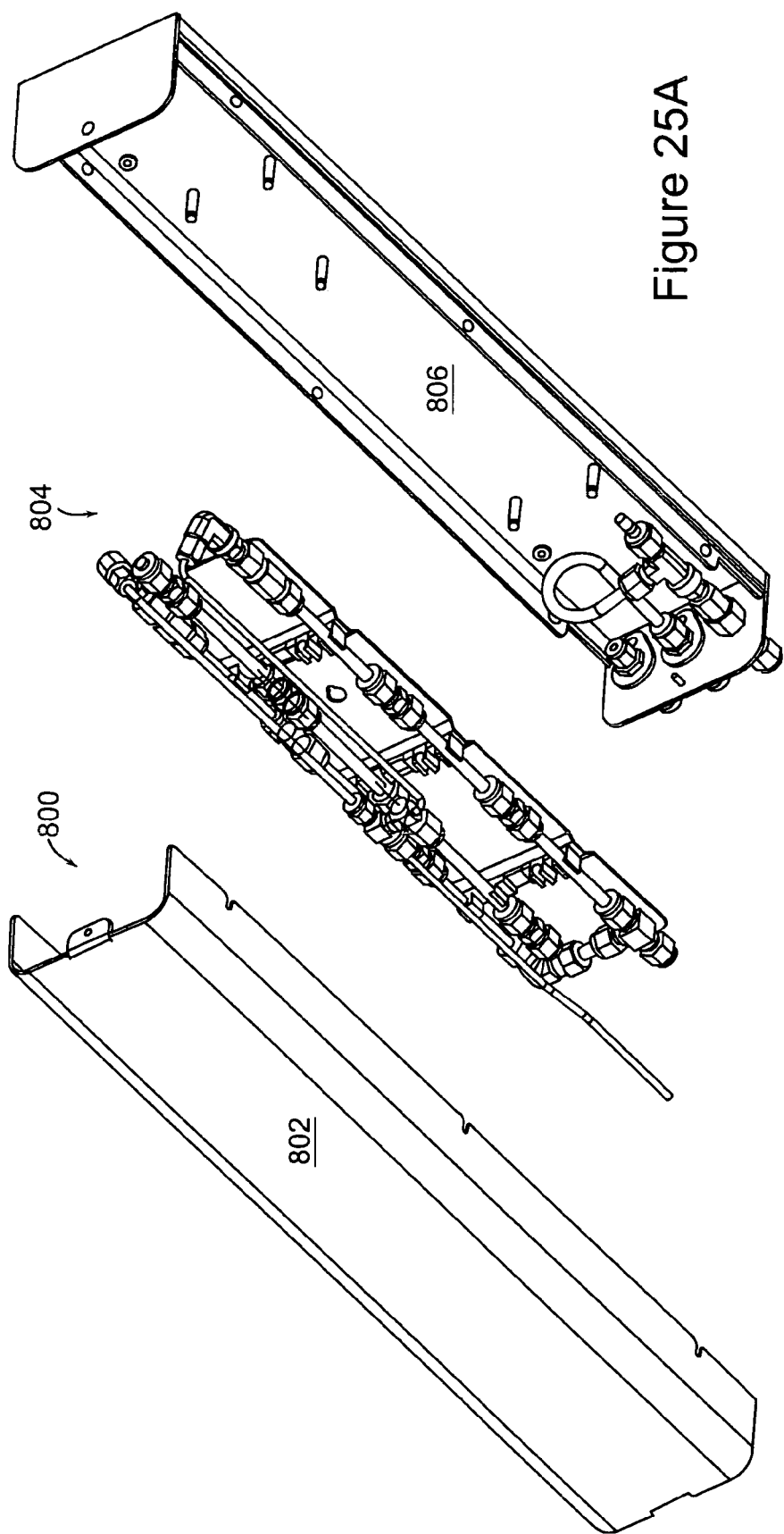

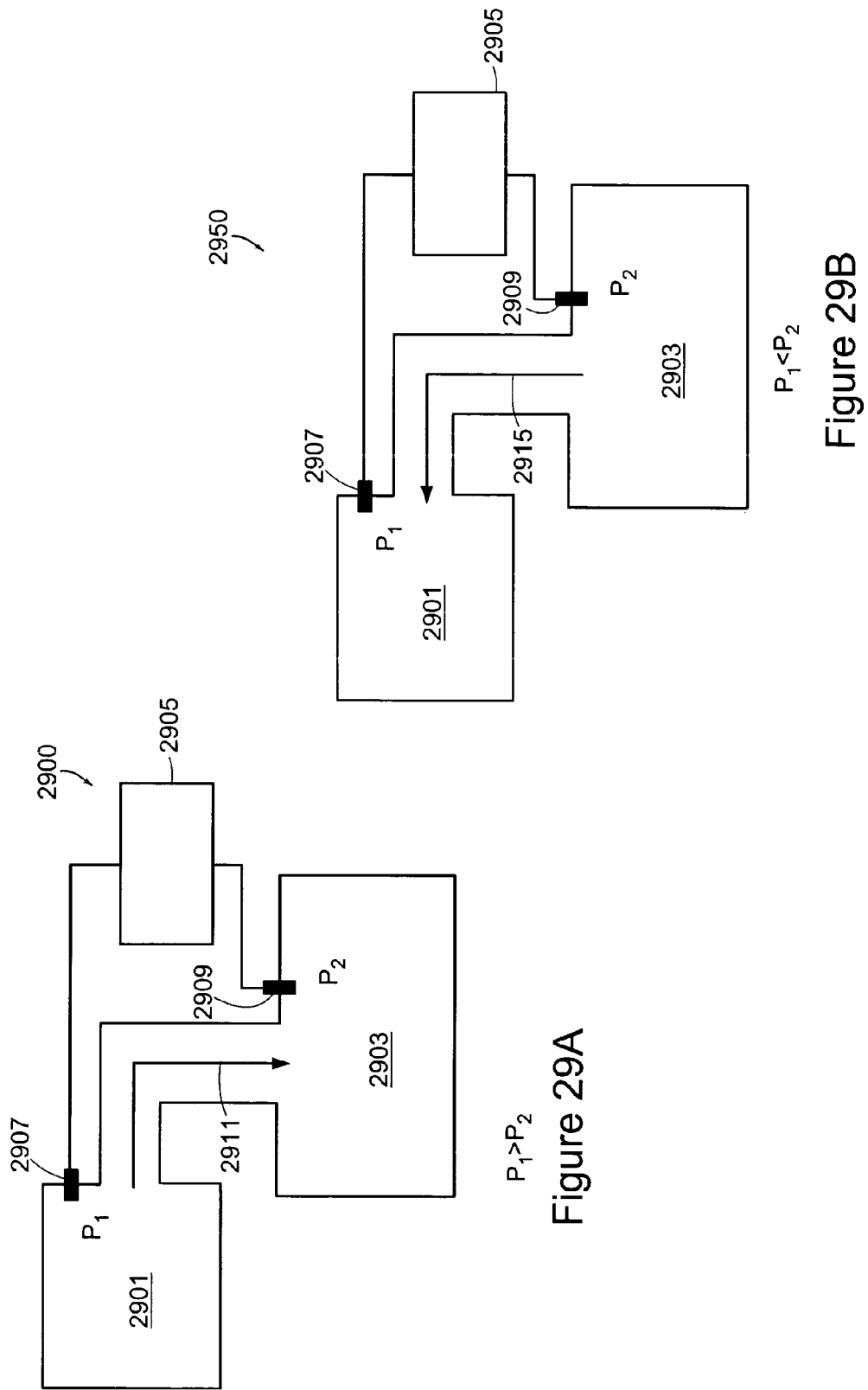

COVER REMOVED

SYSTEM AND METHOD FOR MONITORING CONTAMINATION

CROSS REFERENCES TO RELATED APPLICATIONS

The present application is a continuation-in-part of U.S. patent application Ser. No. 10/395,834 filed Mar. 24, 2003, which is continuation-in-part of U.S. patent application Ser. No. 10/253,401, filed Sep. 24, 2002 now U.S. Pat. No. 6,759,254, which is a continuation-in-part of U.S. patent application Ser. No. 09/961,802, filed Sep. 24, 2001 now U.S. Pat. No. 6,620,630. The entire contents of the above applications are incorporated herein by reference.

BACKGROUND OF THE INVENTION

Semiconductor manufacturers continue to measure and control the level of contamination in the processing environment, especially during the critical steps of the photolithography processes. The typical means of determining the quality and quantity of contamination in gas samples in cleanroom manufacturing environments involves sampling air and purge gases, such as, for example, filtered and unfiltered air, clean dry air, and nitrogen, with sampling tubes or traps, typically containing adsorptive medium such as, the polymer Tenax®. This sampling process is followed by analysis using thermal desorption, gas chromatography and mass spectrometry (TD/GC/MS). The combination of TD/GC/MS provides identification of sample components and a determination of the concentration of these components. The most abundant contaminants in these manufacturing environments are low molecular weight components such as acetone and isopropyl alcohol. The current sampling time for existing traps typically varies between 0.5 and 6 hours with total accumulated sample volumes ranging typically between 20 and 50 liters.

Further, in applications that are directed to the manufacturing of or use of optical elements such as, for example, photolithography, the detection and quantification of compounds having a higher molecular weight such as, for example, siloxanes is of primary concern. These compounds having a higher molecular weight are, however, typically in much lower concentrations as compared with the low molecular weight species. Further, the compounds having a high molecular weight can also be defined as condensable compounds with a boiling point typically greater than approximately 150° C. The current methods for determining contamination have the limitation of the sample volume being based on the total trap capacity of the lighter or lower molecular weight components, for example, compounds having typically less than six carbon atoms. As the heavier components are usually present at much lower concentrations, the collection of a significant mass of these higher molecular weight species is limited.

In addition, polluting or contaminating substances may adhere onto the optical elements and reduce the transmission of light. Currently airborne contamination is addressed in cleanroom environments with little regard for contaminants that may be adsorbed onto the surfaces of optical elements. The adsorbed contamination reduces the transmission of light through the optical elements and system.

Thus, contamination of optical systems is emerging as a significant risk to photolithography and other semiconductor manufacturing processes as shorter wavelengths of the electromagnetic spectrum are exploited. However, molecular films on optical surfaces physically absorb and scatter incoming light. Scattered or absorbed light in photolithography optical surfaces causes distortion of the spherical quality of wavefronts. When the information contained in the spherical wavefront is distorted, the resulting image is also misformed or abberated. Image distortions, or in the case of photolithography, the inability to accurately reproduce the circuit pattern on the reticle, cause a loss of critical dimension control and process yield.

Typically, filter systems are used to remove molecular contamination in semiconductor processing environments. Systems are in place to measure the performance of such filter systems. However, typical monitoring of filter performance includes measurement of filter breakthrough either by process failure or by detection of the target filtered gas at the discharge of the filter system. However, these measurement means detect breakthrough after it has occurred.

A need still exists for determining, accurately and efficiently, the presence and quantity of contaminants that can alter and degrade the optical systems in semiconductor processing instruments. There further remains a need to monitor the performance of gas phase filter systems prior to a breakthrough failure.

SUMMARY OF THE INVENTION

The preferred embodiments of the system of the present invention provide an accurate and efficient system of determining and/or controlling the quality and/or quantity of contamination within a gas sample which can reduce the performance of optical elements used in semiconductor processing instruments, such as, for example, within the light path of a deep ultraviolet photolithography exposure tool. In a preferred embodiment of the present invention, the contamination may be gaseous as well as contamination adsorbed onto optical surfaces. Optical performance can be evaluated without limitation as the level of transmitted or reflected light through an optical system. The embodiments of the system and method of the present invention are predicated on the recognition that compounds having both high and low molecular weights can contribute to the contamination of optical systems but can operate at different rates. As such, the contaminants that negatively impact the performance of optical elements can be described in terms of different orders, such as, for example, first, second and third order effects.

First and second order contaminating effects have a greater impact on contamination of optical systems than third or fourth order contaminants. The first order contaminants may comprise high molecular weight organics such as, for example, $C_6$ siloxanes and $C_6$ iodates with an inorganic component which is not volatilized through combination with oxygen. Second order contaminants may comprise high molecular weight organics, such as, for example, compounds including carbon atoms within the range of approximately six to thirty carbon atoms ($C_6$–$C_{30}$). Third order effects can arise due to the contaminating effects of organics such as $C_3$–$C_6$ that have approximately three to six carbon atoms. Fourth order contaminants include organics such as, for example, methane, that have approximately one to five carbon atoms. In many applications, the first and second order contamination can have a much lower concentration than the third and/or fourth order contamination, yet have a significantly greater effect on the operation of the system.

A preferred embodiment in accordance with the present invention of a method for detecting and monitoring, and preferably removing contamination in a semiconductor processing system includes delivering a gas sample from the processing system to a collection device. The method further includes collecting contamination which comprises refractory compounds, and high and low molecular weight compounds, from the gas in the collection device by sampling the gas for a duration exceeding the saturation capacity of the collection device for high molecular weight compounds. The compounds having a high molecular weight are condensable with a boiling point typically greater than approximately 150° C.

A preferred embodiment of the system and method of the present invention for determining contamination includes the detection of refractory compounds such as, for example, siloxanes, silanes and iodates, and high molecular weight organics. The preferred embodiment includes the removal of refractory compounds, high molecular weight organics and low molecular weight organics, all of which contribute to the contamination of optical systems, but which can operate at different contamination rates.

The system of the present invention for determining contamination can use different types of sample collecting media. In a preferred embodiment, the sample collecting media can emulate the environment of the optical surfaces of interest such as, for example, the absorptive or reactive properties of the optical surfaces. A measure of contamination adsorbed onto optical surfaces enables the minimization and preferably the removal of the contaminants. In another preferred embodiment, a polymer that has a high capacity for absorbing the compounds with a high boiling point is used in a collection device such as, for example, Tenax® a polymer based on 2–6 diphenyl p-phenylene. The operation of the system in accordance with a preferred embodiment of the present invention includes quantitatively measuring the concentration of both low and high boiling point compounds in the same sample wherein the collection device has been driven beyond the breakthrough volume or saturation capacity of the collection media to capture the low molecular weight compounds. The breakthrough volume of the collection device is defined in a preferred embodiment as the quantity of gas needed to go beyond the adsorption capacity of the device.

In accordance with a preferred embodiment of the present invention, the method for detecting contamination includes a sampling time extended by, for example, a number of hours, days or weeks to enable collection of an appropriate mass of contaminants which are present in relatively low concentration. In a preferred embodiment, the sampling time is typically beyond the breakthrough capacity of the collection device for low molecular weight components, is at least six hours long and preferably within a range of six to twenty-four hours for a sampling tube system. The extended time allows for the collection of higher masses of refractory compounds and higher molecular weight compounds that may interfere with the performance of optical components even more than low molecular weight compounds. The higher molecular weight compounds include, but are not limited to, for example, siloxanes and silanes.

In accordance with another preferred embodiment of the present invention, a semiconductor processing instrument, for example, a photolithography cluster, includes a filtering system to remove contaminants. The filtering system includes a selective membrane to filter organic compounds from a gas stream.

A preferred embodiment includes a method for monitoring the performance of a filter positioned in an airstream in a semiconductor processing system. The method includes sampling the airstream at a location upstream of the filter to detect the molecular contaminants present in the airstream, identifying a target species in the contaminants upstream of the filter, selecting a non-polluting species of a contaminant having a concentration greater than a concentration of the target species, measuring the non-polluting species in the airstream at a plurality of locations, and determining the performance of the filter with respect to the target species from measurements of the non-polluting species. The plurality of locations includes, but is not limited to, a location downstream of the filter and at a location within the filter. Further, the method for monitoring includes generating a numerical representation of a chromatogram of the airstream sampled at a location upstream of the filter. The method for monitoring includes the non-polluting species having a molecular weight that is lower than that of the target species. A correlation is established between the low and high molecular weight compounds. In addition, in the method for monitoring, the step of sampling includes collecting refractory compounds, high molecular weight compounds and low molecular weight compounds. The filter comprises absorptive material.

A preferred embodiment includes a system for determining and monitoring contamination in a photolithography instrument, having at least one collection device in fluid communication with a gas flow extending through an optical system of the tool, the collection device having a material analogous to optical elements, and a light source providing high energy light to the collection device such that at least one contaminant in the gas flow reacts with the light to create a deposition layer on the material. Further, the system includes at least one photodetector coupled to the collection device to detect the presence of the deposition layer on the material by monitoring either the spectral or transmission differences. The material in the system comprises glass spheres having predetermined surface properties for adsorption of contaminants. The material is at least one of glass and coated glass material. The contamination includes at least one of refractory compounds, high molecular weight compounds and low molecular weight compounds.

In accordance with another aspect of the present invention, an apparatus for determining contamination in a semiconductor processing system includes a filter system having a plurality of filter traps for collecting contaminants from a gas stream for a duration, and an interface module coupled to the filter system in fluid communication with a gas flow extending through the processing system and directing a portion of the gas flow into and out of the filter system.

The contaminants include at least one of refractory compounds, high molecular weight compounds and low molecular weight compounds. A vacuum source can be coupled to the filter system to increase a pressure gradient across the filter traps. The filter traps can have a permeable membrane that filter contaminants such as at least one of a refractory compound, a high molecular weight compound and a low molecular weight compound from the gas flow.

In preferred embodiments, the interface module further comprises a pressure regulation device, a controller, electronically controlled valves to impose a duty cycle for sampling, a timer device to determine a sampling duration and a cooling device such as a thermoelectric cooling device. Further, the filter traps have an absorptive material such as a polymer, for example, Tenax®.

The foregoing and other features and advantages of the system and method for determining and controlling contamination will be apparent from the following more particular description of preferred embodiments of the system and method as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

Preferred embodiments of the present invention are described with reference to the following drawings, wherein:

FIGS. 12A–12C are graphical illustrations of chromatograms of a gas sample including an average ion scan of the spectra end (FIG. 12C) in accordance with a preferred embodiment of the present invention;

FIGS. 25A–25C illustrate schematic diagrams of a device that functions as a concentrator in a filter system in accordance with a preferred embodiment of the present invention;

FIGS. 29A–29B are schematic diagrams illustrating one embodiment of a system for detecting airstream backflow in a semiconductor processing system in accordance with a preferred embodiment of the present invention;

DETAILED DESCRIPTION OF THE INVENTION

Figure 1:
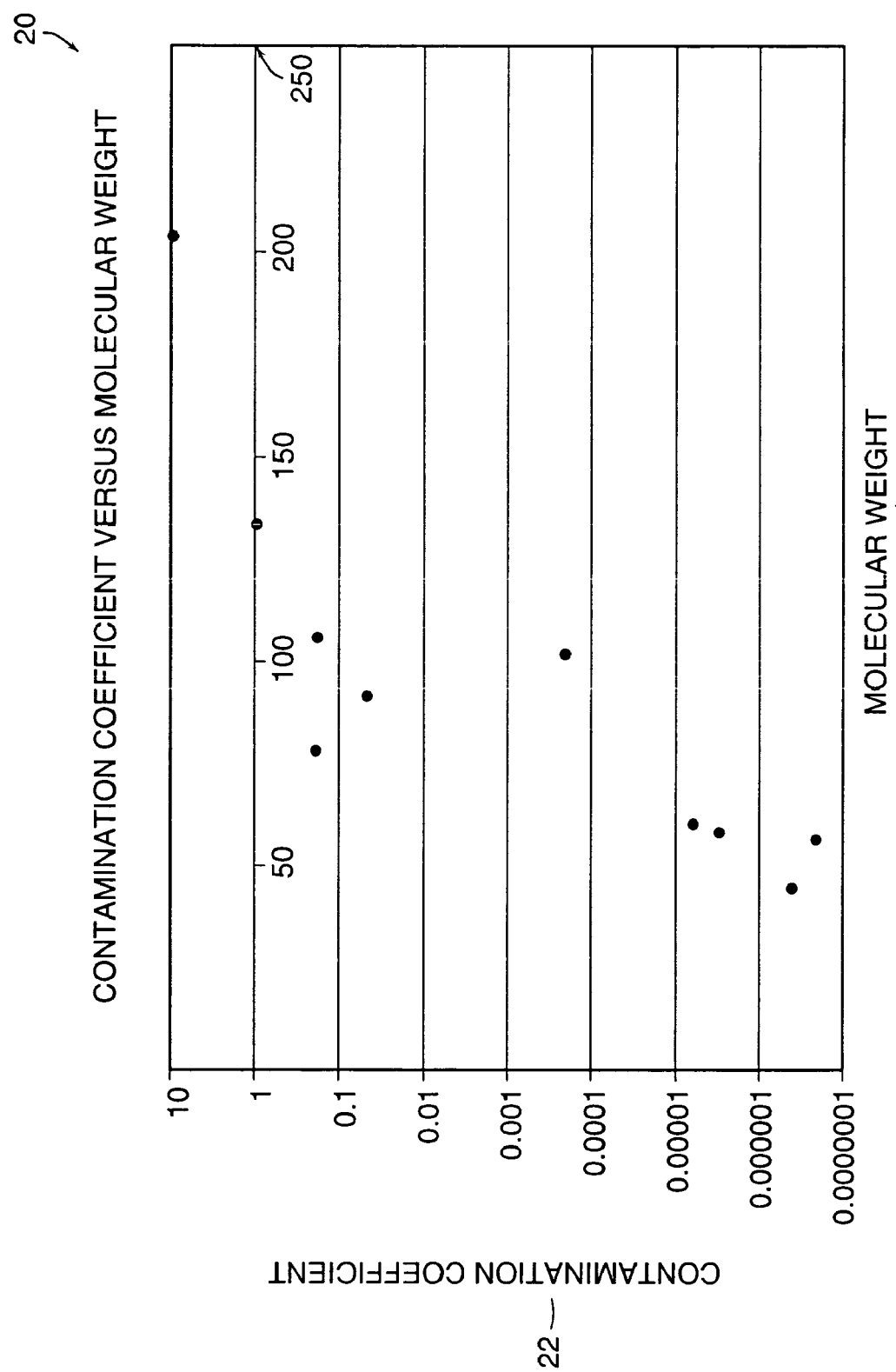
FIG. 1 is a graphical representation of contamination coefficient versus molecular weight.

The present invention is directed to a system and method for determining and controlling contamination. Preferred embodiments of the present invention address gaseous contamination as well as the contaminants adsorbed on surfaces, for example, an optical surface. The latter is more critical to the performance of the optical elements.

Table 1 illustrates various species in a cleanroom environment, such as, for example, a fabrication environment using photolithography systems. The low molecular weight species, such as acetone, isopropyl alcohol and low molecular weight siloxanes are the most prevalent in manufacturing environments. Compounds that are most likely to reduce the performance of optics are compounds having a high contamination coefficient or a high molecular weight examples can include, but are not limited to, methoxytrimethyl silane, trimethyl silane and trimethyl silanol. These compounds appear in italics in Table 1 have a higher molecular weight, higher contamination coefficient and an inorganic component. Compounds that negatively impact optical systems may also be described and include refractory compounds such as silanes, siloxanes and iodates, in particular hexamethyldisiloxane (C6-siloxane).

TABLE 1

| Compound (in cleanrooms) | Typical concentration, ppbV |
| --- | --- |
| Isopropyl Alcohol | 610.0 |
| Acetone | 330.0 |
| Ethanol | 134.0 |
| Silane, Methoxytrimethyl- | 35.0 |
| Heptane, Hexadecafluoro- | 28.0 |
| 2-Pentanone | 17.0 |
| 2-Butanone(MEK) | 9.8 |
| Hexane, Tetradecafluoro- | 8.9 |
| Butanoic Acid, Heptafluoro- | 5.2 |
| Tetrahydrofuran | 3.3 |
| 3-Buten-2-one | 2.5 |
| 4-Methyl-2-pentanone(MIBK) | 1.9 |
| Silane, Trimethyl(1-Methylethoxy)- | 1.7 |
| n-Pentane | 1.4 |
| Silanol, Trimethyl- | 1.4 |

Optics design also affects the relative sensitivity of the system to contamination. For example, light transmission is important in transmissive optical systems, like windshields, wherein reflectance approaches zero. High reflectivity systems, where transmission approaches zero, are inherently twice as contamination sensitive as transmissive optical systems because photons pass through any contaminating film twice, whereas light energy is only absorbed or scattered once in transmissive systems.

Describing the effect of molecular films on optical surface properties in terms of mathematics yields equation 1, for reflectance, and equation 2 for transmission.

$$\rho x(\lambda) = \rho(\lambda)\exp[-2\alpha c(\lambda)x]  \quad \text{Equation 1}$$

$$\tau x(\lambda) = \tau(\lambda)\exp[-\alpha c(\lambda)x]  \quad \text{Equation 2}$$

Where:
$\rho$=reflectance
$\alpha$=absorbance
$\tau$=transmittance
$\lambda$=wavelength
$\alpha c$=absorbance of a contaminating film, empirically determined Both transmitted and reflected energy, which is information used in lithography instruments and tools in semiconductor fabrication systems, drop exponentially with the accumulation of molecular films on optical surfaces. In lithography processes, the first order effect of molecular films on lenses is typically a reduction in light intensity due to energy absorbance by the contaminating film. These transmission losses reduce the number of wafers processed per hour, and consequently reduce productivity. This is analogous to the power reductions in spacecraft solar arrays, caused by accumulating molecular films. Secondary effects, in lithography processes, involve a reduction in image uniformity, which reduces critical dimension uniformity and yield.

Photochemical decomposition reactions occur when high-energy photons interact with organic vapors. These reactions form extremely reactive free radicals from otherwise neutral and relatively inert organic molecules. Irrespective of where radical formation occurs, in the gas phase or on the surface of optical elements, the resulting free radicals may react to form much larger organic compounds, which can contaminate optical elements. In severe cases, a polymer layer may be formed on the optical surface. The relationship between the chemical nature of the organic species and wavelength of light it absorbs can affect the nature and severity of optics contamination. For example, I-line or 365 nm wavelength light is energetic enough to break down only a few iodated components, which are not commonly found in clean room air. 248 nm wavelength light, typically used in deep ultraviolet (DUV) lithography for fabricating 250 to 150 nm linewidth devices, is more efficient and reacts with most halogenated organics and may even interact with some common hydrocarbons. 193 nm light, required for less than 130 nm geometries, reacts very efficiently with a wide range of airborne or gaseous molecular organic contaminants. 157 nm optical elements are even more sensitive to environmental conditions than 193 nm optics because this wavelength of light is efficiently absorbed or interacts with nearly all organic species plus oxygen and atmospheric moisture, requiring the exposure area, the area between the final optical element and the wafer, commonly called the free working area, to be purged with an inert, clean, dry, oxygen-free gas.

As the wavelength of light used in the lithography exposure tool decreases, the energy per unit photon increases. These progressively higher energy photons stand a better chance of breaking the bonds of a number of commonly present molecular species, ultimately rendering them into reactive species that stick to optical surfaces. The overall structure of a molecule plays a significant role in the ability of a photon to break any specific bond. Table 2 summarizes optics contamination as the lower wavelengths of electromagnetic spectrum are used to provide for the fabrication of smaller features.

Atmospheric pressure, low K1 factor optical lithography for less than 150 nm critical dimension on 300 mm wafer substrate device production may be the basis of advanced Integrated Circuit (IC) production in the near term. In these technology nodes, lithography-induced critical dimension variations have a particularly acute affect on device characteristics. For example, the standard deviation of propagation delay times for CMOS based ring-oscillators increases from 1% for 300 nm devices to 20% in 250 nm devices. Variations in gate oxide, impurity, and gate lengths were the primary causes of variations in device delay times. Below 200 nm gate length, however, the impact of gate length variation accounts for a remarkable 80% of the effect. The criticality of dimension variation in 150 nm lithography, for example, has lead to a critical dimension control budget of 15 mn, post-etch, 3 sigma. Since exposure dose and image resolution are compromised by optics contamination in proportion to the location and thickness of the contaminating film, contamination needs to be prevented before it occurs.

TABLE 2

| Issue | λ = 248 nm | λ = 193 nm | λ = 157 nm | Comments |
| --- | --- | --- | --- | --- |
| Propensity to form photodeposits in nitrogen (<10 ppb O2) | Low | Moderate | Nearly certain | Assumes organic vapor concentrations in the low ppb range |
| Ability to photoclean optics surfaces in-situ using active oxygen | Low | Moderate | High | Based on oxygen absorption coefficients and organic layer absorbance |
| Interactions with hydrocarbons | Aromatics only, moderate absorbance | Aromatics absorb very strongly, other weakly | Nearly all hydrocarbons absorb | Interaction determines allowable levels of contamination before lens performance suffers |

Existing methods of contamination control in lithography involves the use of activated carbon filters and/or some combination of adsorptive and chemisorptive media to adsorb or chemisorb the contaminants in air and gas streams that come in contact with the lens surfaces. In some cases, periodic regeneration of the adsorptive beds by thermal desorption occurs. Passive adsorption is unable to practically capture and retain the lighter hydrocarbons, oxygen, and water that interfere with imaging using 193 nm and 157 nm light. The propensity to form photodeposits, ability to photoclean, and interaction of hydrocarbons is tabulated relative to different wavelengths of light in Table 2.

Filter systems for contamination control are described in U.S. application Ser. No.: 10/205,703, filed on Jul. 26, 2002 entitled "Filters Employing Porous Strongly Acidic Polymers and Physical Adsorption Media", U.S. application Ser. No.: 09/969,116, filed on Oct. 1, 2001 entitled "Protection of Semiconductor Fabrication and Similar Sensitive Processes", and U.S. application Ser. No. 09/783,232, filed on Feb. 14, 2001 entitled "Detection of Base Contaminants In Gas Samples", the entire teachings of the above referenced applications are being incorporated herein by reference in their entirety.

FIG. 1 is a graphical representation 20 of contamination coefficient 22 versus a molecular weight 24. Note that a higher contamination coefficient means that it is more likely to contaminate system optics. The nearer term 193 nm wavelengths show some correlation between the contaminants molecular weight and its ability to contaminate the lens. Consequently, while the higher molecular weight species are of greater immediate concern for lens contamination, the lower boiling point materials, which are typically in higher concentration in semiconductor cleanrooms as shown in Table 1, can become a concern due to their much higher concentration and ability to adsorb photon energy at progressively shorter wavelengths. Moreover, particularly at 157 nm, oxygen and water need to be removed from the light path because they also absorb photon energy.

Existing systems have many disadvantages including passive adsorption systems that do not effectively remove low molecular weight organic materials; the removal efficiency and capacity of passive adsorption systems are proportional to the concentration of the impurities. In this application, the inlet concentrations are very low, making efficiency and capacity correspondingly low; and on-site regeneration of passive adsorption beds requires periodic temperature increases to regenerate the beds. Since most advanced lithography systems must maintain air and gas temperature stability at typically less than 100 milliKelvin, to avoid heating or cooling the optics, which change their optical characteristics, this strategy is impractical in advanced lithography.

Figure 2:
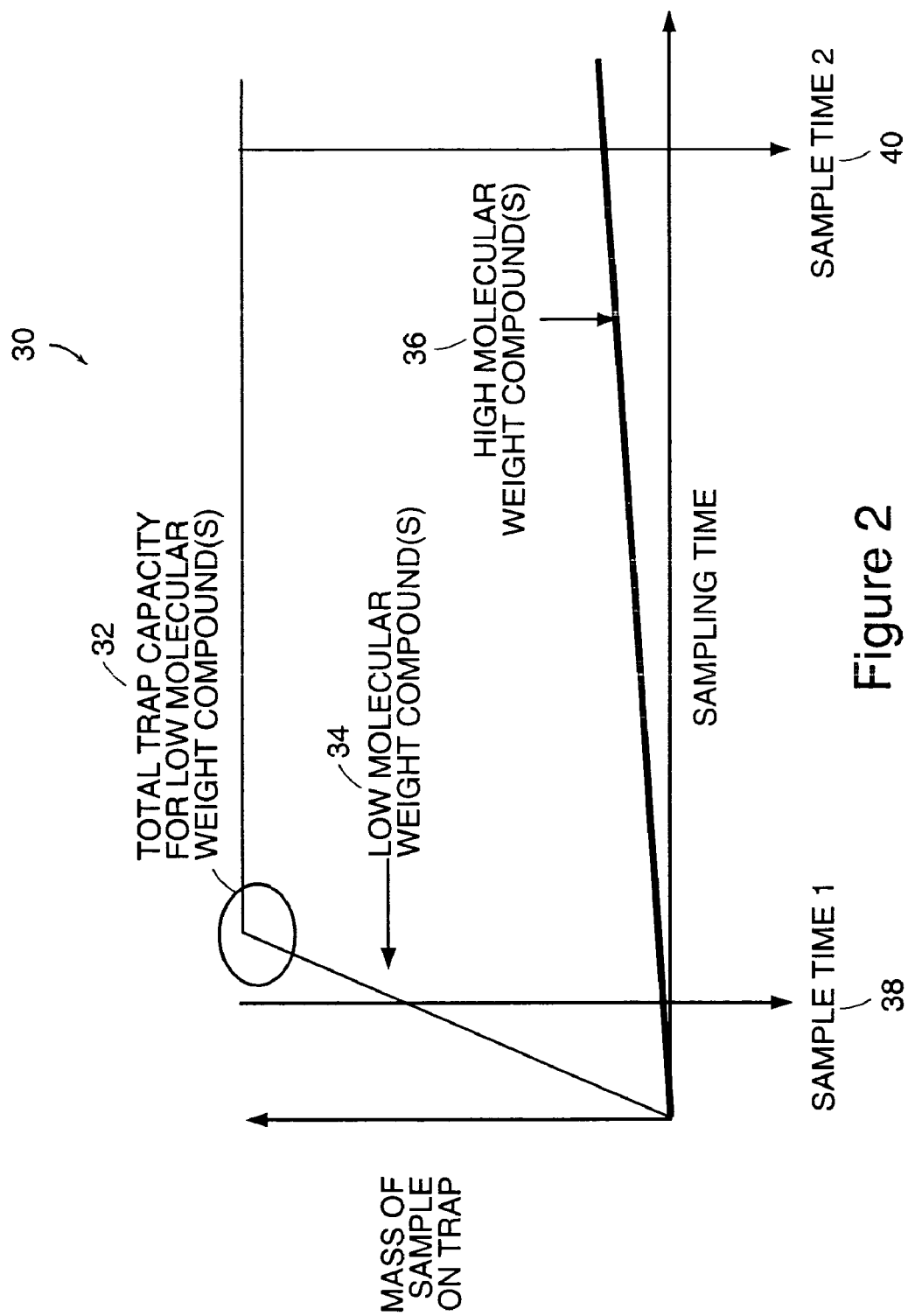
FIG. 2 is a graphical representation illustrating a comparison of a preferred embodiment of the system for determining contamination with respect to sample mass in a trap and sampling time in accordance with the present invention and the prior art.

FIG. 2 is a graphical representation 30 illustrating a comparison of a preferred embodiment of the system for determining contamination with respect to sample mass in a collection device or contamination trap and sampling time in accordance with the present invention and the prior art. An extended duration sample time, sample time 40, is used wherein the gas sample volume is not limited by the low molecular weight breakthrough volume, as is the case with the prior art method using sample time 38. In a preferred embodiment, the sampling time is at least six hours long and is preferably in a range of six hours to twenty-four hours. Higher capacity traps yielding longer collection times may be necessary for certain applications.

The extended time sampling method in accordance with a preferred embodiment of the present invention, collects higher masses of higher molecular weight compounds, which contribute to the contamination in the gas supply and which reduce the performance of optical elements more so than lower molecular weight compounds. Both high and low molecular weight compounds contribute to the contamination level but are operative at different rates. The high molecular weight compounds contribute to first order contaminating effects as they cause more damage to the optical systems even if present at low concentrations than low molecular weight compounds which contribute to third and fourth order effects. The collection device in accordance with a preferred embodiment is driven beyond saturation or breakthrough capacity to quantitatively measure the equilibrium concentration of low molecular weight compounds. The breakthrough volume is the amount of gas sample volume required to go beyond the absorbent capacity of the collection device. It should be noted that contaminates may be inorganic materials which may be carried by organics to the optical element. This extended time sampling method can also use different types of sample collecting media including those with adsorptive properties close to that of the optical surfaces of interest.

A preferred embodiment of the present invention includes "glass" or "coated glass" based adsorptive contamination traps. These contamination traps have not been used in the past due to their limited ability to collect and retain lower molecular weight species. These materials have surface properties identical or similar to properties of the optical elements used in the optical systems of photolithography tools. Other materials that emulate the surface properties of these optical elements that generate contamination can also be used.

In a preferred embodiment, the extended time sampling method may be extended from a few hours to several days and even weeks. The amounts of analyte collected represents the average value over time for compounds that have not reached their breakthrough time as illustrated by line 36 at sample time 2, line 40, and an average equilibrium concentration for those species that have already reached their breakthrough volume as illustrated by line 34 at sample time 2, line 40.

With respect to higher molecular weight species, the internal surface of the sampling lines and/or manifolds are kept at equilibrium with the gas phase sample, and therefore do not interfere with the sample collection process. In a preferred embodiment, between sampling sessions, flow through the sampling lines and/or manifolds is maintained.

Figure 3:
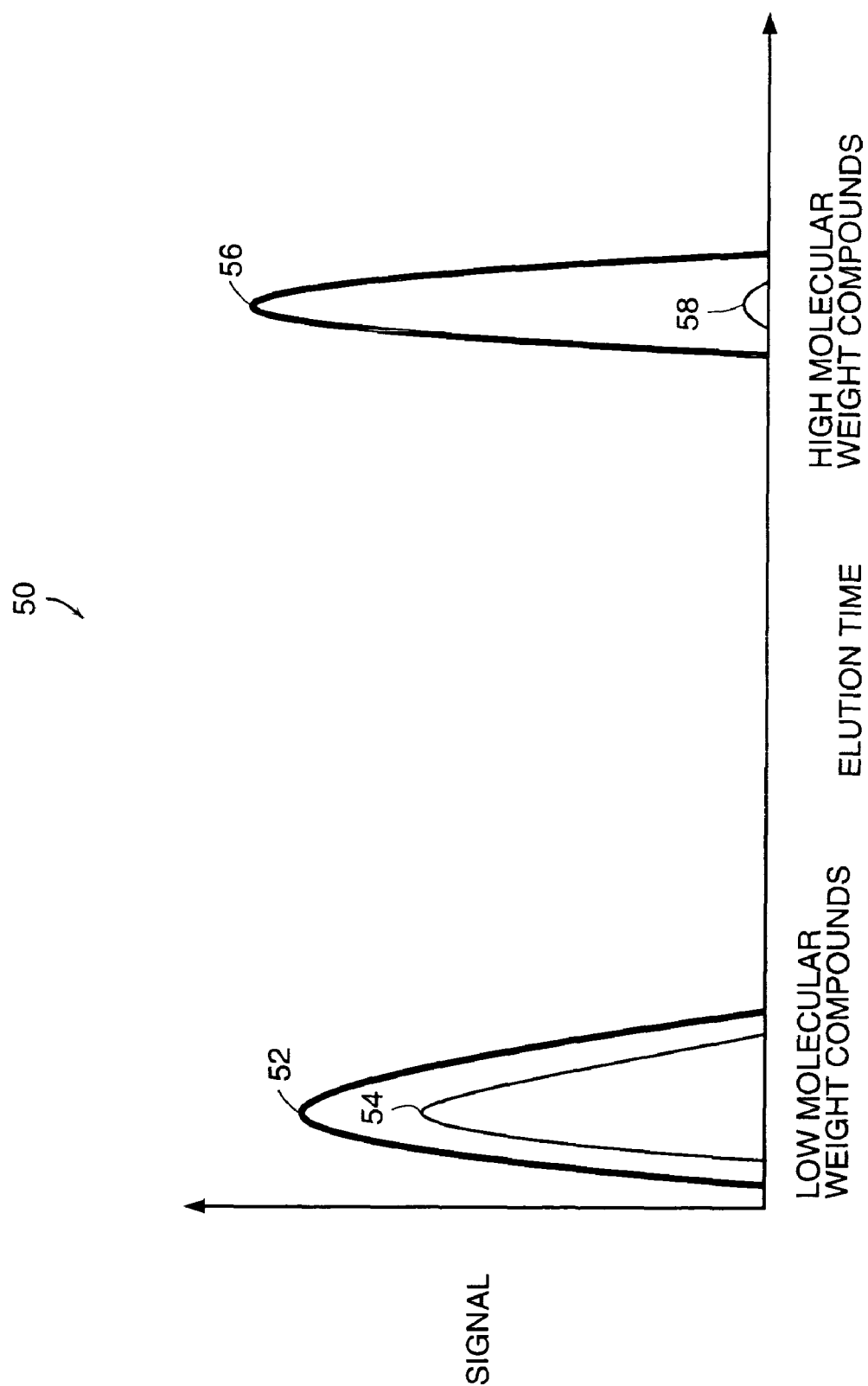
FIG. 3 is a graphical representation illustrating analyzed spectral comparisons of the system and method of determining contamination in accordance with a preferred embodiment of the present invention and the prior art.

FIG. 3 is a graphical representation 50 illustrating spectral analysis comparisons of the system and method of determining contamination in accordance with a preferred embodiment of the present invention and the prior art. The extended time sampling method of the present invention offers better sensitivity for components having high boiling points as illustrated by lines 52, 56. The results of the extended time sampling method in accordance with a preferred embodiment of the present invention better represent contamination on the optical surface, given the improved high molecular weight sample collection method of the present invention. A preferred embodiment of the system of the present invention provides the ability to use the actual optical surface of interest as the collection medium which in turn allows alignment of sampling surface properties and optical surface properties thereby making the analysis results more meaningful to the prediction of optics contamination.

The extended time sampling method in accordance with a preferred embodiment may reduce and preferably eliminate the uncertainties of sample loss on sample lines and/or manifolds. The extended time sampling method's simplicity minimizes the effect of uncontrolled contamination by personnel deploying the traps. Consequently, less training and experience are required to collect samples.

Figure 4:
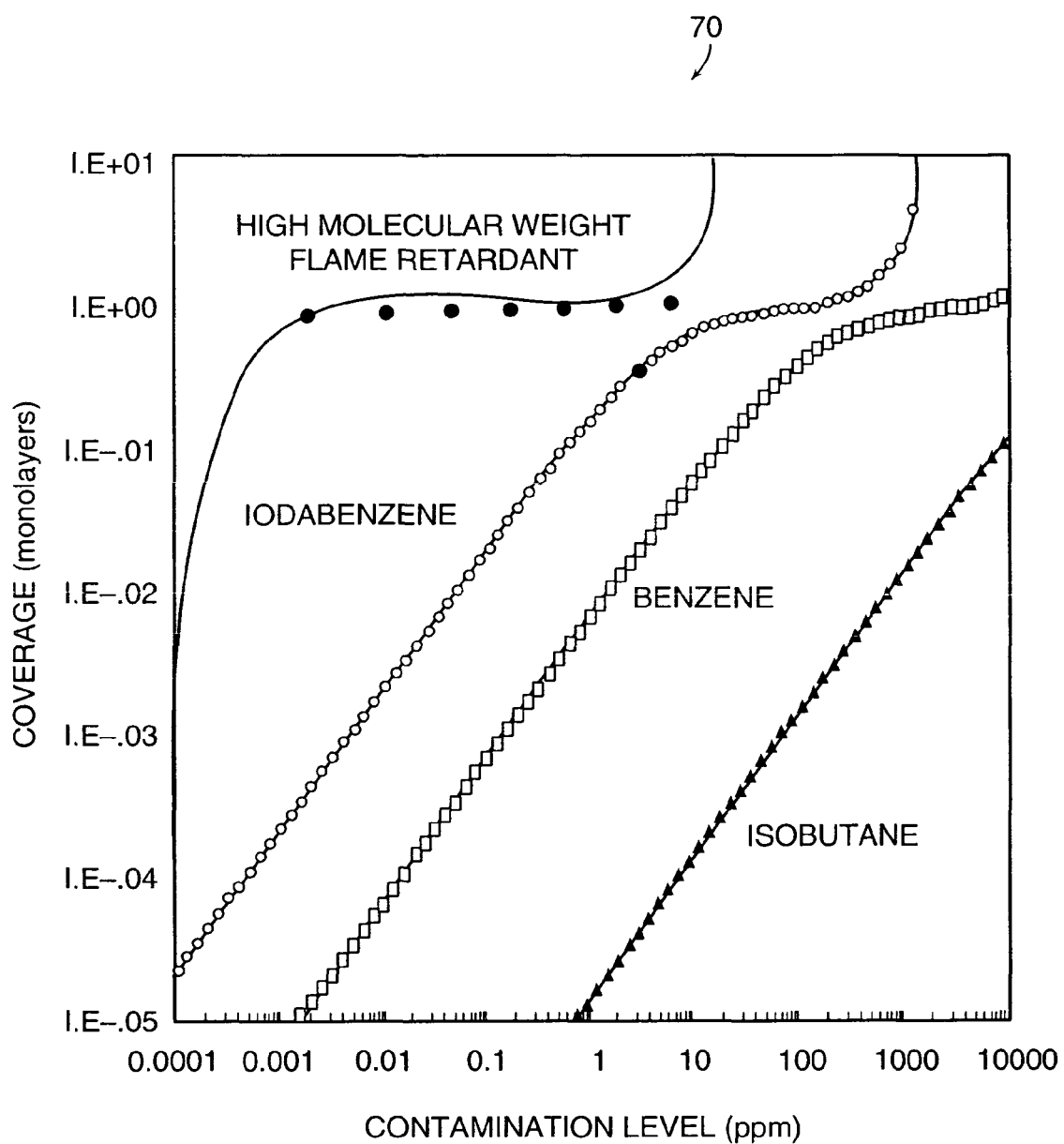
FIG. 4 is a graphical representation illustrating surface coverage as a function of contamination level in accordance with a preferred embodiment of the present invention.

FIG. 4 illustrates graphically surface coverage as a function of contamination level showing greater surface mass coverage per unit concentration in accordance with a preferred embodiment of the present invention. FIG. 4 illustrates this relationship for higher molecular weight components at the upper left with the lower molecular components towards the lower right of the graph. For a given concentration, the higher molecular weight compounds collect on surfaces more readily than do lower molecular weight species. One of the problems with the prior art method is that due to the shorter sampling times, much of what little sample is available for collection collects on the sample tube walls and manifold surfaces, all upstream of the collection trap, and never reaches the trap. This phenomenon causes a further loss of high molecular weight sample mass. Moreover, heated sampling lines and/or manifolds, which could ameliorate the problem, are not practical in the production cleanroom environment.

Figure 5:
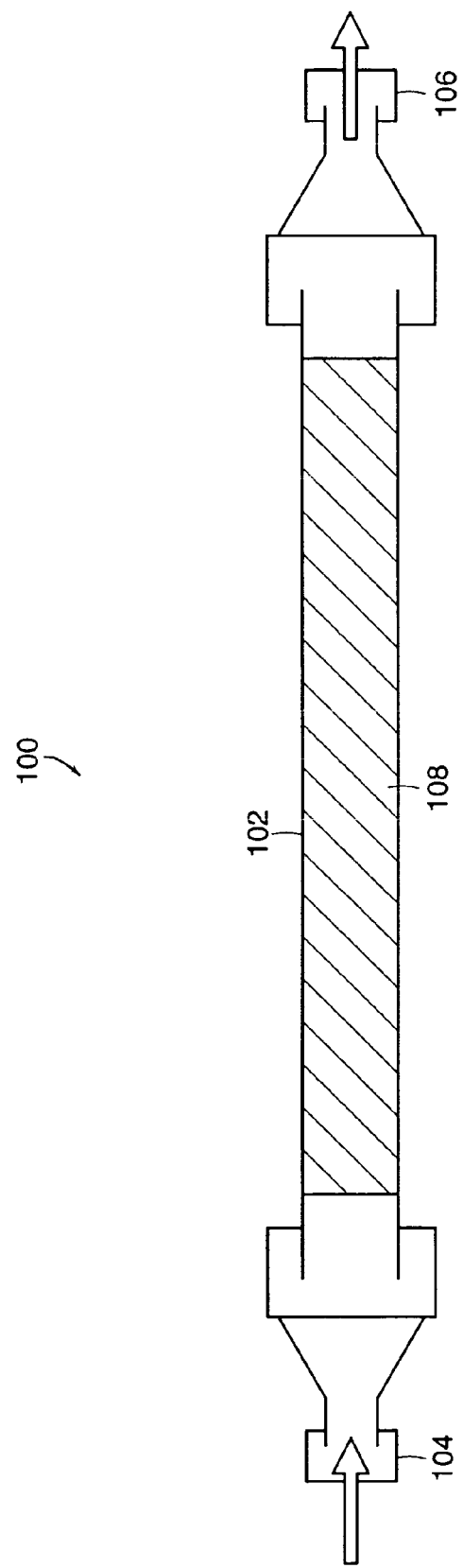
FIG. 5 is a preferred embodiment of a system of determining contamination in accordance with the present invention.

FIG. 5 is a diagram of a preferred embodiment of a system 100 for determining contamination in accordance with the present invention. The preferred embodiment of the apparatus includes a tubular collection device 102 having an inlet port 104 and an outlet port 106. In a preferred embodiment, the collection device includes, absorptive materials 108 such as, for example, glass spheres of a given size. In a preferred embodiment, crushed glass spheres are used. In another preferred embodiment, the absorptive material 108 is the polymer Tenax® supplied by, for example, Supelco. Tenax® has a high capacity for high boiling point compounds and operating Tenax® past low molecular weight breakthrough capacity allows the capture of a meaningful and analyzable mass of high molecular weight compounds. To collect a sample, an end cap in the inlet post is removed, allowing gas from a gas source to pass through the inlet port 104. Laser light may be directed through the sampling tube in a preferred embodiment of the present invention. The free radicals of the contaminants present in the gas sample may bond with the absorptive media 108 in the collection device 102.

In a preferred embodiment of the system for controlling contamination, multiple sample tubes and blank collection devices may be used. The collection device or refractory trap is applicable to both high pressure sampling, for example, purge gas, venting to the atmosphere assuming sufficient pressure and filter sampling, wherein the traps are connected to a vacuum source. The flow is controlled by an easily changeable critical orifice.

In a preferred embodiment, the trap contains three sample tubes, one blank and two active sample devices. Chemical analysis of the data may be correlated to transmission or image uniformity loss of the lithography tool, for example, using a regression analysis which weights first, second, third and fourth order effects: Uniformity or Intensity=a $[C_6$-siloxane$]+$b$[C_6$–$C_{30}]+$c$[C_3$–$C_6]+$d$[C_1$–$C_5]$ herein the parenthetic expressions are indicative of the concentration of species. First and second order contaminating effects have a greater impact on contamination of optical systems than third or fourth order contaminants and typically show a greater contamination coefficient (e.g. a>b>c>d). The first order contaminants may comprise high molecular weight refractory organics such as, for example, $C_6$ siloxanes and $C_6$ iodide with an inorganic component which is not volatilized through combination with oxygen. Second order contaminants may comprise high molecular weight organics, such as, for example, compounds including carbon atoms within the range of approximately six to thirty carbon atoms ($C_6$–$C_{30}$). Third order effects can arise due to the contaminating effects of organics such as $C_3$–$C_6$ that have approximately three to six carbon atoms. Further, fourth order contaminants Include organics such as, for example, methane, that have approximately one to five carbon atoms.

Figure 6:
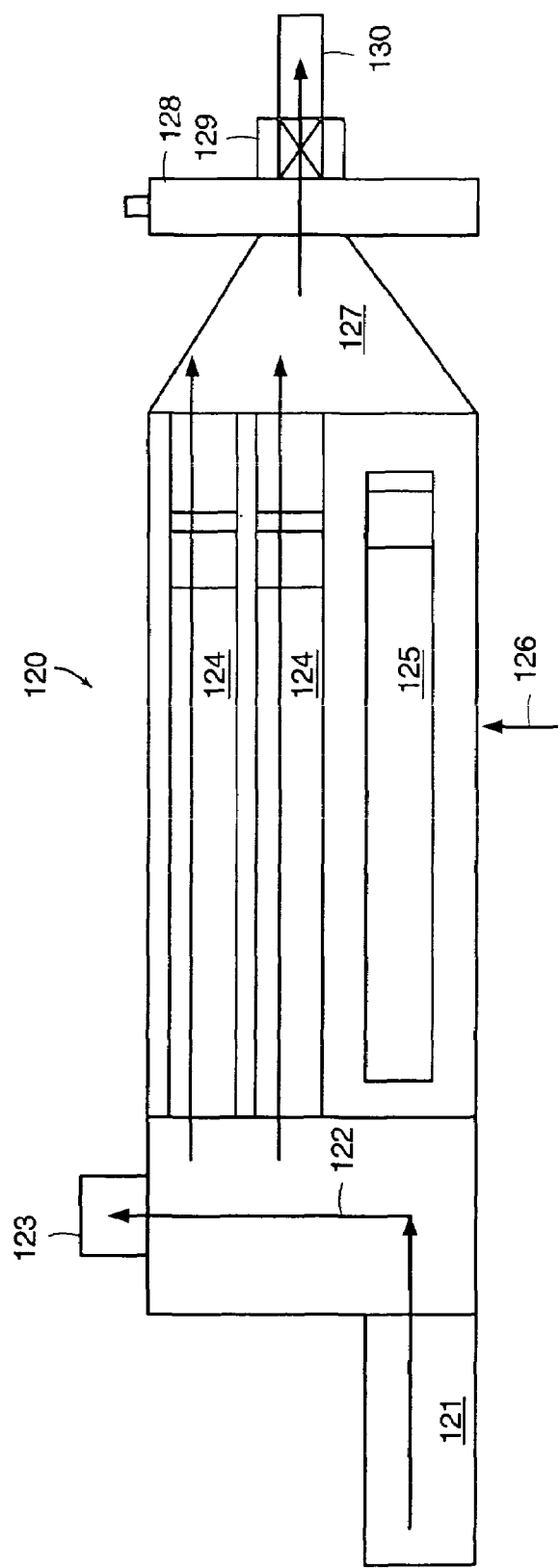
FIG. 6 is a preferred embodiment of a refractory trap system in accordance with the present invention.

In preferred embodiments of the system in accordance with the present invention, a refractory trap may be used both upstream and downstream of any in-line filtration system. FIG. 6 is a preferred embodiment of a refractory trap system 120 in accordance with the present invention. As described herein before refractory compounds include at least siloxanes such as, for example, hexamethyldisiloxane ($C_6$), silanes such as, for example, $C_3$-silane, silanols such as, for example, $C_3$ and iodates. The refractory trap system 120 includes a conduit 121 in communication with a gas source and through which a gas sample is carried with pressures ranging between approximately 1 to 120 psi. The gas sample is carried downstream to a pressure cavity 122. A pressure relief valve 123 allows the continuous flow of gas to ensure that the pressure cavity walls are in equilibrium with the gas phase of the gas sample. The refractory trap system 120 includes active sampling traps or collection devices 124 and a blank trap 125 in the trap cavity 126. The active sampling trap elements 124 may include an absorptive medium such as, for example, the polyler Tenax®. The gas sample flow in active elements is approximately 0.11 lpm. The blank trap 125 is not in communication with the gas source or pressure cavity and as such is not removing any contaminants. The outflow gas stream from the active collection devices 124 flows downstream into a manifold 127 which is in fluid communication with a vacuum line 130, via an orifice 129. A pressure/vacuum regulator valve 108 is disposed between the manifold and the orifice 129 to regulate pressure. The refractory trap system 120 provides for both a low pressure application or a high pressure application using a single design.

In a preferred embodiment, the gas supply may include a particular constituent such as hydrogen gas which may be used to clean the surfaces of the collection devices or, surfaces of optical systems that have been contaminated by a surface contaminant, for example, SiX. The gas additive combines with the surface contaminant to form a volatile compound that is then purged from the system. For example, SiX combines with hydrogen gas to form silane ($SiH_4$) which is volatile and is purged. The purge gas, is preferably in the ultra high purity gas level allowing the collection device to be placed upstream and downstream of typical in-line filters.

A sample report derived from a collection device may comprise the following information:
Contact information: Name, address, phone, email of person sending the sample
Tool #:
Gas sampled: N2 Air
Sample location:
  Upstream of filter
  Downstream of filter
  Interstack
Sample start date:
Sample end date:
Date received:
Report date:
Upstream Sample:
C2–C5: X ppb* (*equilibrium concentration)
C6–C30: Y ppb
Total siloxanes: z ppb
Total sulfur compounds:
Past history on this sample location:

In another preferred embodiment the collection device is located directly in contact with the airstream, thereby avoiding sample line contamination and using either passive diffusion or an active flow to collect the sample.

Figure 7:
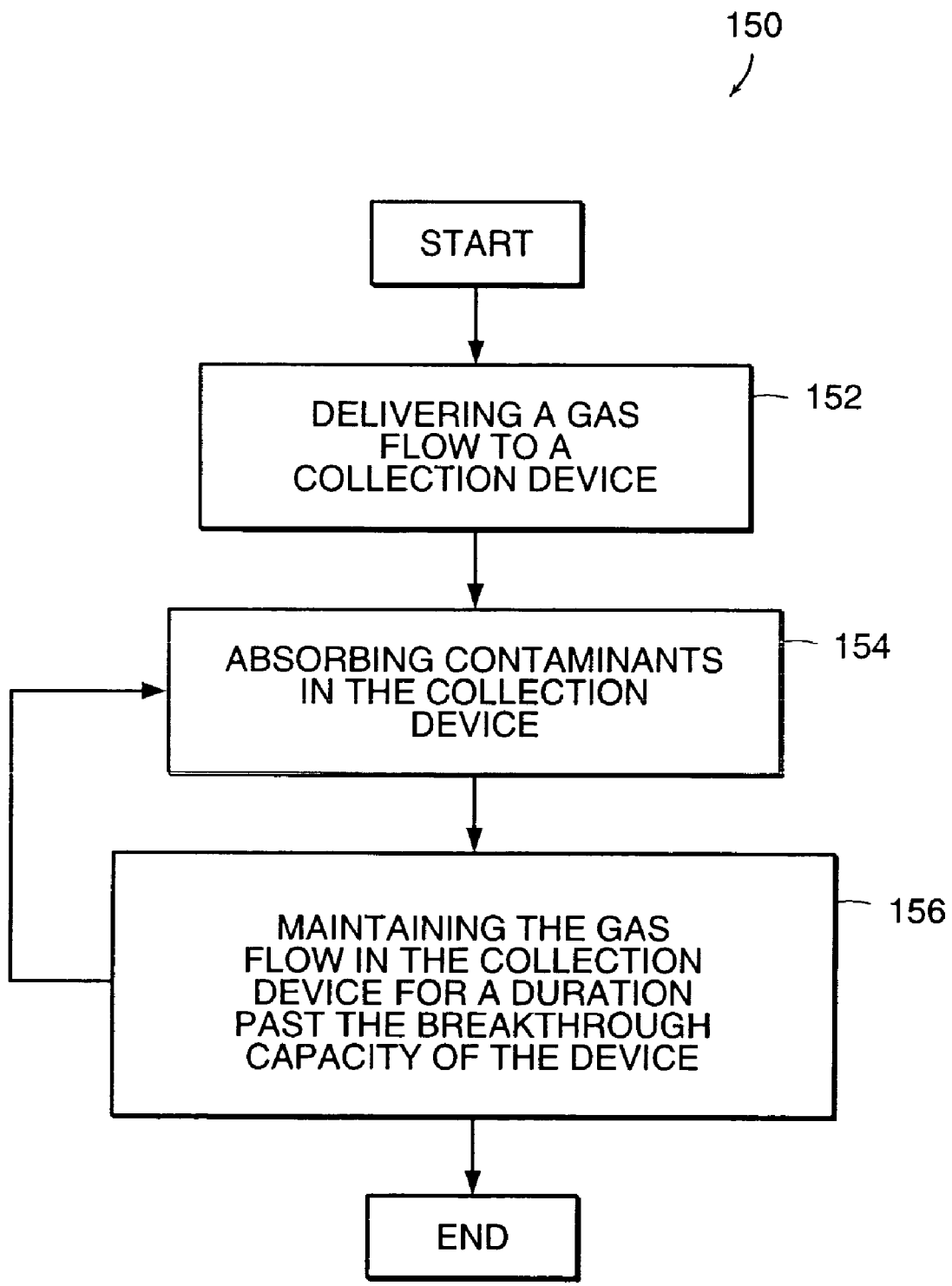
FIG. 7 shows a flow chart of a method of detecting contamination in accordance with a preferred embodiment of the present invention.

FIG. 7 is a flow chart of the method 150 of detecting and removing contamination in accordance with a preferred embodiment of the present invention. The method includes the step 152 of delivering a gas sample to a collection device. In a preferred embodiment, the collection device is as described with respect to FIG. 5 and/or FIG. 6. The method further includes the step 154 of absorbing contaminants contained in the gas sample in the collection device. The collection device is configured to emulate the environment of surfaces of optical elements. The method 150 includes the step 156 of maintaining the gas sample in the collection device for an extended duration sampling time which represents operation of the collection device past the saturation or breakthrough capacity of the device, for at least the lower molecular weight species. As described herein before the extended duration sampling time enables the collection of an equilibrium concentration of low and preferably high molecular weight compounds.

The internal surfaces of the sampling lines and manifolds are in equilibrium with the gas phase sample in order to not interfere with the sample collection process. In a preferred embodiment, the method 150 includes maintaining the flow of the gas sample through the sampling lines and manifolds.

In accordance with another preferred embodiment, the system of the present invention comprises a photolithography cluster tool, for example, an exposure tool, used in manufacturing semiconductor devices, that is sensitive to molecular contamination and a filtering system which removes the molecular contamination which may include volatile and semi-volatile or condensable organic substances, causing contamination of optical elements via series of homogeneous and/or heterogeneous ultraviolet (UV) induced processes. These optical elements are contained typically within a light path of a photolithography tool. In accordance with a preferred embodiment of the present invention, the filtering system for the ultra-purification of compressed fluids, for example, nitrogen, air or other suitable gases for purging of optical elements, with organic constituents comprises a membrane module, which separates the components of a given gas mixture by means of their different transport rates through the membrane. High removal efficiency of organic contaminants, in particular of first and second order contaminants may be obtained due to selective permeation on glassy polymers such as, for example, polyetherimide or rubbery polymers such as, for example, silicone rubber and also on porous ceramic membranes which generally have extended temperature limits up to approximately 300° C. Water and oxygen are preferably also removed using the membrane as they can degrade light transmission along the optical path in the system.

Membranes are generally available in two morphologies: homogeneous or composite. In the latter, thin polymeric permselective "skin" is deposited on a preformed porous substrate, which need not be the same polymer and may or may not interact with permeate. Polymeric membranes may be cast into various shapes: flat sheets for plate and frame and spiral wound modules, in the latter sheets and separating screens are wound into sandwich like structure by rolling around central permeate tube and self-supporting fibers, for example, hollow fibers and capillary membranes.

Figure 8:
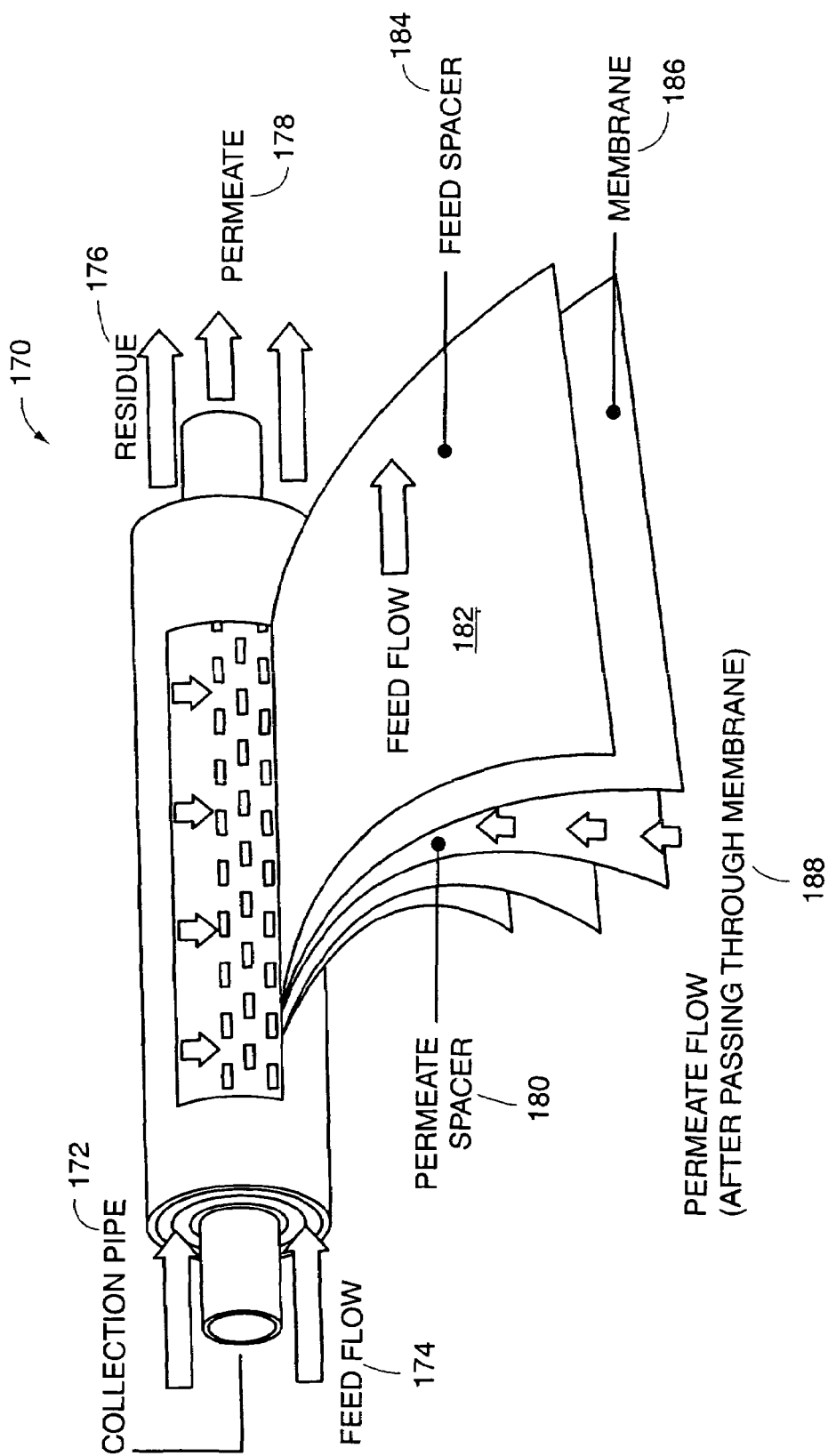
FIG. 8 is a diagram illustrating a preferred embodiment of a filtering system in accordance with the present invention.

In a preferred embodiment as illustrated in FIG. 8 the filtering system 170 comprises a filtration module based on a selectively permeable membrane 186 to filter organic compounds from a gas stream such as, for example, a nitrogen stream. The selectively permeable membrane may be of the type such as supplied by, for example, Membrane Technology & Research, Inc. In this preferred embodiment, the feed flow 174 is nitrogen that contains some amount of organic contamination. The feed flow may comprise 99–100% nitrogen with any balance in organic contaminants as well as water and oxygen. Assuming 90% removal efficiency of the membrane, the composition of the residue is purified by a factor of 10. The composition of the permeate stream can be enriched with organic contaminants. The filtering system 170, in accordance with a preferred embodiment of the present invention preferably removes contamination effects of first through fourth order contributors.

In another preferred embodiment the filtering system 170 comprises a filtration module based on a selective membrane 186 to filter organic compounds from a gas stream 174 wherein the collection device or pipe 172 is connected to a vacuum source to increase the pressure gradient across the membrane 186 to increase membrane efficiency. In this embodiment the feed flow 174 is nitrogen that contains some amount of organic contamination. In a particular embodiment the feed flow, 174 can include nitrogen with organic contaminants as indicated above. Assuming a 99% removal efficiency of the membrane, the composition of the residue 176 is again improved by a factor of 10 for nitrogen and the balance in organic contaminants. The composition of the permeate stream 178 is further enriched with organic contaminants.

In another preferred embodiment, the filtering system 170 comprises a filtration module based on a selective membrane 186 to filter organic compounds from a gas stream. In this particular embodiment the feed flow is nitrogen that contains some amount of organic contamination. The feed flow 174 comprises 99–100% nitrogen with the balance being organic contaminants. Assuming 90% removal efficiency of the membrane, the composition of the residue 176 is 99–100% nitrogen and the balance in organic contaminants. The composition of the permeate stream 178 may be enriched with organic contaminants. The organic contaminant enriched airstream 178 is then directed to a regenerative adsorption device for purification. The permeate stream 178, which has been purified by an adsorption bed system, is then returned to the feed flow. This filtering system in accordance with a preferred embodiment of the present invention reduces the loss of feed flow volume.

In another preferred embodiment, the filtration module consists of a composite membrane, a support of which is pretreated with a solid electrolyte washcoat and an oxide catalyst to promote electrochemical decomposition of the permeate 178 within the support at relatively low temperature.

In another preferred embodiment, the filtering system 170 comprises a filtration module based on a selective membrane 182 to filter organic compounds from a gas stream. In this embodiment, the feed flow 174 is nitrogen that contains some amount of organic contamination. The feed flow comprises 99–100% nitrogen with the balance being organic contaminants, oxygen, and water. Assuming 90% removal efficiency of the membrane, the composition of the residue is again improved by a factor of 10 for nitrogen with the balance being organic contaminants, but the membrane may not be selective enough to remove oxygen and water. Accordingly, the residue 176 of the filter system 170 is then directed to a second filter system, of similar mechanical construction to the first, which contains a different membrane specifically selected to allow oxygen and water to traverse the membrane, but is, again, less permeable to nitrogen. The residue of this second filter system may now be substantially free of organics, water, and oxygen which are all hazards to advanced lithography processes. Again, the composition of the permeate stream may be enriched with organic contaminants, water, and oxygen.

This filtering system can be used to purify nitrogen, synthetic air, clean dry air, all gas streams used in advanced photolithography, or any other compressed gas used in semiconductor processing. It may be, however, advantageous to filter synthetic air prior to mixing, for example, filter oxygen and nitrogen separately, before mixing them together to make synthetic air.

The filtering system may be constructed without limitation in a number of ways such as, for example, rolled-up supported membrane, rolled up self-supporting membrane, membrane disposed on a prefabricated porous supporting structure, a cylindrical pleated air filter, or comprise hollow fiber bundles through which the feed flow is directed.

The preferred embodiments of the filter system of the present invention remove both high and low molecular weight organic compounds and other unwanted contaminants such as water vapor, oxygen, inorganic impurities, effectively, and with a low concentration feed flow. In addition, the filter systems of the present invention operate continuously without filter replacement or pressure, flow, or temperature change or disruption. The preferred embodiments of the present invention address the problems of the prior art filters which have a limited capacity for low molecular weight hydrocarbons and rely on regenerative thermal cycles, which cause instability of the output gas temperature. The preferred embodiments of the filtering systems of the present invention provide an unlimited capacity for removing low molecular weight hydrocarbons and other contaminating species, independent of feed flow concentration, produce no sudden changes in the output flow conditions, and are easy and inexpensive to maintain.

Figure 9A:
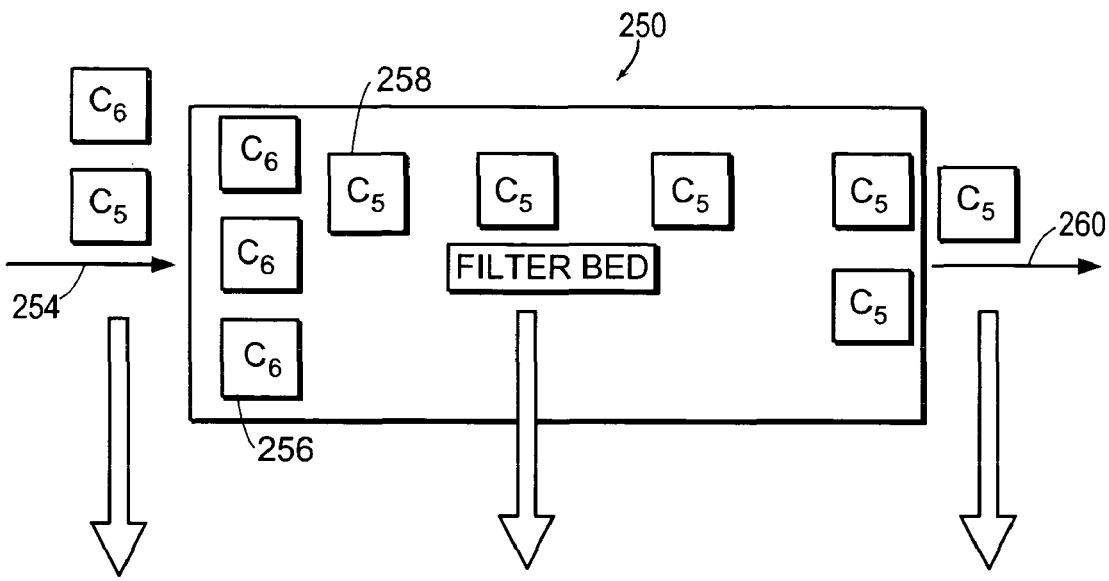
FIGS. 9A and 9B illustrate a schematic block diagram of a filter device having a bed showing the retention of different species in the bed and a graphical representation of the efficiency of the filter bed with respect to time by measuring the different species, respectively, in accordance with a preferred embodiment of the present invention.

FIG. 9A illustrates a schematic block diagram of a filter device having a bed showing the retention of different species in the bed in accordance with a preferred embodiment of the present invention. This preferred embodiment takes advantage of the inherent property of physioadsorbants to show different retention times for different species. For example, lower molecular weight species move through the carbon bed 252 more rapidly than do higher molecular weight species. As described hereinbefore, certain higher molecular weight species may be more contaminating to a process than lower molecular weight species. Accordingly, measurements are taken at a location upstream, in the middle of the chemical filter bed 252 or in an alternate preferred embodiment between two in-series filters, and at the discharge of relatively fast moving (moving through the filter bed) species, hereinafter referred to as leading indicator gases as indicators of the imminent breakthrough of the more slow moving species.

Figure 9B:
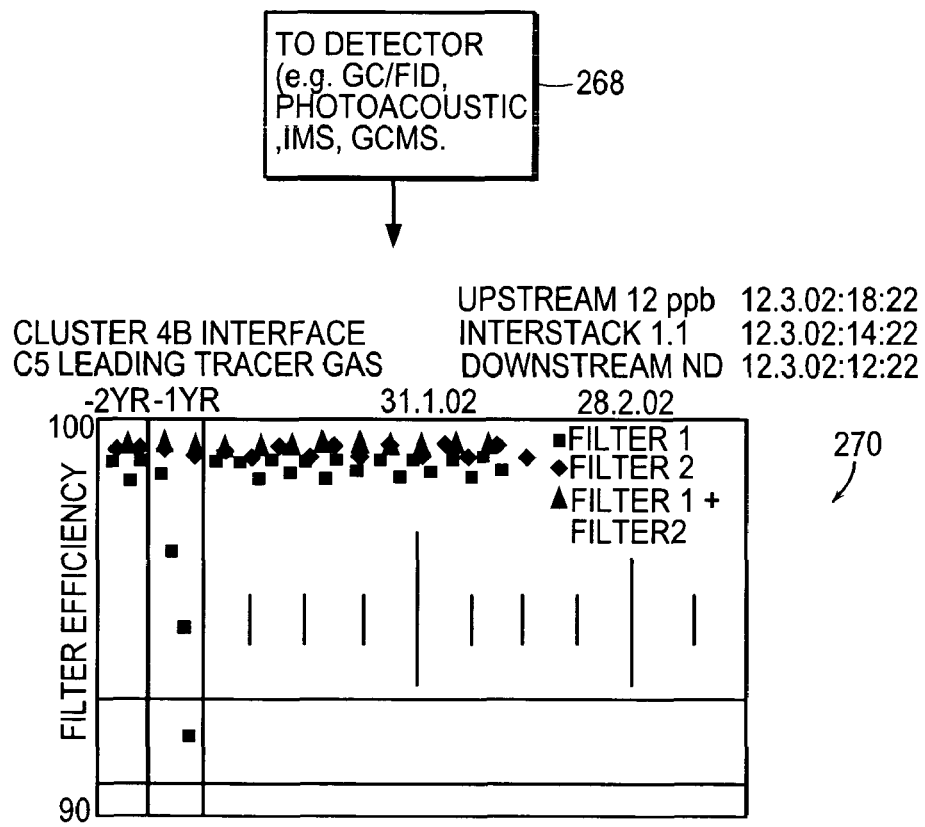

FIG. 9B graphically illustrates the efficiency of the filter bed with respect to time by measuring the different species in accordance with a preferred embodiment. In a preferred embodiment, the target gas is an C6 organic contaminant which may, or may not, contain an inorganic atom, and the leading tracer gas is a C5 organic species. The detector system in a preferred embodiment includes a thermal desorption preconcentrator coupled to a gas chromatograph with flame ionization detection. This system achieves the sensitivity the system requires to perform reliable low concentration work. Samples of the leading tracer gas are taken at various locations in the filter, before or after the filter or between two filters, for example, filter 1 and 2. The performance of the filter can be illustrated on a graphical user interface included in the system.

Figure 10:
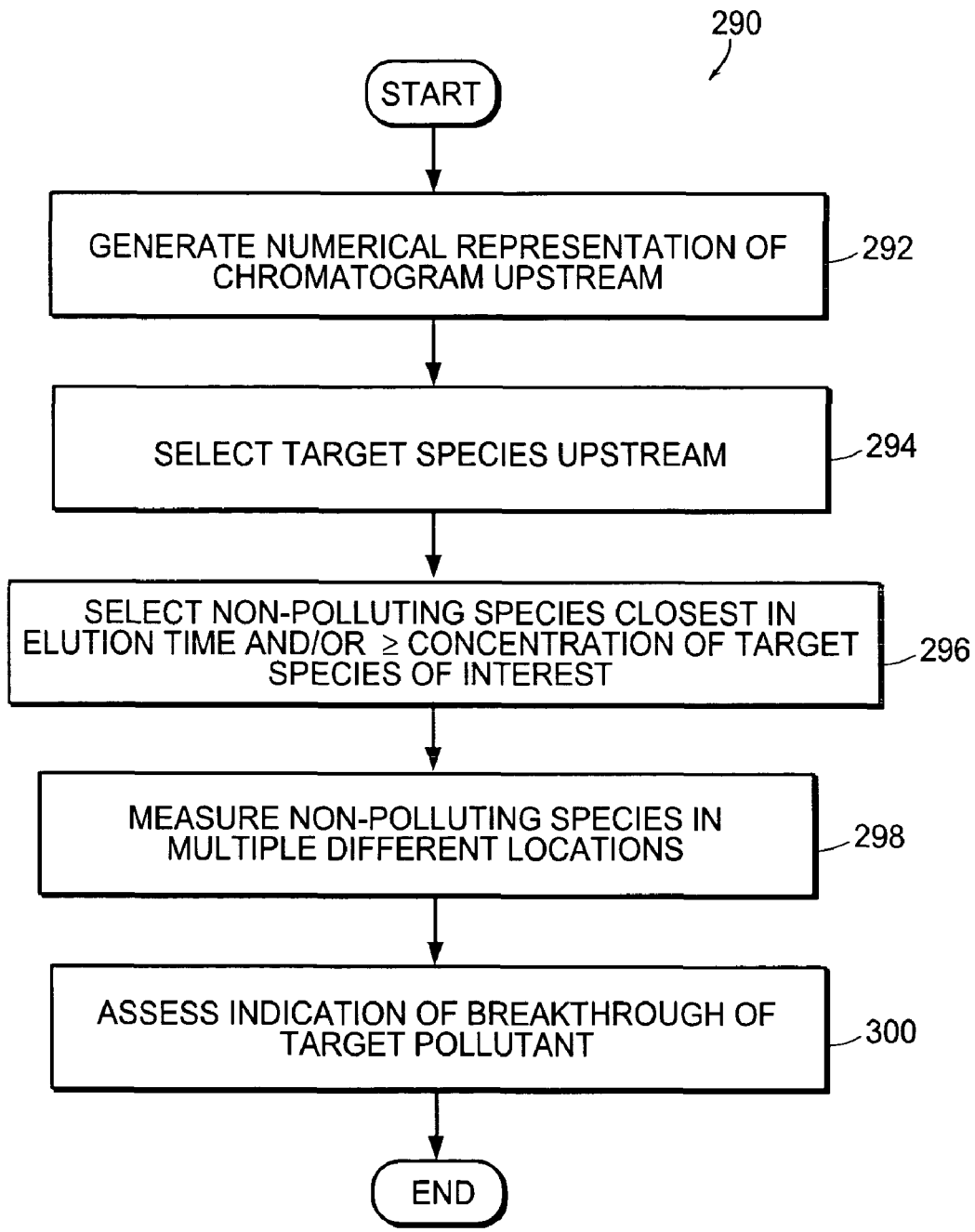
FIG. 10 is a flowchart of a method for monitoring the performance of a gas phase filter system in accordance with a preferred embodiment of the present invention.

FIG. 10 is a flowchart 290 of a method for monitoring the performance of a gas phase filter system in accordance with a preferred embodiment of the present invention. The method includes the generation of a numerical representation of the chromatogram of the gas flow upstream of the filter per step 292. Per step 294 the target polluting species are selected as the target is present at a detectable level upstream. In step 296 the non-polluting species that are the leading indicators are selected that are closest in elution (removing of absorbed material from adsorbent) time and greater than and equal to the concentration of target species of interest. The leading indicator tracer gas travels faster than the target pollutant through the filter bed. The method includes measuring the non-polluting species in different locations, for example, at a location prior to the filter bed, at a location in the middle of the filter bed and at a location at the discharge of the filter bed. The breakthrough of the target pollutant is then assessed and determined by the measurement of the leading indicator (tracer gas) as detected by a detector system per step 300.

A method for monitoring the performance of a gas-phase filter positioned in an air stream, which may be subject to molecular contamination, and useful for removing molecular contamination therefrom includes sampling the airstream at a location upstream of the air filter so that a variety of upstream molecular contaminants are detected and a target pollutant and a tracer gas are identified. The tracer gas travels faster than the target pollutant of interest in the filter. Further, the method includes sampling the airstream at a location downstream of the air filter so that the tracer gas is detected over time. The method includes determining the performance of the filter with respect to the target pollutant using a method that establishes a correlation between the low molecular weight compounds and the high molecular weight compounds and thus determining the performance of the air. In a preferred embodiment, the method includes sampling the airstream at a location in the middle of the filter bed.

Figure 11:
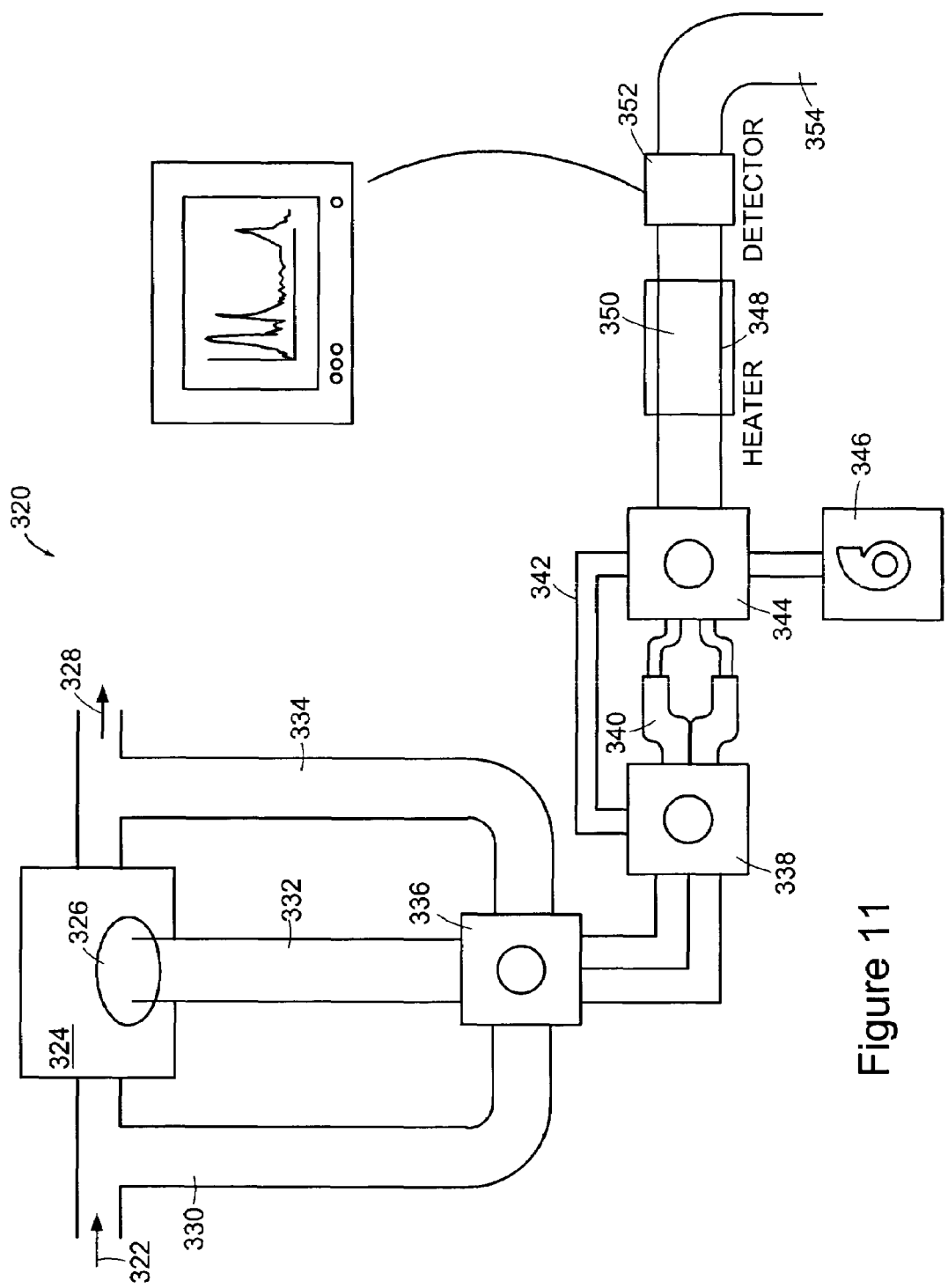
FIG. 11 is a schematic diagram of a system that includes a filter system in accordance with a preferred embodiment of the present invention.

FIG. 11 is a schematic diagram of a system 320 that includes a filter system in accordance with a preferred embodiment of the present invention. The gas flow or airstream 322 input into the filter 324 is sampled by a detector system. The filter bed includes a physioadsorbent to chemically adsorb contaminants. The air flow in the middle of the filter bed is also sampled and analyzed using a sampling port 326 that provides the sample to the detection system. The location of the sampling port 326 with respect to the outlet is proportional to the propagation rate of the leading indicator gas, for example, if the propagation rate of the tracer gas is high then the distance of the sampling port 326 from the outlet is raised. The discharge flow 328 at the outlet of the filter 324 is also sampled. A position selectable valve 336 disposed in the inlet of the detection system provides sampling capability for more than one stream. Thus, the sampled flow from the inlet of the filter bed, the middle of the filter bed or the outlet of the filter bed can be selected as input into the detection system. A valve 338 allows for the selection of the flow into a preconcentrator 340 or into a bypass 342. A pump 346 for the preconcentrator provides adequate flow therein. The discharge of the bypass or the preconcentrator is then selected by the valve to then form an input into a chromatographic column 350. A heater 348 is disposed around the chromatographic column 350. The outlet of the column forms the input of the detector 352 having a flame ionization detection system. The spectrum illustrating the abundance of the constituents detected with respect to time is displayed on a graphical user interface 358.

The preferred embodiment uses detection technology which is inherently sensitive to, and can identify and quantify organic species at very low concentrations, for example, below 1 ppb (V) using, for example, gas chromatograph/ flame ionization detection (GCFID). The preferred embodiments of the present invention provide advanced warning of filter failure without actually jeopardizing the process by allowing the actual species of interest to breakthrough. The preferred embodiment does so at a low enough concentration to be meaningful to highly sensitive processes, like optics systems.

In a preferred embodiment the filter includes a bed of the polymer pellets exposed to the airstream using a traditional media tray and rack system. In an alternative preferred embodiment the filter includes a honeycomb configuration with the polymer pellets held in a partially filled or completely filled honeycomb structure. Other embodiments include filter construction including, but not limited to, a monolithic porous or honeycomb structure formed from polymer, a mat of polymer fiber, either woven or nonwoven, pleated and arranged in a traditional air filter, a bed of the activated carbon pellets exposed to the airstream using a traditional media tray and rack system, a honeycomb configuration wherein the activated carbon pellets are held in a partially filled or completely filled honeycomb structure, a monolithic porous or honeycomb structure formed from the activated carbon, a mat of activated carbon fiber, either woven or nonwoven, pleated and arranged in a traditional air filter and a carbon based composite filter constructed of woven or nonwovens support structures.

In preferred embodiment the detection system may include any system that is capable of measuring organic compounds at very low concentrations including, but not limited to a GCFID with, or without a preconcentrator, a GCMS with, or without a preconcentrator, a photoacoustic detector with, or without a preconcentrator, and IMNS with, or without a preconcentrator, or any combination thereof.

In a preferred embodiment reactive inorganic materials, including molecular bases and molecular acids are included in the airstream. These compounds may react to form nonvolatile salt particles. Molecular condensable high boiling point organic materials which may be adsorbed on the optical elements and undergo DUV light induced radical condensation or polymerization. Resulting polymer films in some cases may be removed by active oxygen treatment species. Refractory materials are compounds containing atoms forming nonvolatile or reactive oxides, for example, but not limited to, P, Si, S, B, Sn, Al. These contaminants may be exposed to DUV light and may form refractory compounds resistant to active oxygen treatment.

In a preferred embodiment molecular bases and molecular acid samples are collected using impingers filled with distilled water (10 cc). An air (gas) sample is drawn through the impinger at 1 L/min for 240 minutes using a programmable sample pump. The total sample volume in a preferred embodiment, without limitation is 240 L.

Further, in a preferred embodiment, molecular condensable high boiling point organic materials and refractory material samples are collected using Thermodesorbtion Samplers (TDS) filled with porous medium, for example, Tenax® T.A. An air (gas) sample is drawn through the collection media at a flow of the 0.15 L/min for 240 minutes, using a programmable sampling pump with low flow adapter. Total sample volume is approximately 36 L. In preferred embodiments, the flow rate can vary in a range 50 cc/min to 250 cc/min. The temperature can also vary from approximately room temperature to approximately −100° C. Field blank or empty samples are collected for each type of sample. The field blank is a sample device (impinger of TDS), which is handled in the field the same way as an actual sample having zero sample volume drawn through. The purpose of the field blank is to detect possible uncontrolled contamination events during sample handling and transportation. Field blanks are analyzed in the same manner as actual samples.

In a preferred embodiment, analyses of molecular bases and molecular acids samples includes using Ion Chromatography methods. Compounds are identified by retention time and quantified using individual calibration standards and a 10-point calibration procedure. Low Detection Limit (LDL) of the corresponding methods is 0.1 ug/m$^3$ per individual component. In a preferred embodiment, molecular bases and refractory material samples are analyzed using a Gas Chromatograph (GC) equipped with a Mass selective Detector and Thermal Desorption System (TD). The total analytical system (TD/GC/MS) is optimized to separate and quantify analytes with a boiling temperature of hexane and higher with LDL of ~0.1 ug/m$^3$ per individual component. Individual components are identified by a MS library search and chromatographic peak position. Individual component are quantified against two analytical standards, for example, toluene and hexadecane. Analytical results are listed in the Tables 3–9.

TABLE 3

| | Concentration, ug/m3 | | | | | |
|---|---|---|---|---|---|---|
| | N2-facilities before | N2-facilities after | Oil free Air before | Oil free Air after | Fab amblent | Sub Fab |
| Ammonia (as NH3) | 0.4 | <0.1 | 0.4 | <0.1 | 4.2 | 6.4 |
| Other inorganic acids | <0.1 | <0.1 | <0.1 | <0.1 | <0.1 | <0.1 |
| Nitrous acid (as NO2) | <0.1 | <0.1 | 0.8 | <0.1 | 0.8 | 1 |
| Nitric acid (as NO2) | <0.1 | <0.1 | <0.1 | <0.1 | <0.1 | <0.1 |
| C6+ Organic Compounds (as toluene) | ~1.1 | ~0.9 | ~0.8 | ~2.3 | ~213 | H |

TABLE 4

| Compound | | Concentration, ug/m3 as toluene | as hexadecane |
|---|---|---|---|
| Benzene (78) | | 0.4 | 0.2 |
| Silane, Dimethoxydimethyl (59) | | 2.7 | 1.2 |
| Hexane, 3-Methyl (26) | | 0.4 | 0.2 |
| 2-Heptane (47) | | 0.5 | 0.2 |
| Silane, Trimethoxymethyl (45) | | 0.4 | 0.2 |
| Hexane, 2,5-Dimethyl (33) | | 0.3 | 0.1 |
| Toluene (82) | 1 | 2.9 | 1.3 |
| Propanoic acid, 2-hydroxy-ethyl ester (59) | 2 | 1.5 | 0.7 |
| PGMEA (92) | 3 | 2.2 | 1 |
| Ethylbenzene (59) | 4 | 3.2 | 1.3 |
| n-Propylbenzene (56) | | 0.3 | 0.1 |
| Cyclohexane (84) | | 9.5 | 0.2 |
| Xylenes (48) | 5 | 15.2 | 6.1 |
| Styrene (59) | | 0.3 | 0.1 |
| 1,2,3 Trimethylbenzene (72) | | 1.8 | 0.7 |
| 1,3,5 Trimethylbenzene (60) | | 0.6 | 0.2 |
| Cyclohexanone (77) | 6 | 0.6 | 0.2 |
| 3-Heptanone (47) | | 0.4 | 0.2 |
| Unknown | | 0.5 | 0.2 |
| Unknown | | 0.7 | 0.3 |
| Octane, 2,6-Dimethyl (59) | 7 | 0.3 | 0.1 |
| Cyclohexane, (1-Methylethyl) (40) | | 0.4 | 0.2 |
| Nonane (59) | | 0.4 | 4.1 |
| Octane, 2,5,6-Trimethyl (53) | | 4.3 | 1.7 |
| Octane, 2,2,7,7-Tetramethyl (53) | | 1.8 | 0.7 |
| Octane, 2,2,6-Trimethyl (64) | | 1.4 | 0.6 |
| Benzene, 1-Ethyl, 3-Methyl (93) | 8 | 3.1 | 1.2 |
| Decane, 2-Methyl (77) | | 1.2 | 0.5 |
| Benzene, 1-Ethyl, 2-Methyl (77) | | 0.9 | 0.4 |
| Benzaldehyde (48) | 9 | 2.8 | 1.1 |
| Carbamic acid, methyl-, phenyl ester (25) | | 2.1 | 0.8 |
| Propylene cabonate (86) | 10 | 3.5 | 1.4 |
| Heptane, 2,2,4,6,6-Pentamethyl (64) | | 2.6 | 1 |
| Decane, 2,2-Dimethyl (64) | 11 | 5.7 | 4 |
| Decane 2,2,9-Trimethyl (77) | 12 | 10.1 | 2.3 |
| Nonane, 3,7-Dimethyl (67) | 13 | 17 | 0.2 |
| Decane, 5,6-Dimethyl (50) | | 1.7 | 0.7 |
| Decane, 2,3-Dimethyl (40) | | 1.9 | 0.8 |
| Nonane, 3-Methyl-5-propyl (64) | | 3.9 | 1.6 |
| Decane, 2,6,7-Trimethyl (47) | 14 | 15 | 6 |
| Heptane, 4-Ethyl-2,6,6-Tetramethyl (72) | 15 | 14 | 0.2 |
| Undecane, 2,5-Dimethyl (59) | | 1.5 | 0.2 |

TABLE 4-continued

| Compound | | Concentration, ug/m3 as toluene | as hexadecane |
|---|---|---|---|
| Undecane, 4,6-Dimethyl (59) | 16 | 12 | 4.8 |
| Undecane, 3,5-Dimethyl (53) | | 1.8 | 0.7 |
| Undecane, 4-methyl (83) | | 2.4 | 1 |
| Nonane, 3-methyl-5-propyl (64) | 17 | 5.7 | 2.3 |
| Undecane, 5,7-Dimethyl (43) | | 1.7 | 0.7 |
| Undecane, 3,8-Dimethyl (38) | | 2.5 | 1 |
| Dodecane, 2,5-Dimethyl (36) | | 3.6 | 1.4 |
| Heptane, 2,2,3,4,6,6-Hexamethyl (72) | | 1.5 | 0.6 |
| Dodecane, 2,6,10-Trimethyl (72) | | 2.3 | 0.9 |
| Tridecane, 5-Methyl (64) | | 0.7 | 0.3 |
| Tridecane, 4-Methyl (64) | | 0.4 | 0.2 |
| Dodecane (50) | | 0.5 | 0.2 |
| Benzoic acid (66) | 18 | 9.9 | 4 |
| Cyclotetrasiloxane, Hexamethyl (39) | | 0.5 | 0.2 |
| Cyclotetrasiloxane, Octamethyl (54) | | 0.4 | 0.2 |
| 2,5 Cyclohexadiene-1,4-dione,2,5,-diphenyl (97) | 20 | 27 | 10.1 |
| Total | | 213 | 73 |

Figure 12A:
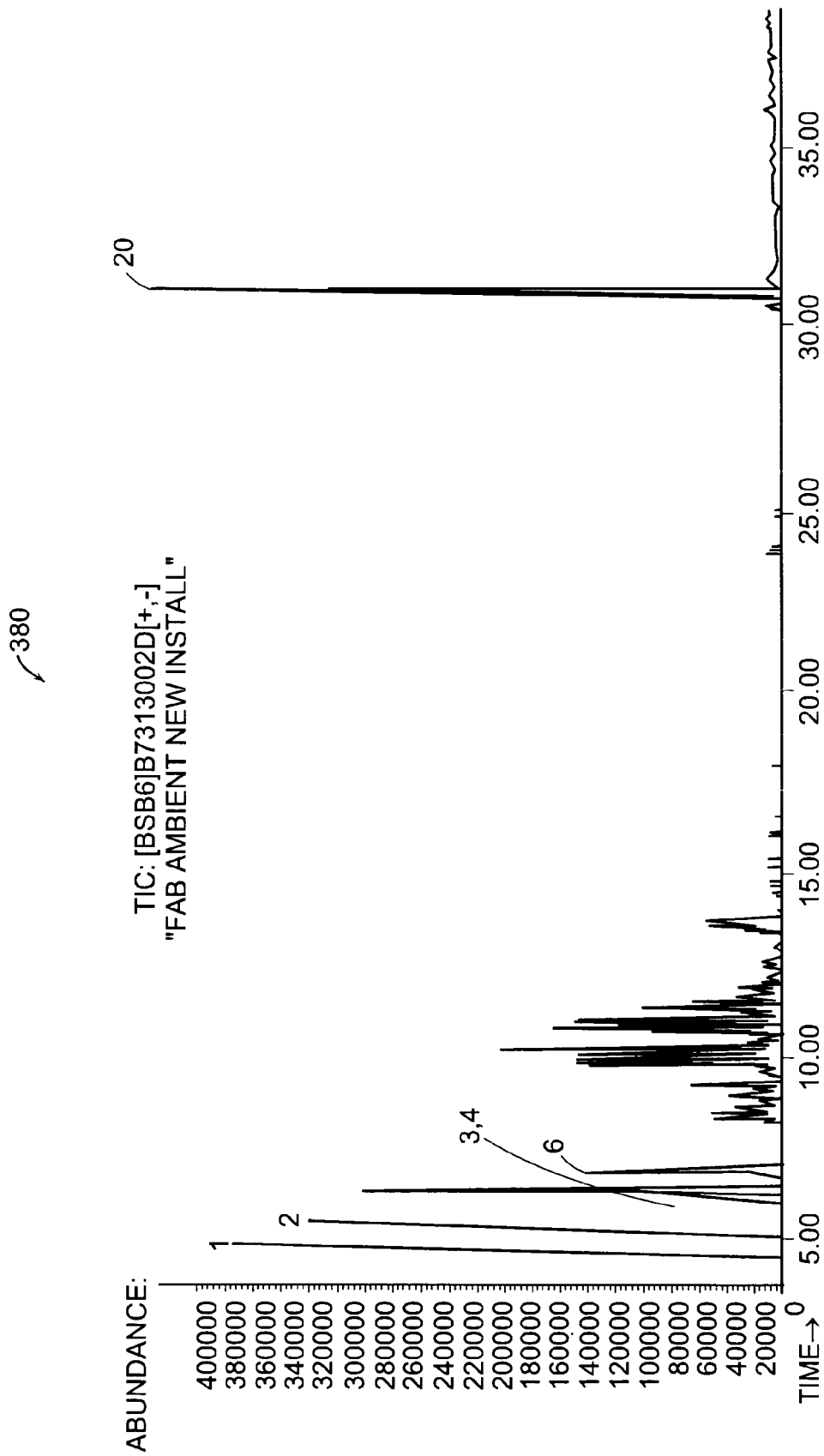
Figure 12B:
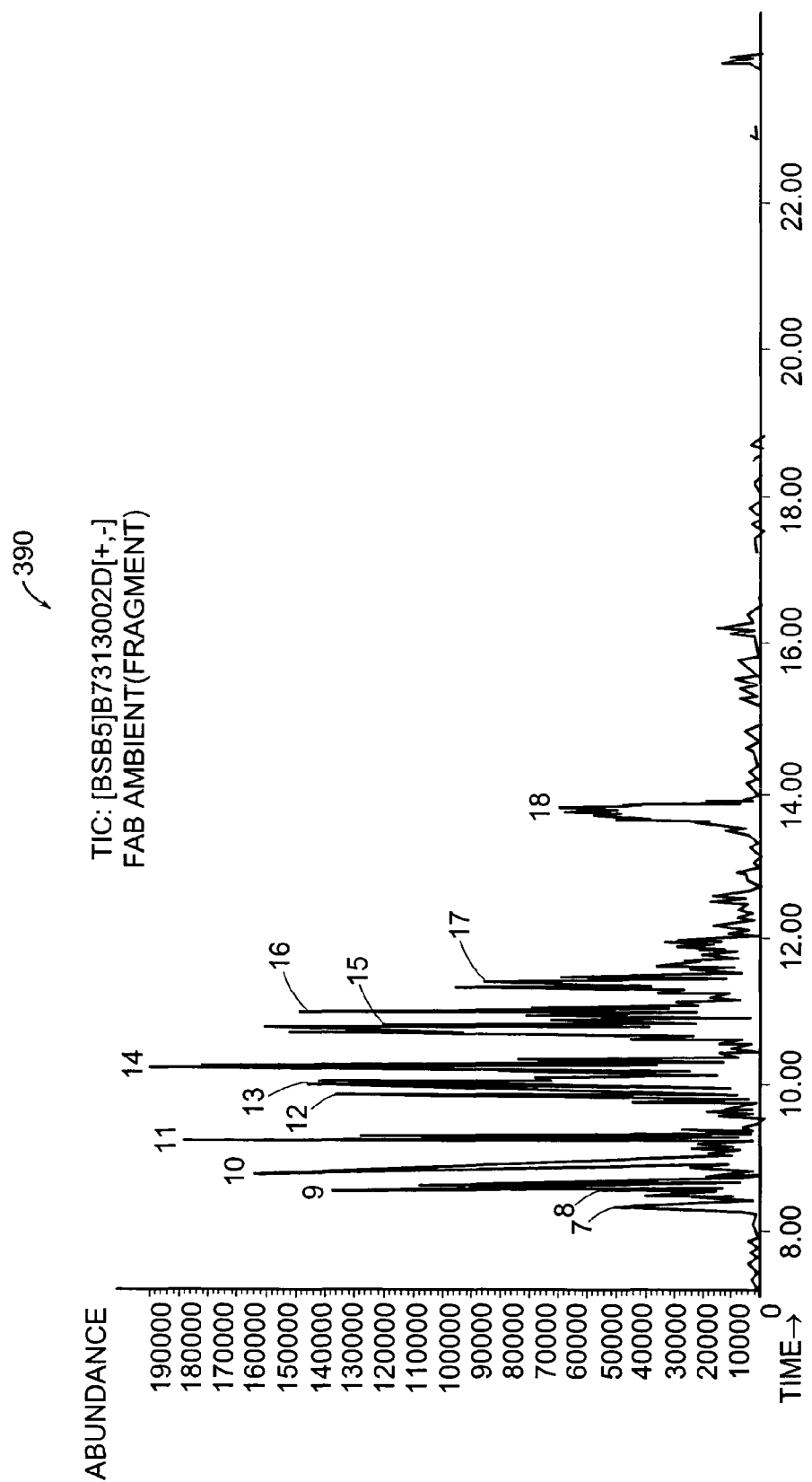

FIGS. 12A–12C are graphical illustrations of chromatograms of a gas sample including an average ion scan of the spectra end (FIG. 12C) in accordance with a preferred embodiment of the present invention. The gas sample is fabricated ambient air.

The mass spectrometry (MS) results for sub-fabricated air are listed in Table 5.

TABLE 5

| Compound | | Concentration, ug/m3 as toluene | as hexadecane |
|---|---|---|---|
| Hexane (78) | | 0.4 | 0.2 |
| Benzene (84) | | 0.5 | 0.2 |
| 3-Pentanone, 2,4-Dimethyl (72) | | 0.2 | 0.1 |
| Hexanal (64) | | 0.3 | 0.1 |
| Propanoc acid, 2-hydroxy, propyl ester (56) | | 0.4 | 0.2 |
| Propanoc acid, 2-oxo-ethyl ester (29) | | 0.1 | 0.05 |
| Toluene (79) | 1 | 3.3 | 1.4 |

TABLE 5-continued

| Compound | | Concentration, ug/m3 as toluene | as hexadecane |
|---|---|---|---|
| 3-Pentanone, 2,4-Dimethyl (36) | | 0.2 | 0.1 |
| 2,3-Dimethyl Pentane (21) | | 0.4 | 0.2 |
| Propanoic acid, 2-hydroxy, propyl ester (57) | | 0.4 | 0.2 |
| Propanoic acid, 2-oxo-ethyl ester (27) | | 0.1 | 0.05 |
| PGMEA (59) | | 0.8 | 0.3 |
| Ethyl Benzene (61) | 4 | 7 | 4.9 |
| Styrene (39) | | 0.3 | 0.1 |
| Xylenes (35) | 5 | 35 | 17.5 |
| 1,2,4-Trimethylbenzene (67) | | 1.4 | 0.6 |
| Nonane (61) | | 0.7 | 0.3 |
| 2-Furanol, tetrahydro-2-Methyl (56) | | 1.1 | 0.5 |
| Cyclohexanone (73) | 6 | 92 | 40 |
| Octane, 2,5,6-Trimethyl (50) | 7 | 1.7 | 0.7 |
| Benzene, 1-Ethyl-3-methyl (91) | 8 | 2.2 | 0.9 |
| Decane, 3,4-Dimethyl (59) | | 0.4 | 0.2 |
| Benzene, 1-Ethyl-2-methyl (72) | | 0.5 | 0.2 |
| Alpha-methylstyrene (96) | | 1.1 | 0.4 |
| Heptane-2,2,4,6,6-Pentamethyl (42) | | 0.8 | 0.3 |
| Benzaldehyde (96) | 9 | 0.9 | 0.4 |
| Decane, 2,2-Dimethyl (64) | 11 | 1.7 | 0.7 |
| Decane, 2,2,9-Trimethyl (53) | 12 | 4.2 | 1.7 |
| Nonane, 3,7-Dimethyl (47) | 13 | 4.7 | 1.9 |
| Benzene, 1,3,5-Trimethyl (91) | | 0.6 | 0.2 |
| Undecane, 3,6-Dimethyl (38) | | 1 | 0.4 |
| Decane, 2,6,7-Trimethyl (53) | 14 | 4.2 | 1.7 |
| 1-Hexanol, 2-Ethyl (47) | | 1.2 | 0.5 |
| Undecane, 3,8-Dimethyl (43) | | 3.4 | 1.4 |
| Undecane4,6-Dimethyl (59) | 16 | 0.5 | 0.2 |
| Nonane, 3-methyl-5-propyl (53) | 17 | 0.7 | 0.3 |
| Nonane, 5-Butyl (59) | | 1 | 0.4 |
| Undecane (90) | | 1 | 0.4 |
| Undecane, 4-Methyl (72) | | 1 | 0.4 |
| Benzene, 1-Ethyl-2,3-dimethyl (38) | | 0.5 | 0.2 |
| Benzene,-4-Ethyl, 1,2-dimethyl (72) | | 0.3 | 0.1 |
| Dodecane, 2,5-Dimethyl (40) | | 1.1 | 0.4 |
| Acetophenone (47) | | 0.7 | 0.3 |
| 1-Octanol, 2-Butyl (78) | | 0.4 | 0.2 |
| Benzene, 1-Ethyl, 2,4-dimethyl (47) | | 0.3 | 0.1 |
| Dodecane, 2,7,10-Trimethyl (59) | | 0.8 | 0.3 |
| Undecane, 2,7,10-Dimethyl (53) | | 0.3 | 0.1 |
| Benzoic acid (41) | 18 | 8.9 | 3.6 |
| Dodecane (87) | | 0.5 | 0.2 |
| Phenyl maleic anhydride (23) | | 0.4 | 0.2 |
| Trimethyl, 1,3-Pentadiol diisobutyrate (42) | 19 | 2.9 | 1.2 |
| Benzophenone (42) | | 0.1 | 0.05 |
| 2,5-Cyclohexadiene-1,4-dione-2,5-diphenyl (89) | 20 | 12.1 | 4.8 |
| Total | | 216 | 96 |

Figure 13A:
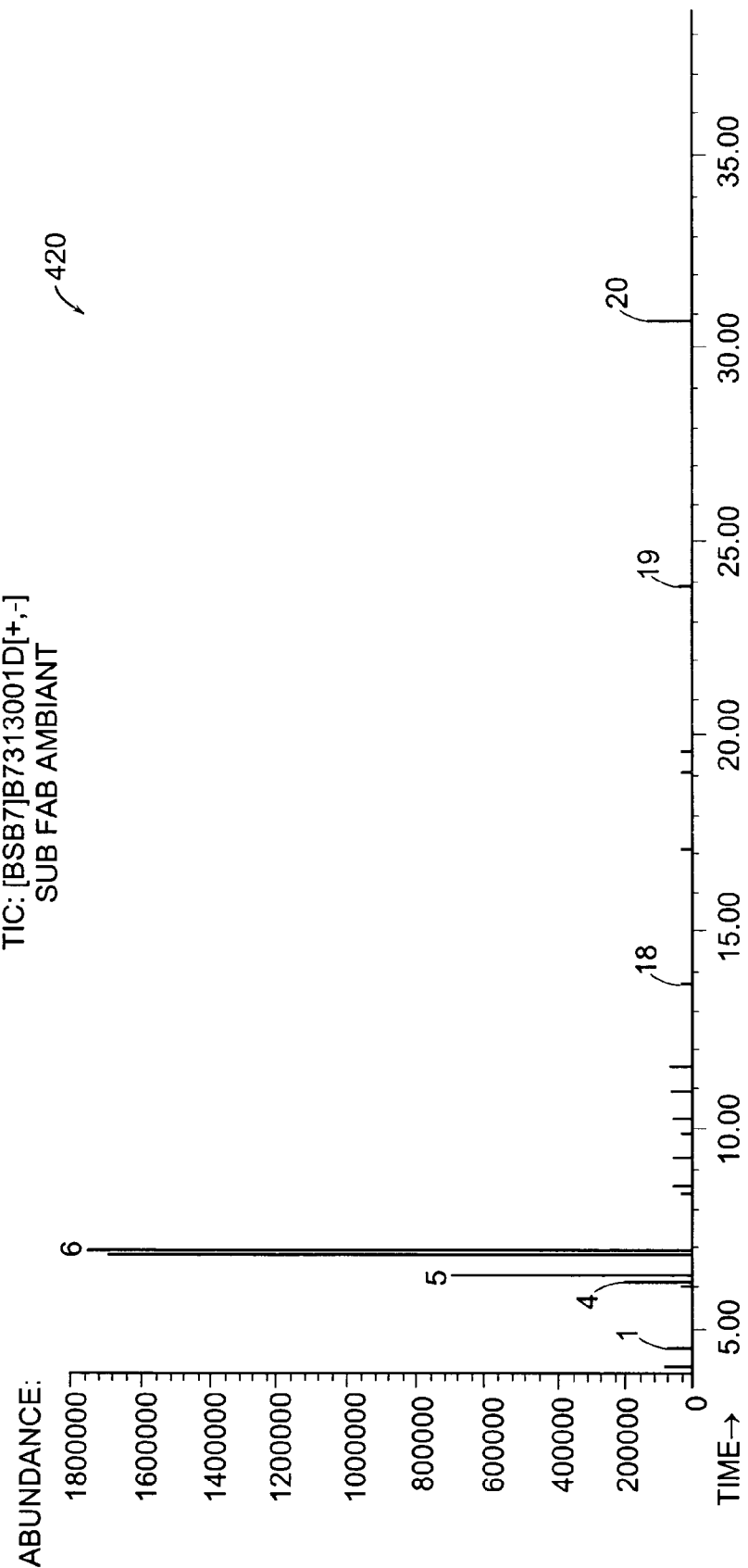
FIGS. 13A and 13B are chromatograms of a second gas sample in accordance with a preferred embodiment of the present invention.
Figure 13B:
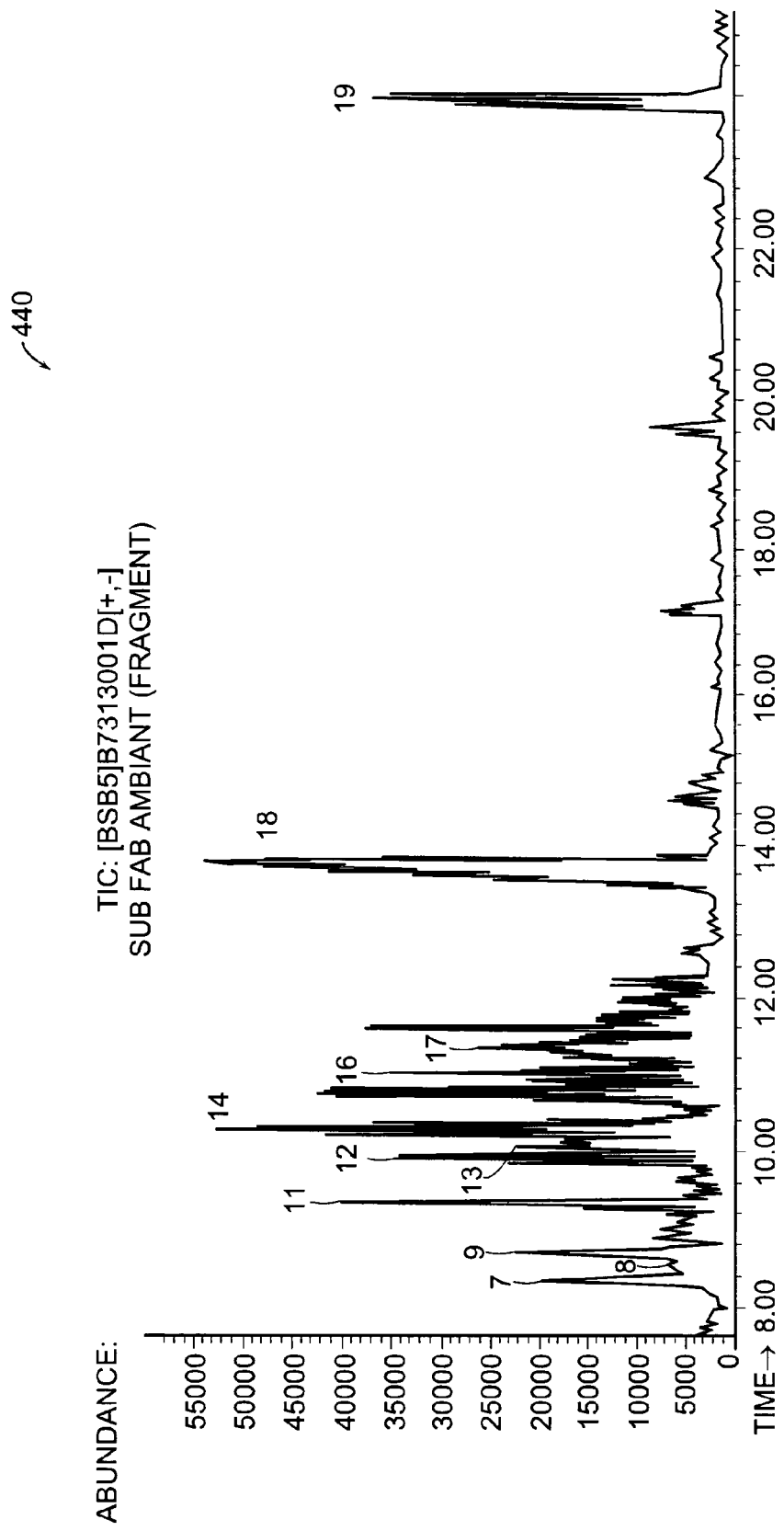

FIGS. 13A and 13B are chromatograms of another gas sample in accordance with a preferred embodiment of the present invention. The gas sample is a sub-fabricated ambient air sample.

Table 6 lists the mass spectrometry results for oil free air upstream of the filter.

TABLE 6

| Compound | Concentration, ug/m3 (as toluene) | as hexadecane |
|---|---|---|
| Silane, Dimethoxydimethyl | 0.5 | 0.2 |
| Toluene | 0.3 | 0.1 |
| Total | 0.8 | 0.3 |

Figure 14:
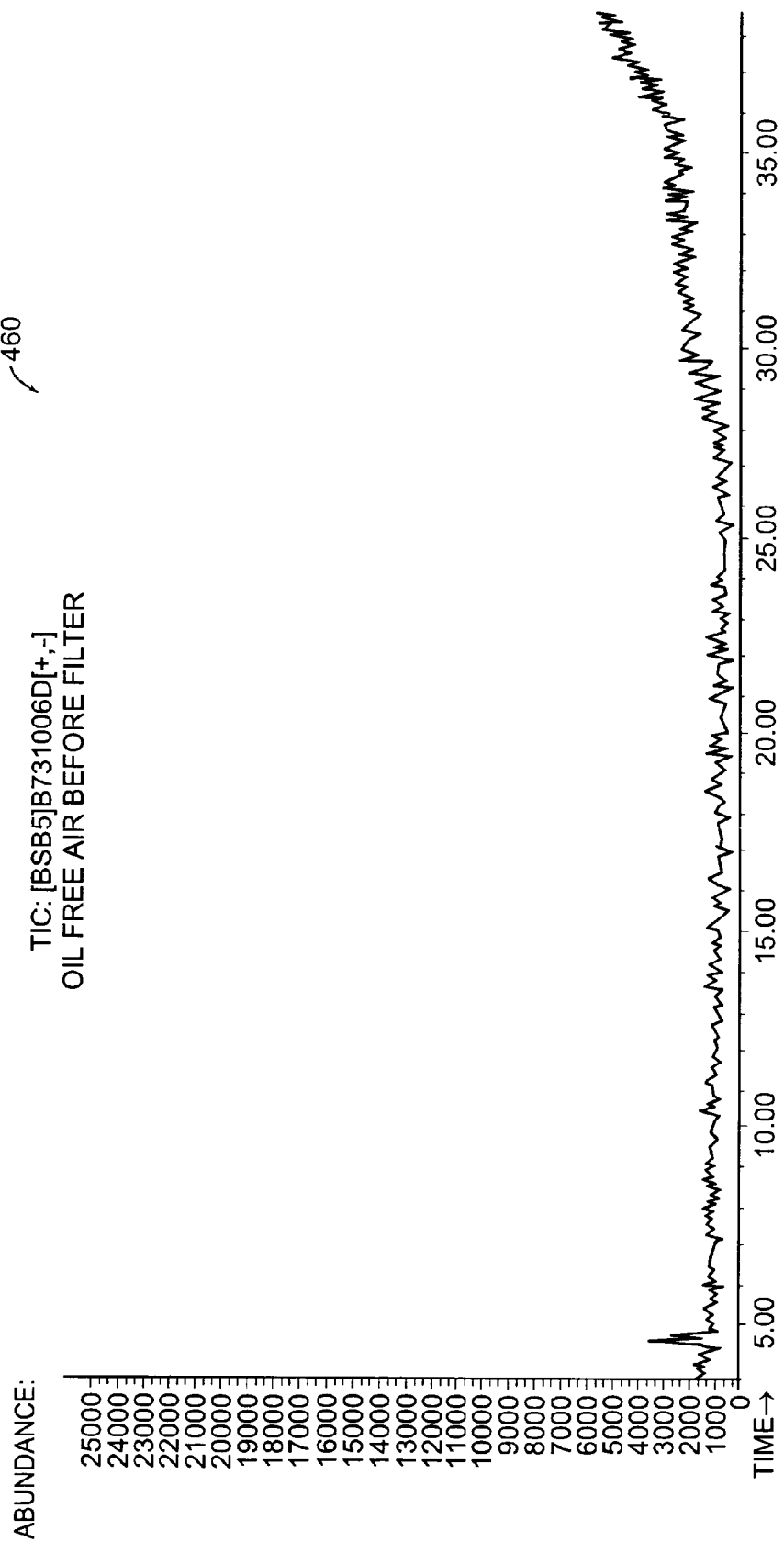
FIG. 14 is a graphical illustration of a chromatogram of a sample of oil free air sampled at a location prior to a filter in accordance with a preferred embodiment of the present invention.

FIG. 14 is a graphical illustration of a chromatogram of a sample of oil free air before a filter in accordance with a preferred embodiment of the present invention.

Table 7 lists the mass spectrometry results for oil free air sampled downstream of the filter.

TABLE 7

| Compound | Concentration, ug/m3 (as toluene) | as hexadecane |
|---|---|---|
| Silane, Dimethoxydimethyl | 2.3 | 0.9 |
| Silane, Trimethoxymethyl | 1.3 | 0.5 |
| Total | 3.6 | 1.4 |

Figure 15:
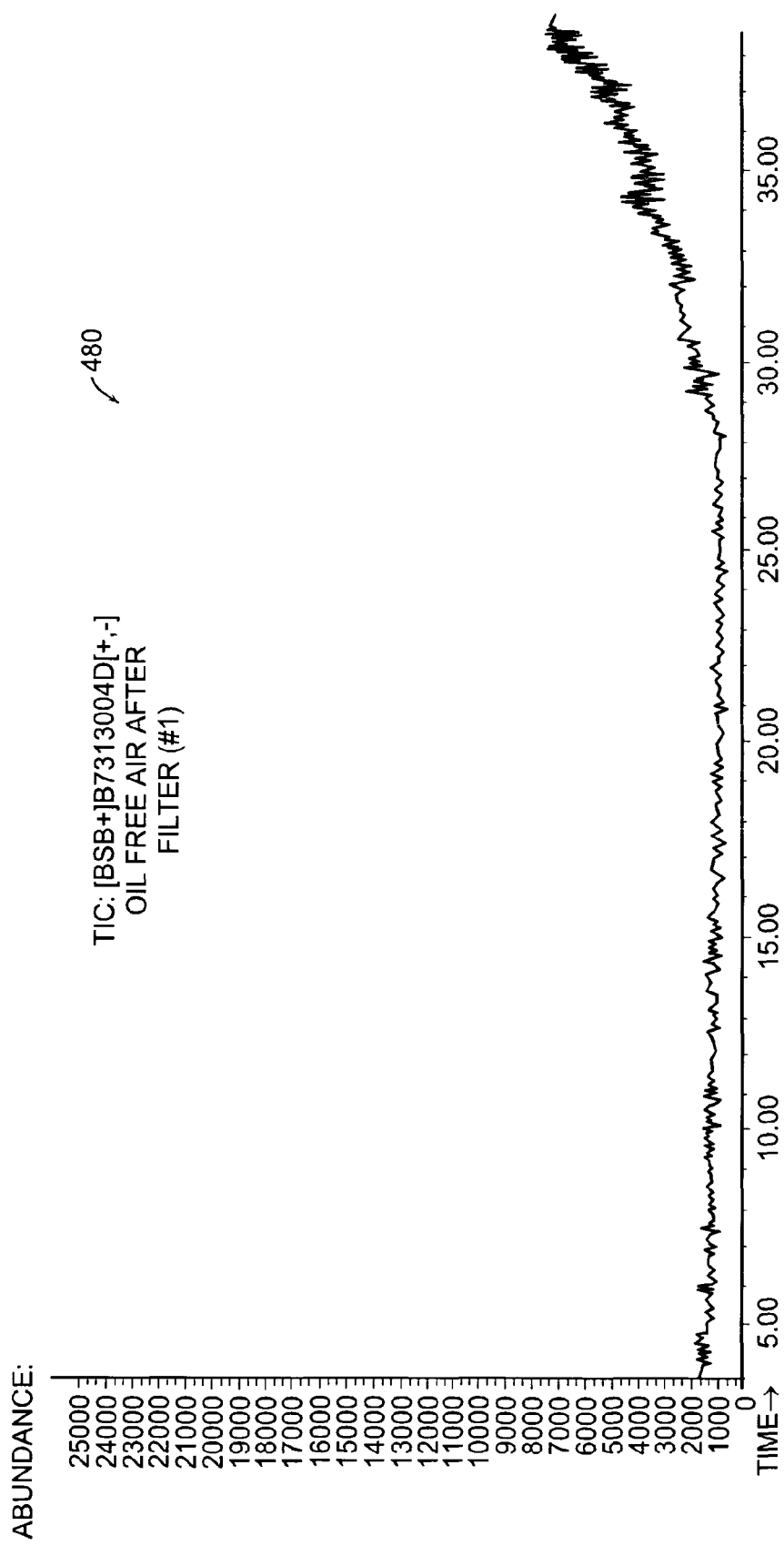
FIG. 15 is a graphical illustration of a chromatogram of a sample of oil free air sampled at a location after the filter in accordance with a preferred embodiment of the present invention.

FIG. 15 is a graphical illustration of a chromatogram of a sample of oil free air downstream of the filter in accordance with a preferred embodiment of the present invention.

Table 8 lists the mass spectrometry results for nitrogen facilities upstream of the filter.

TABLE 8

| Compound | Concentration, ug/m3 (as toluene) | as hexadecane |
|---|---|---|
| Silane, Dimethoxydimethyl | 0.8 | 0.3 |
| Silane, Trimethoxymethyl | 0.3 | 0.1 |
| Total | 1.1 | 0.4 |

Figure 16:
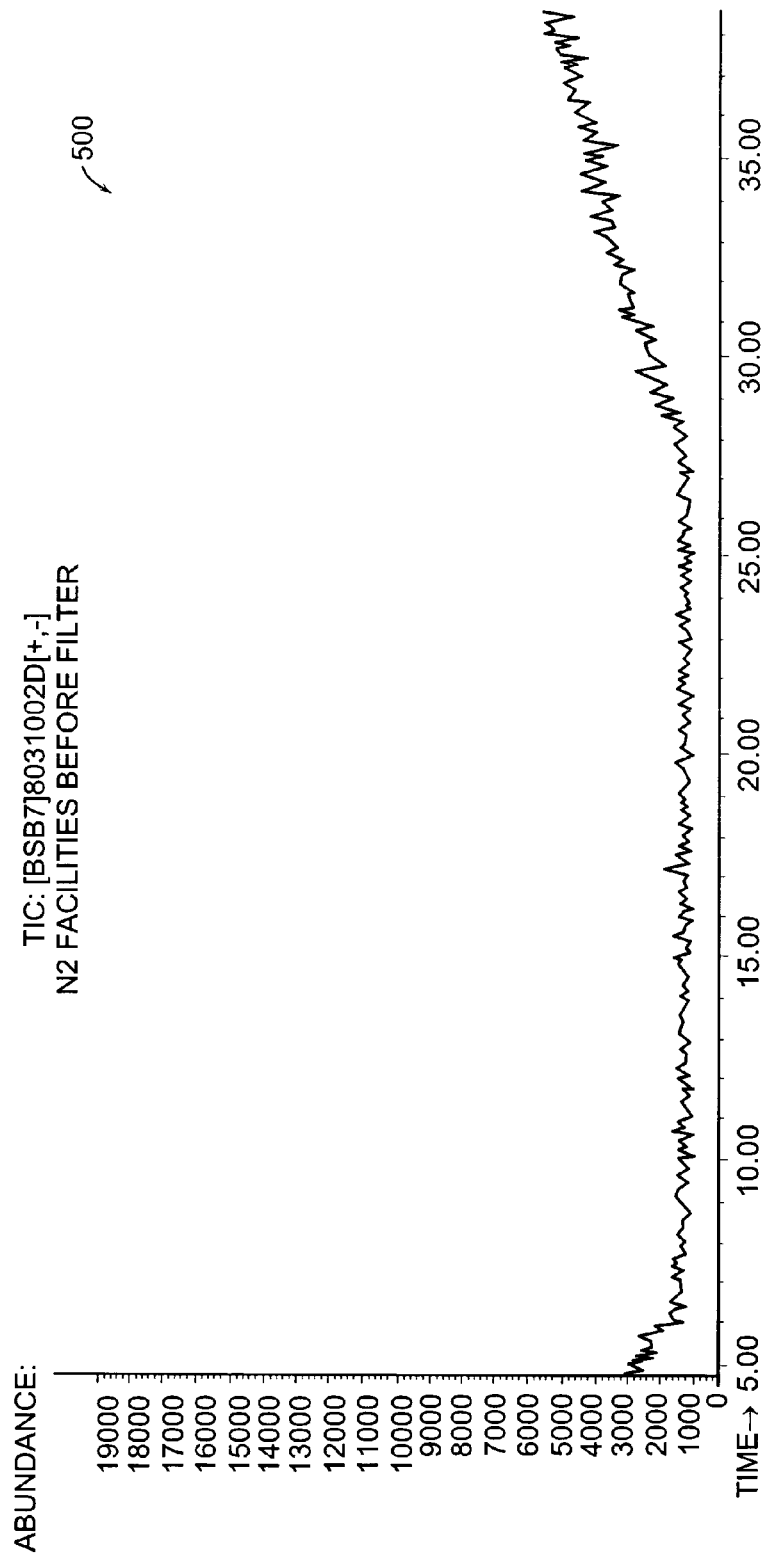
FIG. 16 is a graphical illustration of a chromatogram of a sample of nitrogen gas sampled at a location prior to a filter bed in accordance with a preferred embodiment of the present invention.

FIG. 16 is a graphical illustration of a chromatogram of a sample of nitrogen gas upstream of a filter in accordance with a preferred embodiment of the present invention.

Table 9 lists the mass spectrometry results for nitrogen downstream of the filter.

TABLE 9

| Compound | Concentration, ug/m3 (as toluene) | as hexadecane |
|---|---|---|
| Silane, Dimethoxydimethyl | 0.9 | 0.4 |
| Total | 0.9 | 0.4 |

Figure 17A:
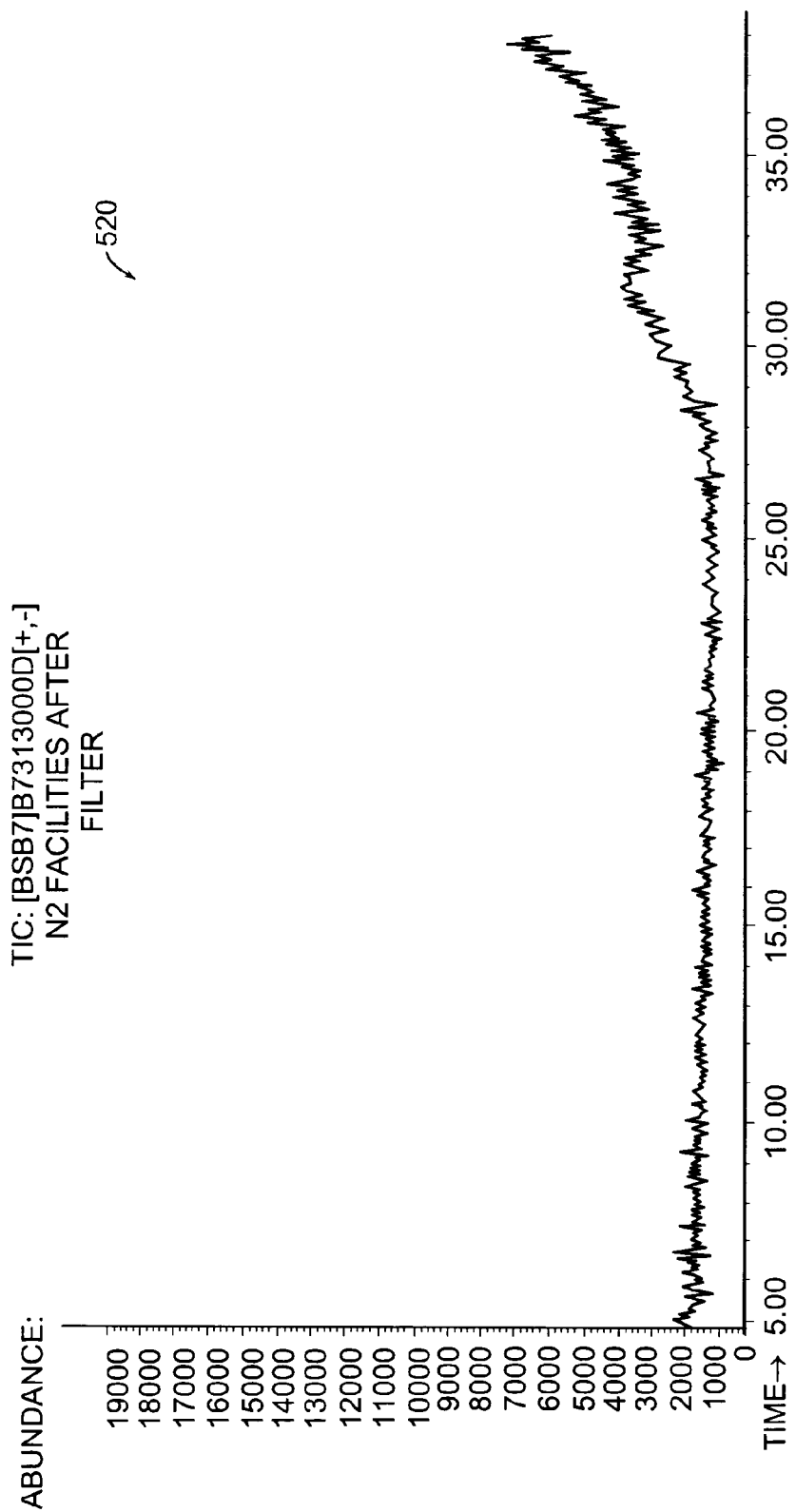
FIGS. 17A and 17B graphically illustrate a chromatogram of a sample of nitrogen gas sampled after the filter system and an average ion scan of the end of the spectra, respectively, in accordance with a preferred embodiment of the present invention.
Figure 17B:
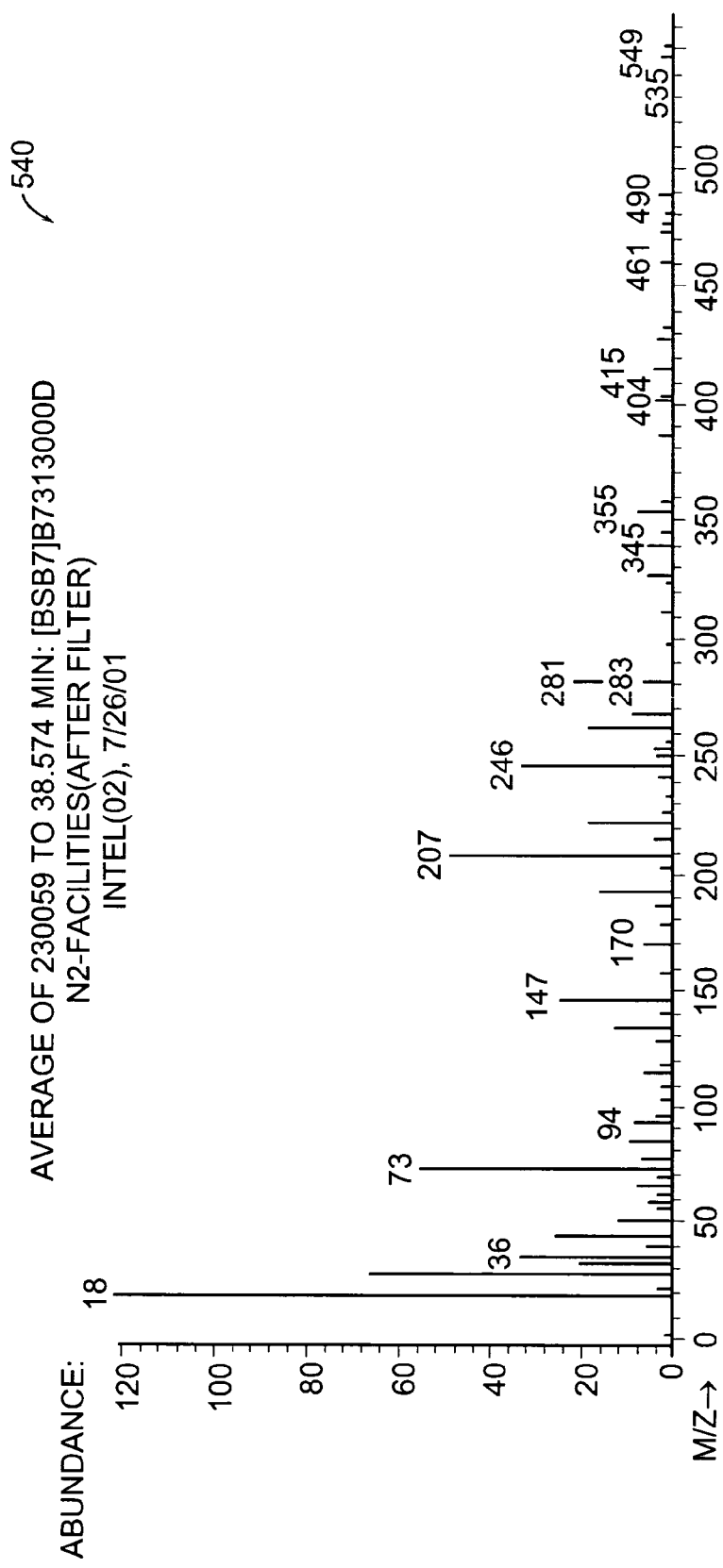

FIGS. 17A and 17B graphically illustrate a chromatogram of a sample of nitrogen gas downstream the filter system and an average ion scan of the end of the spectra, respectively, in accordance with a preferred embodiment of the present invention.

Figure 18:
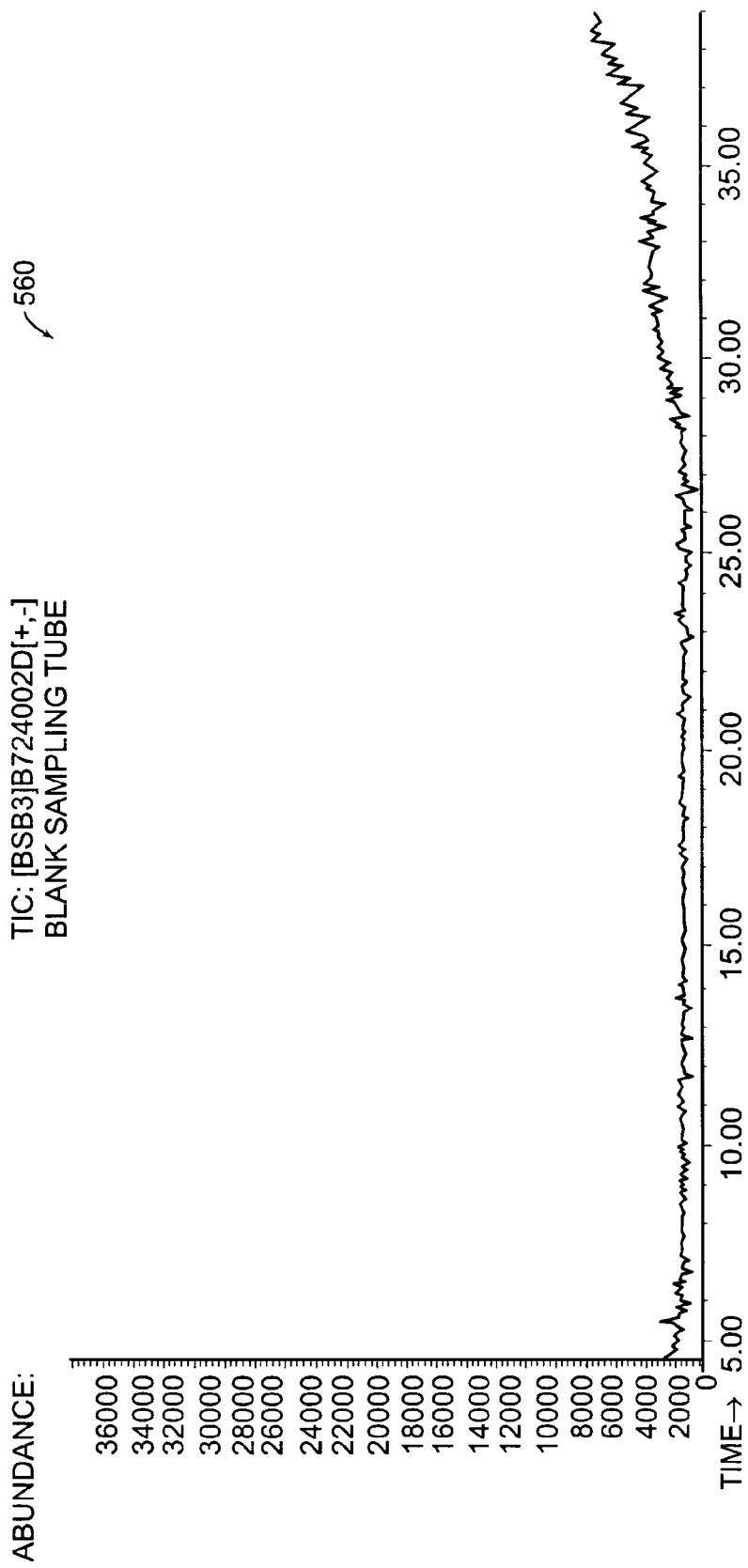
FIG. 18 graphically illustrates a chromatogram of a empty sampling tube in accordance with a preferred embodiment of the present invention.

FIG. 18 graphically illustrates a chromatogram of a blank sampling tube in accordance with a preferred embodiment of the present invention.

Figure 19:
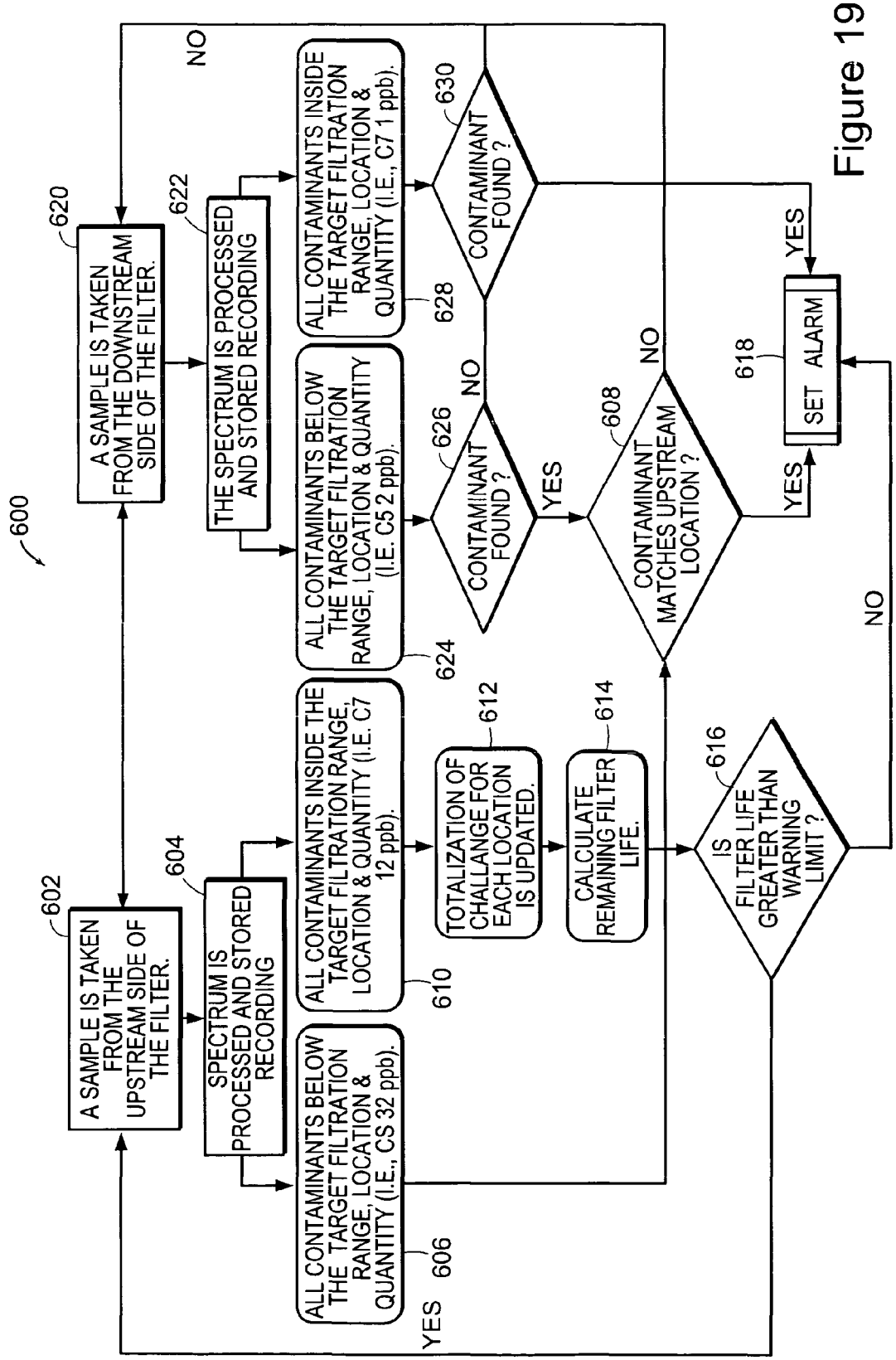
FIG. 19 is a flow chart of a method for on-line, real-time monitoring of the performance of a filter system in accordance with a preferred embodiment of the present invention.

FIG. 19 is a flow chart of a method 600 for on-line monitoring of the performance of a filter system in accordance with a preferred embodiment of the present invention. The real-time monitoring system for the performance of the filter system includes taking a sample of the airstream upstream of the filter system per step 602. The spectrum, for example, a chromatogram of the airstream is generated and stored per step 604. A threshold target range, in terms of, but not limited to, compounds and quantity, for example, $C_5$, 32 ppb, is determined. In step 606, all contaminants below the target filteration range, location and quantity are identified. In step 608, it is determined if the contaminants match those present in the upstream sampling location. If it is determined that there is no match, then another sample is taken at the location and the process iterated. However, if the contaminant level matches the threshold range upstream of the filter then an alarm is set per step 618, indicating a breakthrough condition for the particular compound.

Per step 610, for contaminants within the threshold target filtration range, location and quantity, for example, $C_7$, 12 ppb are identified from the spectrum. The total challenge for each location is updated in step 612 and the remaining filter life is calculated in step 614.

The remaining filter life is compared to a predetermined warning limit in step 616. If the filter life is not greater than the warning limit then the alarm is set per step 618. However, if the filter life is greater than the warning limit then the process is iterated again by taking a sample in step 602 and progressing through the method described herein.

These steps in accordance with the method are iterated for samples taken at different locations such as, but not limited to, a location downstream of the filter, at locations in the filter bed or within an interstack filter configuration including filter beds in a series configuration.

The target range in preferred embodiments can include variables such as amplitude of the peaks in a spectrum indicative of the concentration of the compounds, or fast moving compounds through the filter system indicative typically of low molecular weight compounds. In an alternate embodiment a mixture of species may be used as a determinant to monitor filter life and performance or combinations of variables to analyze the efficacy of the filteration system based on a parametric analysis.

Figure 20:
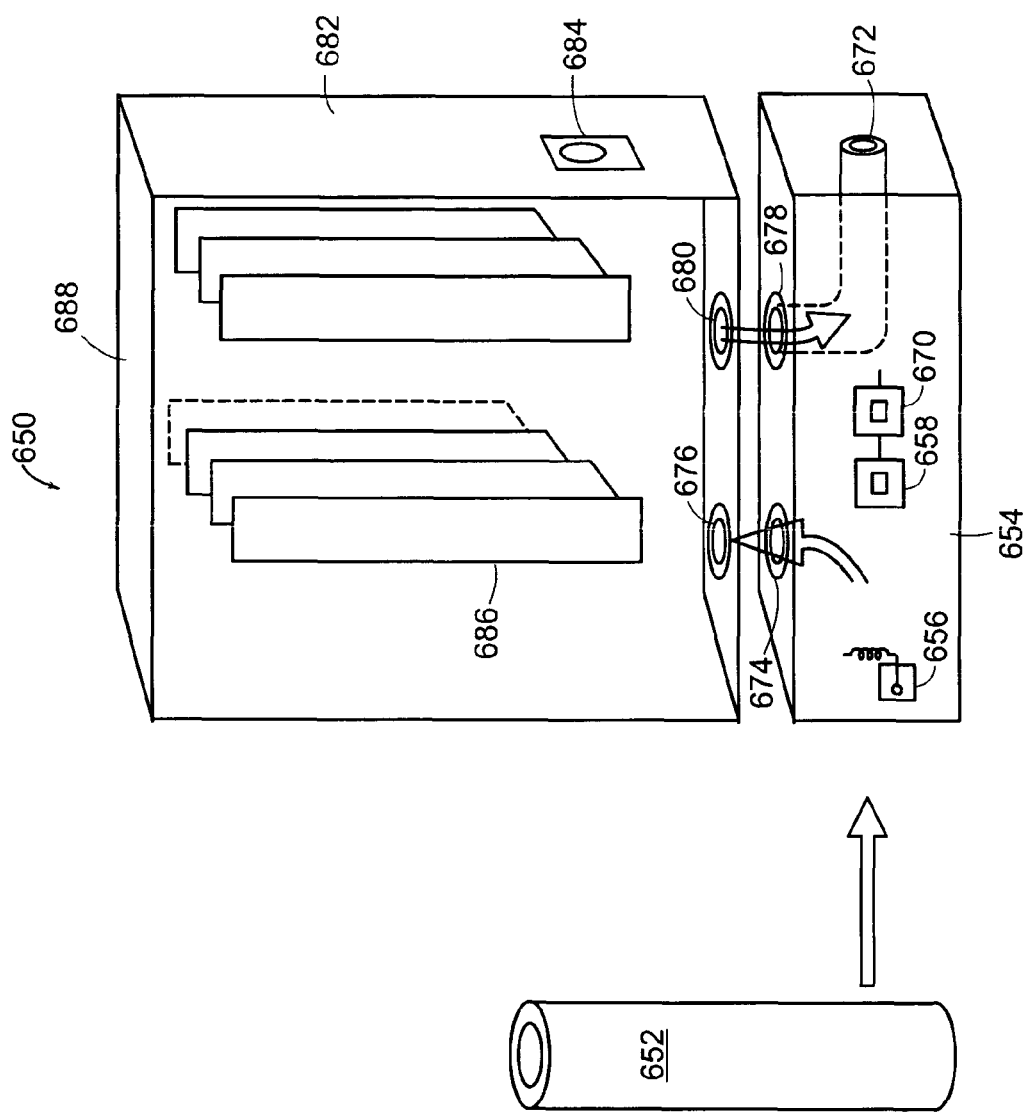
FIG. 20 illustrates a schematic block diagram of a system using a system for determining and monitoring contaminants and performance of a filter system in accordance with a preferred embodiment of the present invention.

FIG. 20 illustrates a schematic block diagram of a system for determining and monitoring contaminants and the performance of a filter system in accordance with a preferred embodiment of the present invention. The system 650 includes a clean dry air filter 652 upstream of the system, a base module 654 and a module 682 having a plurality of filters or refractory traps. The base module provides an interface to the filter module 682 and includes a pressure regulation device 656 proximate to the inlet interface 674. The outlet interface 678 is in communication with the outlet interface of the filter module 682 and the exhaust of the system 672. The exhaust interface 672 can also, in alternate embodiments, be coupled to a vacuum system if evacuation of the system for determining contamination is required. All the inlet and outlet interfaces have sealed surfaces for environmental isolation. The base module 654 further includes a controller/processor 658 such as a proportional integral controller and a control module 670 in preferred embodiments. A preferred embodiment includes electronically controlled valves to impose a duty cycle for sampling per filter cartridge. The duty cycle can be programmable. The electronically controlled valves assist in embodiments having high concentrations of impurities as they can address the potential of overload.

The filter module 682 includes a plurality of filter traps or cartridges 686 and an adequate valving arrangement in the interfaces between the cartridges to allow accurate directional flow between filters and post-collection sampling and analysis at a plurality of sites. The post-collection analysis provides quantitative and qualitative measures of the contamination present in an airstream in the semiconductor processing environment. Analysis tools such as, for example, GCMS or GCFID can be used to detect the contaminants. It may also provide for monitoring of the performance of the filter system.

In a preferred embodiment, the filter module can also include a timer device, for example, a battery powered clock to determine a sampling duration commensurate with predetermined control parameters. A manifold 688 in the filter module provides for flow between the plurality of filters. The manifolds have mechanical interfaces such as adequate beveling to help in the insertion of the filter cartridges. In a preferred embodiment the channels in the filter module can accommodate filter blanks or trap blanks which eliminate measurement errors.

In alternate embodiments the analysis system can be cooled using a thermoelectric cooling device. Organics can be condensed and collected using the low temperature embodiment. A fewer number of traps are required for the low temperature embodiment since the organics can be collected post condensation. An embodiment of the low temperature system can include heat sinks to dissipate the heat energy generated.

Alternate embodiments include safety devices coupled to external interface connections in the event pressure is lost. This obviates sampling inaccuracies.

Figure 21:
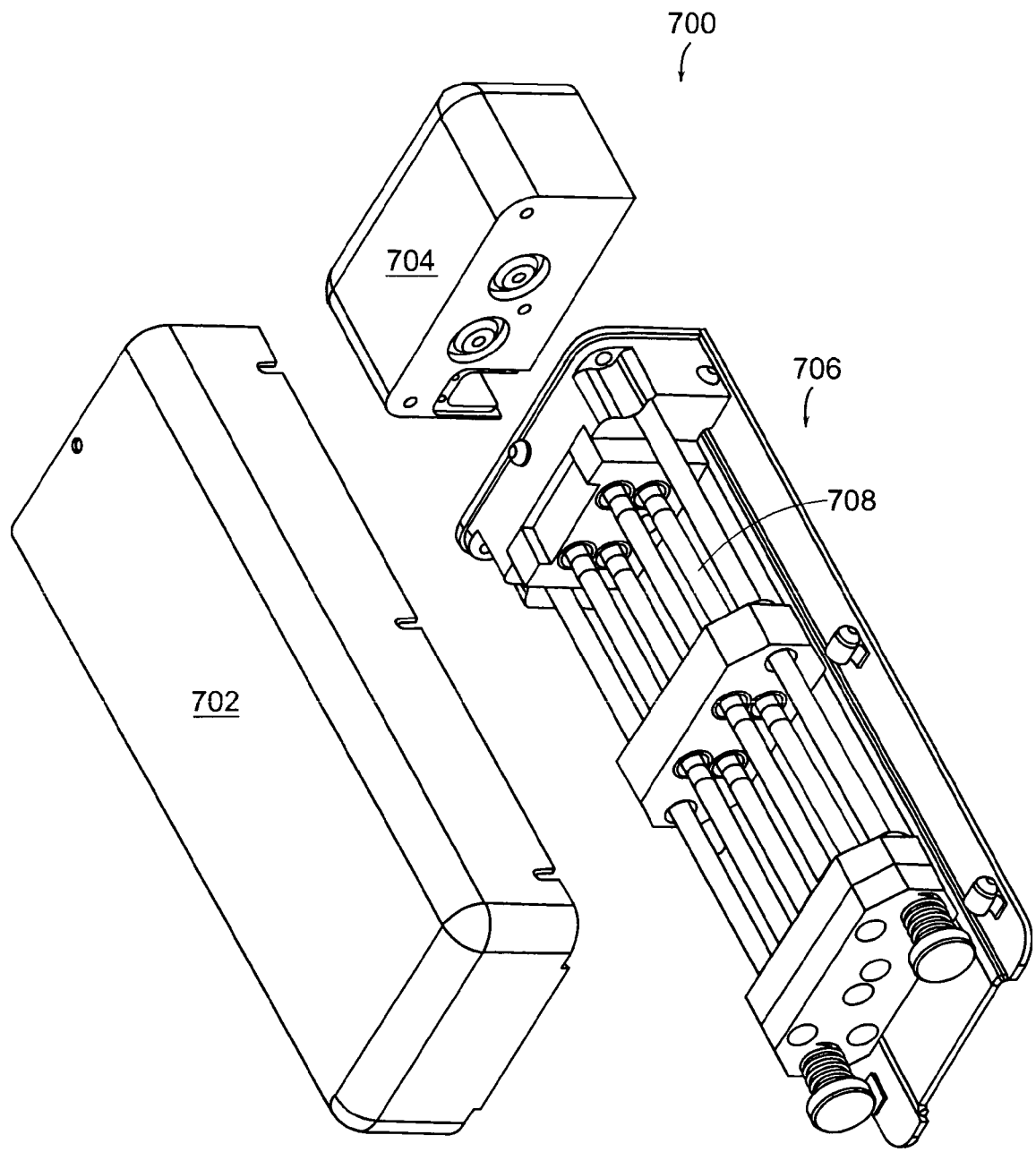
FIG. 21 illustrates a schematic diagram of system modules in accordance with a preferred embodiment of the system for determining and monitoring contaminants and the performance of a filter system of the present invention.

FIG. 21 illustrates a schematic diagram of the modules in accordance with a preferred embodiment of the system for detecting and monitoring contaminants and the performance of a filter system of the present invention. A cover 702 is placed over the base module 704 and the filter module 706. The filter module 706 includes a plurality of filter cartridges 708 as described with respect to FIG. 20.

Figure 22:
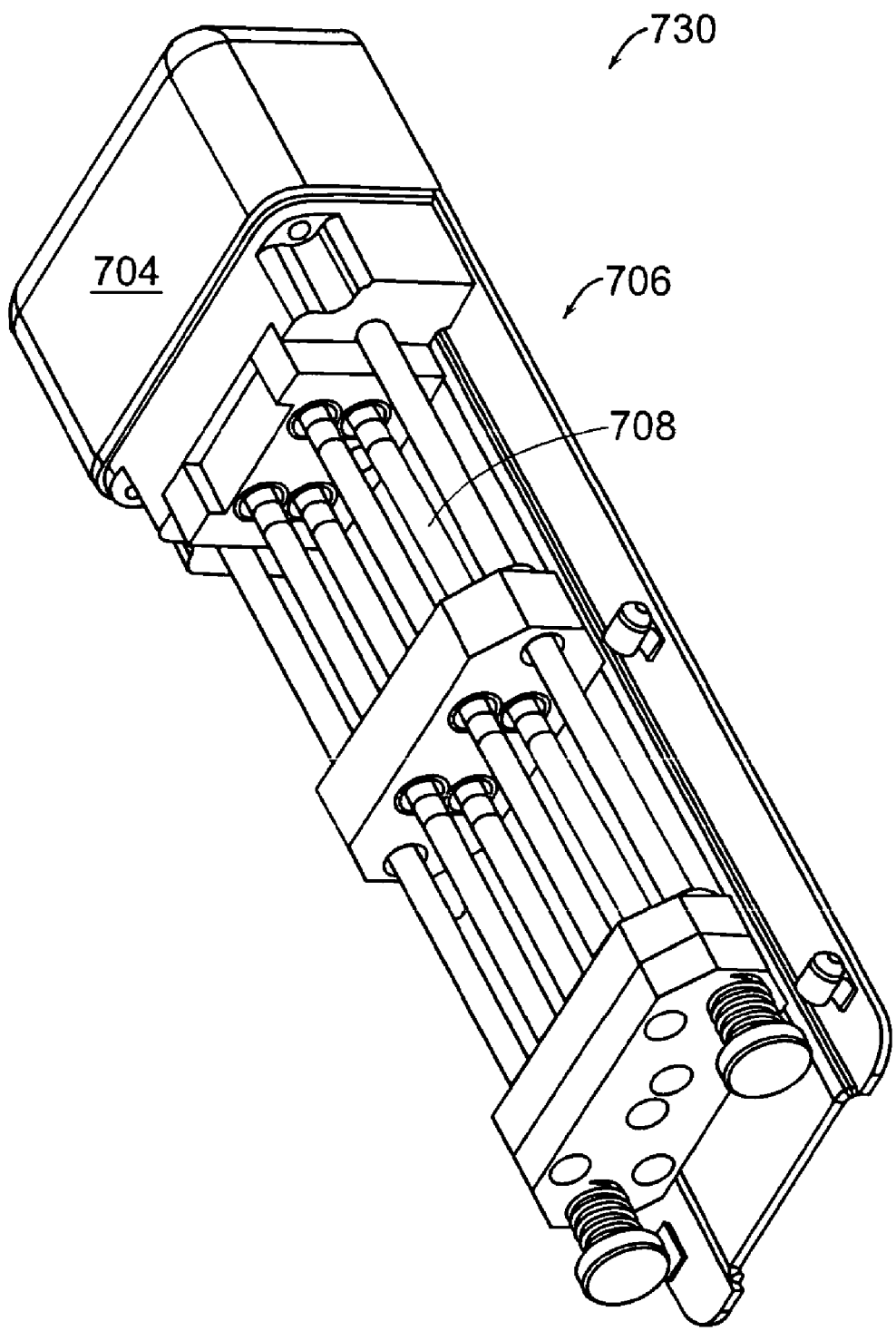
FIG. 22 illustrates a schematic diagram of a module having a plurality of filter traps of the system shown in FIG. 20 in accordance with a preferred embodiment of the present invention.

FIG. 22 illustrates a schematic diagram of a module having a plurality of filter traps of the detection system in accordance with a preferred embodiment of the present invention. The base module 704 is illustrated as being coupled to the filter module 706 as discussed with respect to FIG. 20.

Figure 23:
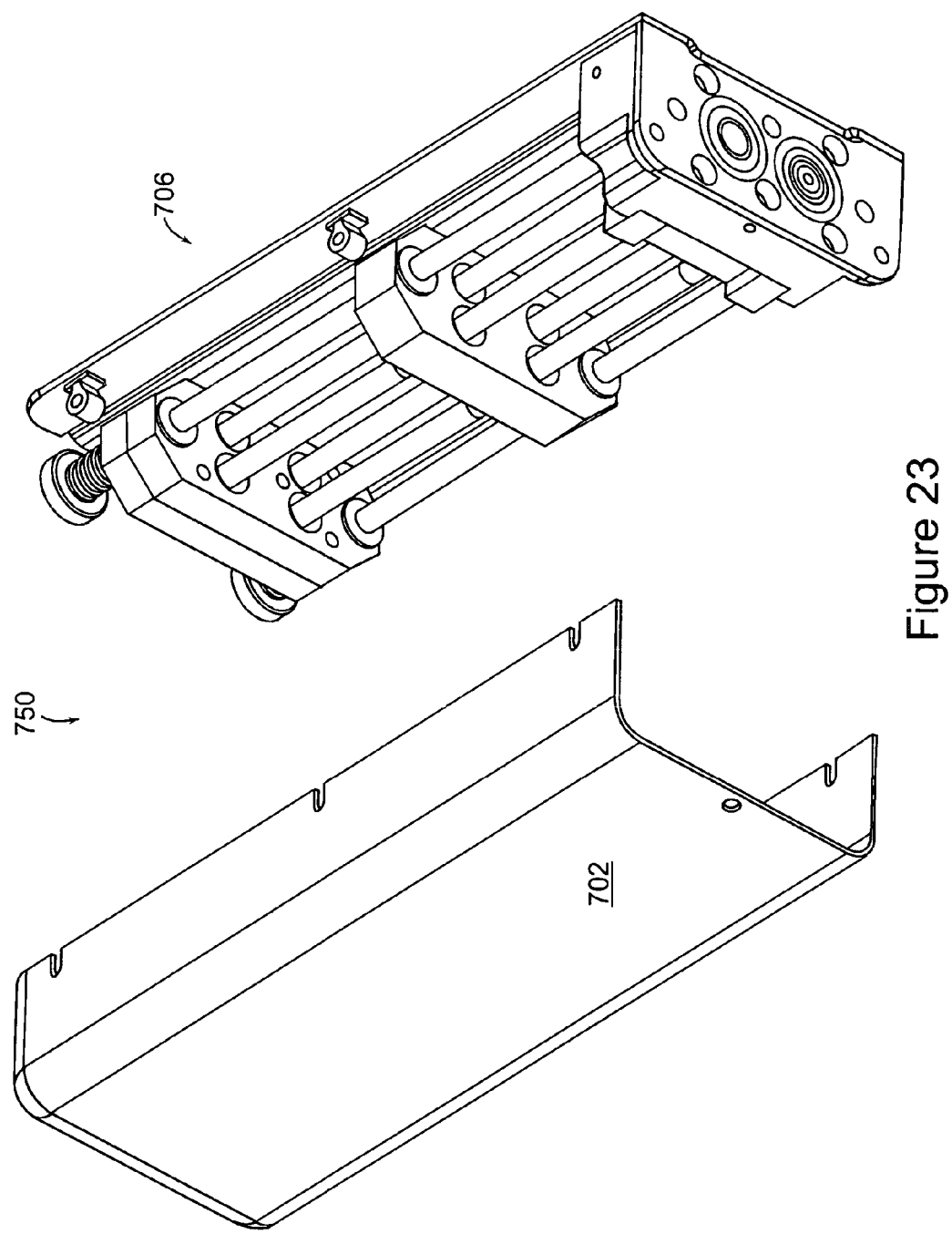
FIG. 23 illustrates an alternate view of the module having a plurality of filter traps as shown in FIG. 21.

FIG. 23 illustrates an alternate view of the module having a plurality of filter traps as shown in FIG. 21.

Figure 24:
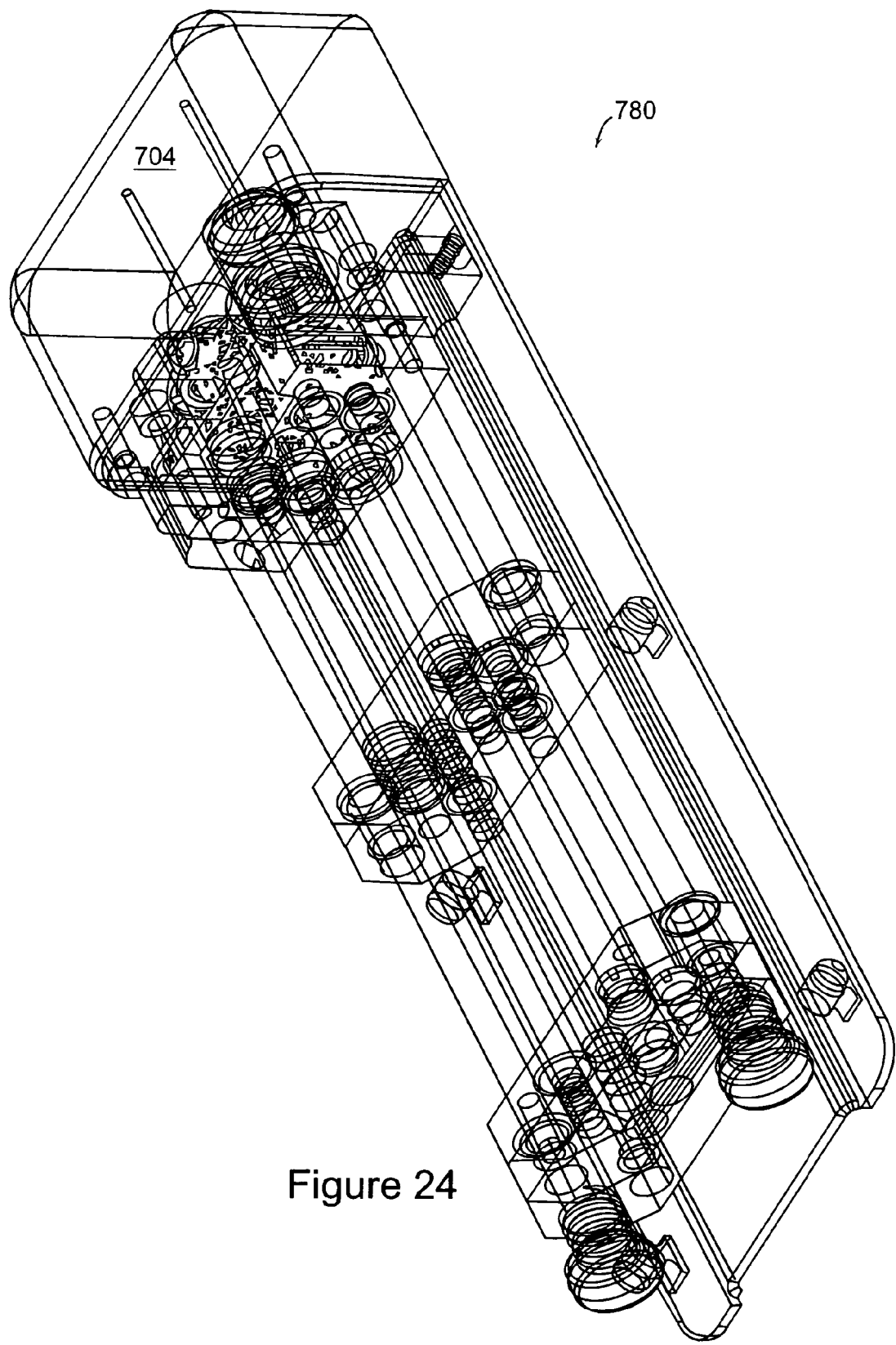
FIG. 24 illustrates a detailed view of the module having a plurality of filter traps as shown in FIG. 21 along with the plumbing in the manifolds in accordance with a preferred embodiment of the present invention.

FIG. 24 illustrates a detailed view of the module having a plurality of filter traps as shown in FIG. 21 along with the plumbing in the manifolds in accordance with a preferred embodiment of the present invention.

Figure 25B:
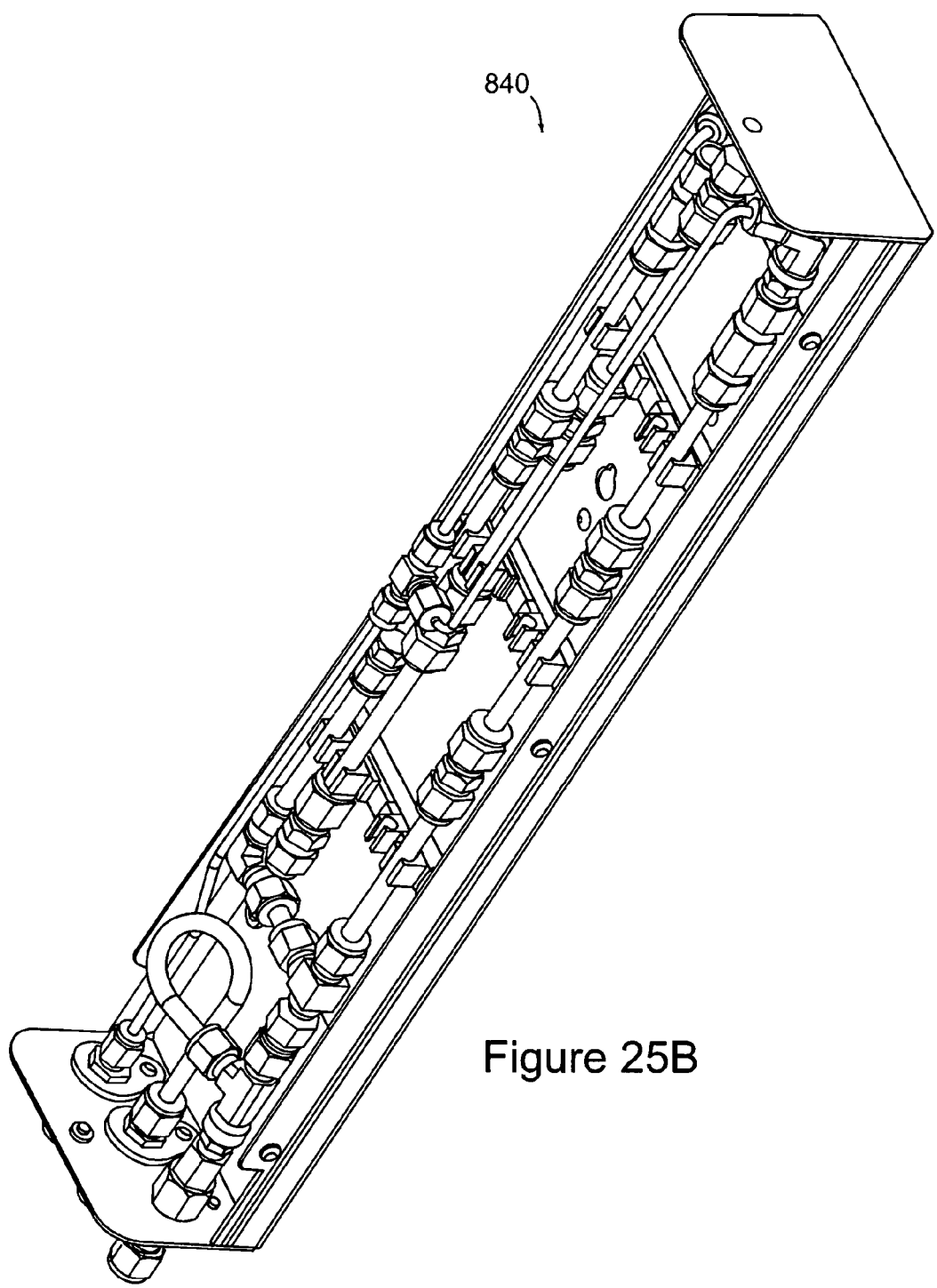
Figure 25C:
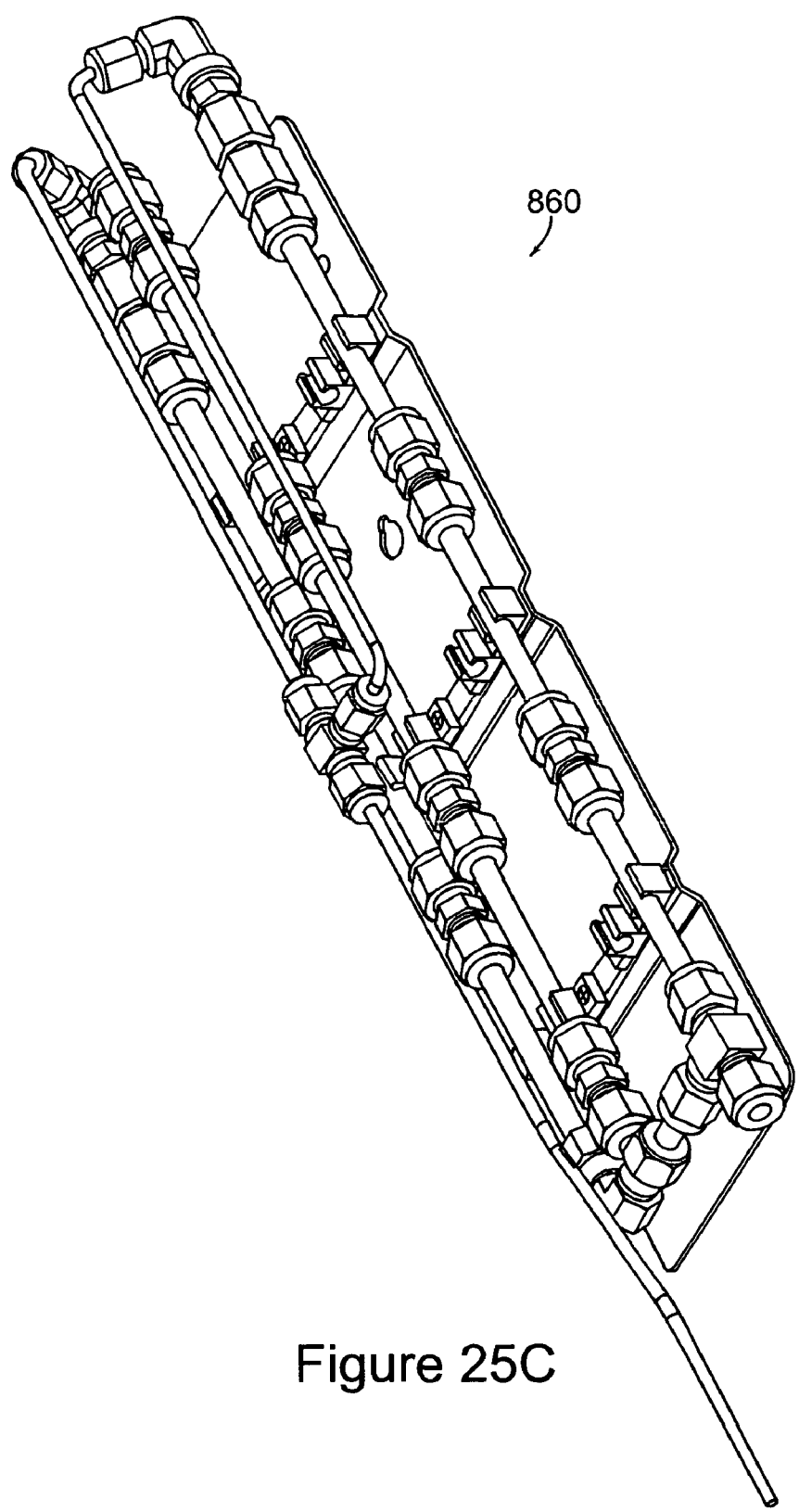

FIGS. 25A–25C illustrate schematic diagrams of a device that functions as a concentrator in a contaminant and filter monitoring system as it increases the sensitivity of collection in accordance with a preferred embodiment of the present invention. The concentrator device 804 has a cover 802 and is inserted in a manifold, for example, manifold 806 that has the inlet and outlet interfaces. The filter system including a filter monitoring functionality can be reduced in size using a coupling device such as, for example, the concentrator 804. A greater volume can be collected in the filter system if the temperature is reduced, for example, to 0° C. or below. The sensitivity of data collection is also increased by the use of the concentrator device that includes absorptive materials such as, for example, Tenax® T.A. High boilers, such as, for example, organics having six carbon atoms or more are absorbed by Tenax® T.A. In the alternative, absorptive materials such as, for example, carbon traps such as supplied by, for example, Supelco can be used in embodiments including low boilers. Alternate embodiments include a combination of the filters for high and low boilers which can be arranged in parallel and/or in series.

Figure 26A:
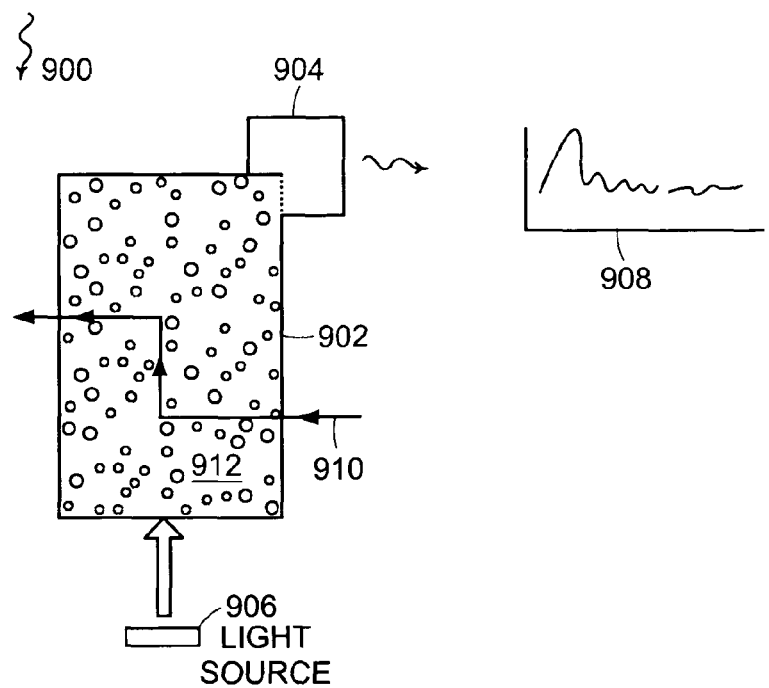
FIGS. 26A and 26B illustrate schematic block diagrams of a detection system that emulates and detects a deposition process on optical elements in accordance with a preferred embodiment of the present invention.
Figure 26B:
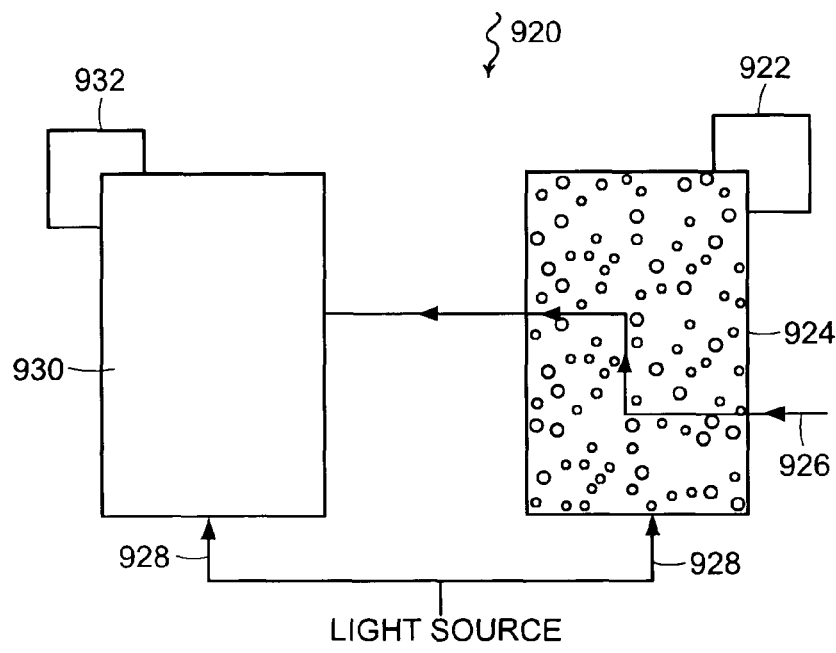

FIGS. 26A and 26B illustrate schematic block diagrams of a system that emulates and detects a deposition process on optical elements in accordance with a preferred embodiment of the present invention. As described hereinbefore, photochemical deposition reactions occur when high-energy photons interact with organic vapors. These reactions form extremely reactive free radicals which may form larger organic compounds can contaminate optical elements. A polymer layer may be formed on the optical surfaces and contaminate the optical elements. A preferred embodiment includes a detection system that emulates the deposition process of organic compounds on optical surfaces. A filter cartridge 902 filled with a glass pack such as, for example, glass beads 912 emulates the optical materials. Compressed, clean dry air 910 is passed through the filter cartridge. A light source 906 provides light, for example, a laser providing laser light energy to the cartridge to cause the formation of a polymer film on the surfaces of the glass beads as high energy photons react with organic vapors in the trap.

The photodetector includes a photocell 904 to measure the energy level of light, which is altered based on the deposition of contaminants on the surfaces of the multitude of glass beads. The glass beads provide for a larger surface area for deposition. The spectral and transmission differences are monitored to determine the level of contamination. This embodiment provides a prospective method to determine damage that can occur on the optical elements such as, for example, the optics in the stepper. Measures can then be taken to counter the potential damage to valuable optics.

It should be understood that the programs, processes, methods and systems described herein are not related or limited to any particular type of collection media, or computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams. While various elements of the preferred embodiments have been described as being implemented in software, other embodiments in hardware or firmware implementations may be used, and vice-versa.

It will be apparent to those of ordinary skill in the art that methods involved in the system and method for determining and controlling contamination may be embodied in a computer program product that includes a computer usable medium. For example, such a computer usable medium can include a readable memory device, such as, a hard drive device, a CD-ROM, a DVD-ROM, or a computer diskette, having computer readable program code segments stored thereon. The computer readable medium can also include a communications or transmission medium, such as, a bus or a communications link, either optical, wired, or wireless having program code segments carried thereon as digital or analog data signals.

In another aspect, the present invention provides systems, apparatuses and methods for passive monitoring of contamination in a semiconductor processing system using passive samplers and sampling instead of active sampling. As used herein, "active sampling" refers to the use of air moving device which utilizes an external source of energy coupled to the sampling system to deliver a gas sample to a collection material of a collection device of the sampling system. In comparison, passive sampling uses the energy of the gas sample itself to deliver a gas sample to a collection material of a collection device, for example, by diffusion.

Typically, passive sampling has been considered inadequate for monitoring contamination in a semiconductor processing system because of the generally very low sample delivery rates associated with passive sampling. For example, for a system which may have a sample delivery rate of 0.1 liters/min. with active sampling, can have a sample delivery rate of only 0.0001 to 0.001 liters/min. In another example, for active sampling using a hand held pump to pull air through a Tenax® TA tube at a flow rate of 0.150 liters/min., the diffusive flow rate is 0.0003 liters/min for passive sampling. As a result, passive sampling at a flow rate of 0.0003 liters/min. typically needs to be conducted for over 83 days to achieve the same total sampling volume of active sampling at a flow rate of 0.150 liters/min for 4 hours. Accordingly, passive sampling has generally been viewed as inadequate for monitoring trace contaminants (for example, contaminants with a concentration less than about 10 ppb) because of the long sampling duration needed to sample a volume of contaminant comparable to that collected by active sampling.

Active sampling, however, has several disadvantages. Active sampling requires an external source of energy for the active sampling system, which may limit the number and placement of such active systems in, for example, a semiconductor processing facility or system. In addition, by requiring a source of power active systems are susceptible to failure due to power outages or breakdown of the external source of energy, such as, for example, a pump. In comparison, a passive sampling system, in accordance with a preferred embodiment of the present invention, is typically unaffected by power outages and there is no external source of energy for the sampling system which can breakdown.

Other disadvantages of typical prior art active sampling approaches, which use a pump as an active source of energy, include, for example: calibration of multiple devices (such as, for example, the pump, flow meters, and timers); pump vibration; and the need for trained system operators.

In comparison, in a passive sampling system, in accordance with a preferred embodiment of the present invention, only one parameter, the flow rate, is calibrated. In another embodiment, of the present invention, a sampling duration time is calibrated, but no flow parameters are calibrated. In addition, in accordance with a preferred embodiment of the passive sampling system of the present invention, the passive system substantially operates on its own without the need for constant operator oversight.

Figure 27:
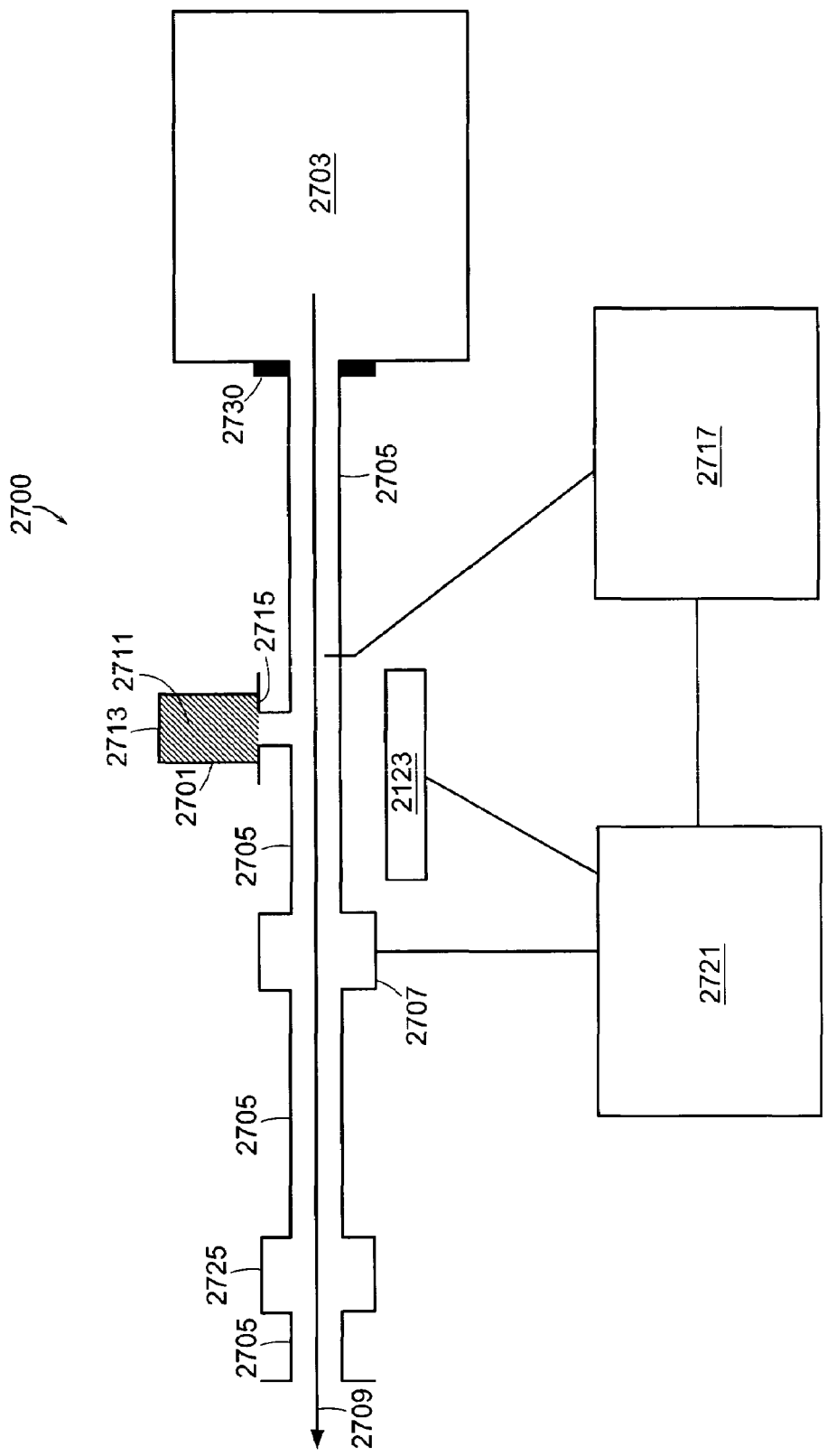
FIG. 27 is a schematic illustration of a passive sampling system in accordance with various embodiments of the present invention.

In one aspect, the present invention provides passive sampling systems for monitoring contaminants in a semiconductor processing system. Referring to FIG. 27, in one embodiment, that passive sampling system 2700, comprises a collection device 2701 in fluid communication with a sample line 2705 which in turn is in fluid communication with a semiconductor processing system 2703. A flow regulator 2707 can be disposed in the sample line 2705 to regulate a flow of gas 2709 out of the semiconductor processing system 2703. In one embodiment, the semiconductor processing system comprises a photolithography instrument. The flow of gas 2709 can arise for example, from semiconductor processing system over pressure.

In accordance with a preferred embodiment, the semiconductor processing system comprises a photolithography cluster tool, such as for example, an exposure tool, used in manufacturing semiconductor devices, that is sensitive to molecular contamination and a filtering system which removes the molecular contamination which may include volatile and semi-volatile or condensable organic substances, which, if present, can cause contamination of optical elements via series of homogeneous and/or heterogeneous ultraviolet (UV) induced processes.

The collection device 2701 contains an absorptive material 2711 to collect one or more contaminants from the flow of gas 2709. The collection device 2701 is sealed at the end distal 2713 to the sample line 2705. The proximal end 2715 of the collection device 2701 is in fluid communication with the sample line 2705 such that the absorptive material 2711 is capable of receiving one or more contaminants from the flow of gas 2709 by a passive transport process, such as, for example, diffusion. In a preferred embodiment, one or more contaminants reach the absorptive material substantially by diffusion from the flow of gas. For example, in one embodiment, the collection device comprises a ¼" diameter by 3" long Tenax®) tube, which is connected to he sample line by a Swagelok® fitting. The ¼" diameter by 3½" long Tenax® tube contains about 150 milligrams (mg) of adsorptive material.

In accordance with preferred embodiments, the collection device 2701 includes an amount of adsorptive material with an adsorption capacity equivalent to an amount of Tenax T.A. in the range from about 0.05 g to about 1.0 g.

In another embodiment, the sample line is positioned such that the flow of gas comprises gas from a location downstream of a filter or filter system. In another embodiment, the sample line is positioned such that the flow of gas comprises gas from a location upstream of a filter or filter system. In another embodiment, the sample line is positioned such that the flow of gas comprises gas from a location inside a filter or filter system. In one version of these embodiments, the passive sampling system is configured to monitor the condition of the filter or filter system. For example, the passive sampling system, which can comprise one or more collection devices, sampling lines etc., can be configured to sample a gas flow from a location upstream and a location downstream of a filter to assess breakthrough of a target contaminant.

In various embodiments, the passive sampling systems of the present invention further comprise a monitor system 2717 positioned to measure the temperature, the pressure, or both, of the flow of gas. Preferably, the monitor system 2717 measures the temperature and pressure of a region adjacent the proximal end 2715 of the collection device 2701. In one embodiment, the monitor system 2717 measures the temperature and pressure of a region adjacent to the flow regulator 2707, inside the flow regulator 2707, or both.

In various embodiments, the passive sampling systems of the present invention further comprise a regulator system 2721 positioned to regulate the temperature, the pressure, or both, of the flow of gas. Preferably, the regulator system 2721 regulates the temperature, the pressure, or both, of the flow of gas at least in a region adjacent the proximal end 2715 of the collection device 2701. In one embodiment, the regulator system 2721 regulates the temperature and pressure of a region adjacent to the flow regulator 2707, inside the flow regulator 2707, or both.

The regulator system 2721 can comprise, for example, a heating/cooling device 2123 proximate to or in contact with, for example, the sample line 2705. Examples, of suitable heating/cooling devices include, but are not limited to, thermoelectric devices.

In various embodiments, the regulator system regulates temperature, pressure, or both, based at least in part on measurements provided by a monitoring system. For example, a regulator system 2721 can send a signal to a heating/cooling device 2123 based on a temperature measured by the monitor system 2717 to bring the temperature of the gas flow in a region of the sample line 2705 into a selected temperature range. In addition, the regulator system 2721 can send a signal to a flow regulator 2707 (such as, for example, a mass flow controller) based on a pressure measured by the monitor system 2717 to bring the pressure of the gas flow in a region of the sample line 2705 into a selected pressure range.

In various embodiments, the passive sampling systems of the present invention further comprise a backflow prevention device 2725 positioned in the sample line 2705 such that it is capable of substantially preventing gas flow from the sample line 2705 into the semiconductor processing system 2703. Preferably, the backflow prevention device 2725 comprises a filter positioned in the sample line such that it is capable of substantially preventing gas flow from the sample line into the semiconductor processing system. Examples of suitable backflow prevention devices include, but are not limited to, checkvalves with or without activated filter is in series.

The collection device includes absorptive material such as, for example, a refractory absorptive material. In one embodiment, glass spheres of a given size are used. In a preferred embodiment, crushed glass spheres are used. In another preferred embodiment, the absorptive material is the polymer Tenax®. For example, Tenax® has a high capacity for high boiling point compounds and operating Tenax® past low molecular weight breakthrough capacity allows the capture of high molecular weight compounds. Preferably, the absorptive material of the collection device is a material capable of collecting one or more contaminants in a molecular weight range of interest. In a preferred embodiment, the absorptive material is capable of collecting $C_6$–$C_{30}$ containing contaminants. In another embodiment, the absorptive material is capable of collecting molecular bases or/and molecular acids, and comprises, for example, a reagent treated glass fiber non-woven media.

The sample line may comprise any material suitable for conveying a gas flow from the semiconductor processing system. Suitable materials can be selected, for example, based on the known or predicted reactivity of the sample line material with known or suspected constituents in the gas flow. Suitable materials include, but are limited to, PFA, stainless steel, Ni, quartz, polytetrafluoroethylene (PTFE). Preferably, the sample line comprises a PFA tube.

It is further preferred that the internal surface of the sample line, at least in the portion between the semiconductor processing system and the collection device, is equilibrated with the flow of gas. The internal surface of the sampling line is preferably in equilibrium with the gas phase sample in order to not interfere with the contaminant collection process. For example, it is preferred that the concentration of contaminants of interest on an internal surface of the sample line are such that the internal surface of the sample line does not significantly uptake the contaminants of interest from the flow of gas. A sample line may be equilibrated, for example, by inputting a gas flow until the concentrations of one or more contaminants of interest at the input to the sample line are substantially the same as the concentrations at the output of the sample line. In another example, an approximately twenty foot long sampling line was found to be substantially equilibrated with hexadecane contaminants in typical clean room air after approximately 24–48 hours using a gas flow rate of 0.15 liter/min. of the clean room air. Although sample line equilibration tests were conducted with an approximately twenty foot line, it is preferred that the sampling line be as short as possible. In practical applications, it is believed that sample lines in the range from about one to five feet may be practical and will have correspondingly shorter equilibration times than a twenty foot line.

In addition, it is preferred that in operation the absorptive material of the passive sampling systems of the present invention is exposed to a substantially continual flow of gas from the semiconductor processing system such that the collection device samples a fresh sample of the gas. In one embodiment, the gas flow rate is in the range from about 0.3 liters/min. to about 3 liters/min. In a preferred embodiment, the gas flow rate is greater than about 1 liter/min.

The flow regulator may be any device or structure suitable for regulating the flow of gas from the semiconductor processing system. For example, the flow regulator can be a valve, a series of valves, a critical orifice or series of critical orifices, a voltage sensitive orifice or series of voltage sensitive orifices, a mass flow controller (MFC), a temperature regulated flow controller, or combinations thereof. In a preferred embodiment, the flow regulator is adapted to regulate the flow of gas to a flow rate in the range from about 0.3 liters/min. to about 5 liters/min.

In another aspect, the present invention provides passive sampling apparatus for monitoring contaminants in a semiconductor processing system. In one embodiment, referring to FIG. 27, the apparatus comprises a sample line 2705 having a portion 2730 adapted to be placed into fluid communication with a semiconductor processing system.

In accordance with a preferred embodiment, the adapted portion 2730 of the sample line is adapted to be placed into fluid communication with the semiconductor processing system comprising a photolithography cluster tool, such as for example an exposure tool, used in manufacturing semiconductor devices, that is sensitive to molecular contamination and a filtering system which removes the molecular contamination which may include volatile and semi-volatile or condensable organic substances, and/or inorganic compounds, which, if present, can cause contamination of optical elements via series of homogeneous and/or heterogeneous ultraviolet (UV) induced processes.

Suitable sample lines, collection devices, absorptive materials, flow regulators, backflow prevention devices, monitor systems, and regulator systems, for the passive sampling apparatuses of the present invention, include, but are not limited to, those discussed in the context of FIG. 27 and the passive sampling systems for monitoring contaminants in a semiconductor processing system of the present invention.

In another aspect, the present invention provides methods for passive monitoring of contaminants in a semiconductor processing system. In one embodiment, the method monitors contaminants in a filter or filter system of a semiconductor processing system.

Figure 28:
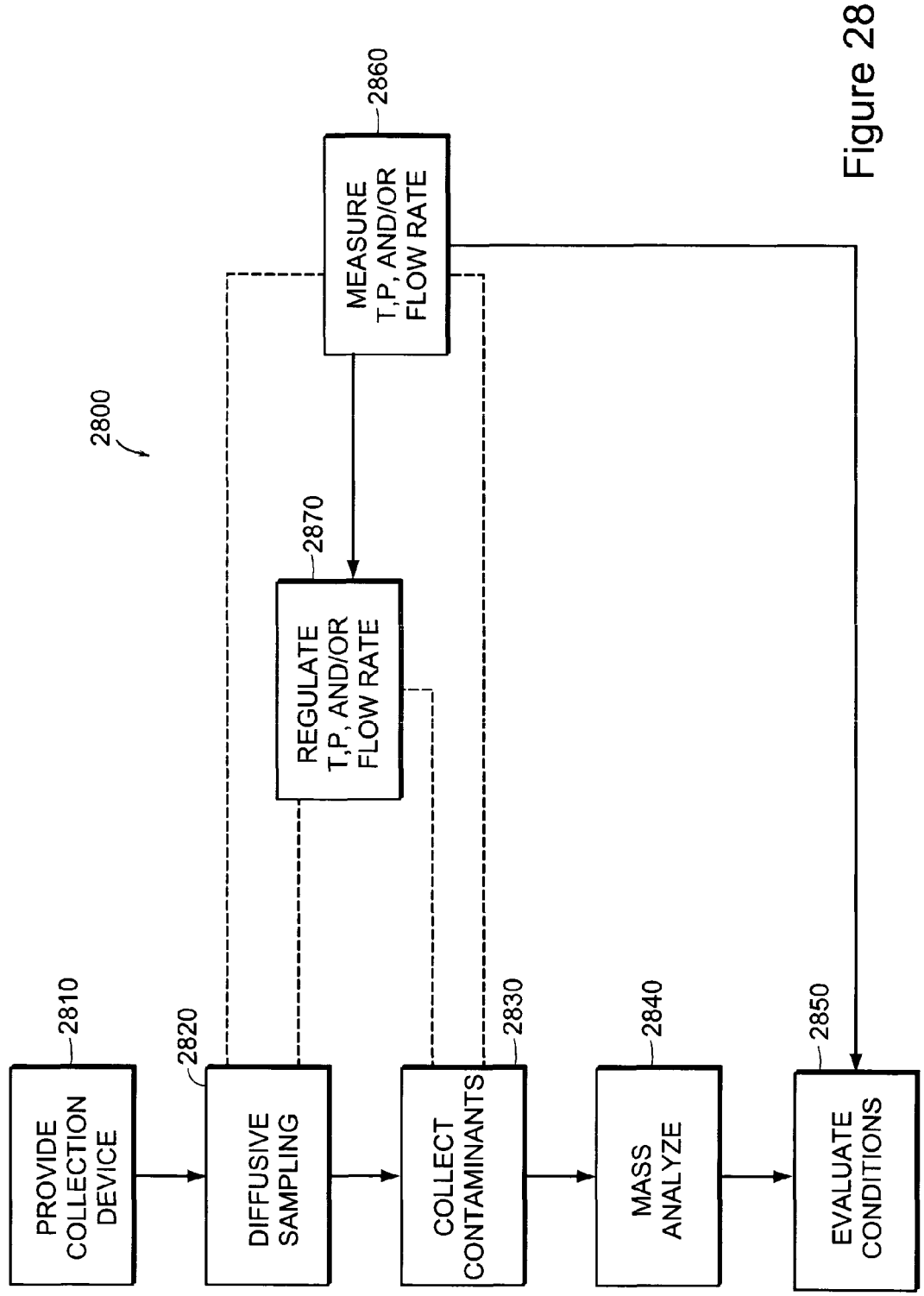
FIG. 28 is a flow chart of methods for passive monitoring of contaminants in a semiconductor processing system in accordance with various embodiments of the present invention.

Referring to FIG. 28, various embodiments of methods for passive monitoring of contaminants in a semiconductor processing system 2800 are shown. The methods provide a collection device containing an absorptive material 2810. Suitable collection devices and absorptive materials for the methods of the present invention include, but are not limited to, those discussed in the context of the passive sampling systems for monitoring contaminants in a semiconductor processing system. The methods proceed with sampling one or more contaminants by diffusion of the contaminants to the collection device 2820 from a gas or gas flow, and at least a portion of these contaminants are collected by the absorptive material 2830. In a preferred embodiment, one or more contaminants reach the absorptive material substantially by diffusion from the flow of gas. An appropriate analytical technique is then used to identify at least one of the contaminants collected by the absorptive material 2840.

In preferred embodiments of the methods for passive monitoring of contaminants in a semiconductor processing system of the present invention, the collection device is exposed to a substantially continual supply of gas to be sampled during the step of sampling 2820 and, preferably, during the step of collecting 2830. In various embodiments, the collection device is exposed to a substantially continual flow of gas from the semiconductor processing system such that the collection device samples a fresh sample of the gas. In other embodiments, the collection device is placed inside the semiconductor processing system and exposed to a substantially continual flow of gas through the semiconductor processing system such that the collection device samples a fresh sample of the gas. In one embodiment, the gas flow rate is in the range from about 0.3 liters/min. to about 3 liters/min. In a preferred embodiment, the gas flow rate is greater than about 1 liter/min.

The provision of a fresh sample allows the absorptive material to collect a greater contaminant sample volume in a given time period, for example, by maintaining a contaminant concentration gradient between a sampling volume (for example, a volume of gas in a sample line or volume of gas in a semiconductor processing system) and the volume adjacent the absorptive material of the collection device. It is to be understood that the concentration gradient drives, in part, the rate of first order diffusion of a gas.

In various embodiments, the methods for passive monitoring of contaminants in a semiconductor processing system of the present invention further comprise a step of providing a sample line having a portion adapted to be placed into fluid communication with the semiconductor processing system. In these embodiments, it is preferred that the methods for passive monitoring of contaminants in a semiconductor processing system further comprise a step of conditioning the sample line to equilibrate the internal surface of the sample line, at least in the portion between the semiconductor processing system and the collection device, with the flow of gas. The internal surface of the sampling line is preferably in equilibrium with the gas phase sample in order to not interfere with the contaminant collection process.

For example, it is preferred that the concentration of contaminants of interest on an internal surface of the sample line are such that the internal surface of the sample line does not significantly uptake the contaminants of interest from the flow of gas. A sample line may be equilibrated, for example, by inputting a gas flow until the concentrations of one or more contaminants of interest at the input to the sample line are substantially the same as the concentrations at the output of the sample line. In another example, an approximately twenty foot long sampling line was found to be substantially equilibrated with typical organic contaminants in typical clean room air after approximately 24 hours using a gas flow rate of 1 liter/min. of the clean room air.

In one embodiment, the method samples by diffusion 2820, from a gas flow to a collection device, one or more contaminants in the gas flow; and at least a portion of these sampled contaminants are collected by the absorptive material 2830 of the collection device. Structures, collection devices, and absorptive materials suitable for sampling and collecting in accordance with these embodiments of the present invention include, but are not limited to, those discussed in the context of FIG. 27.

In another embodiment, the method samples by diffusion 2820, from a gas in the semiconductor processing system to an adsorptive material of a collection device, one or more contaminants; and at least a portion of these contaminants are collected by the absorptive material 2830. Collection devices and absorptive materials suitable for sampling and collecting in accordance with these embodiments of the present invention include, but are not limited to, those discussed in the context of FIG. 27. In one embodiment, the collection device has a shape adapted to be placed into a semiconductor wafer carrier. For example, the collection device can comprise a 200–300 mm diameter thick wafer with absorptive material disposed (for example, deposited, or grown) on one or both sides of the wafer. This wafer collection device can then be placed into a semiconductor processing system, together with actual semiconductor wafers or by itself, to provide an in situ monitor of contaminants in the semiconductor processing system. In another embodiment, the collection device or at least a portion of the absorptive material is positioned in the semiconductor processing system through a port in the processing system.

In various embodiments, the step of sampling contaminants 2820 comprises sampling for a sample duration. The sample duration can be chosen, for example, based on required lower detection limit of the procedure. In one embodiment, the sample duration is chosen such that a contaminant with an uptake rate of 1.5 ng per ppm per minute on the absorptive material is detectable, to a selected degree of uncertainty, by the analyzer technique and instrumentation employed in identifying the contaminant. In another embodiment, the sample duration is chose such that a contaminant with an uptake rate in the range from about 1.9 to about 4.2 ng per ppb per minute on the absorptive material is detectable, to a selected degree of uncertainty, by the analyzer technique and instrumentation employed in identifying the contaminant.

In a preferred embodiment, the analyzer comprises a mass spectrometry instrument, which is tuned to transmit only a single narrow mass-to-charge ratio range of interest to increase detection sensitivity and thereby decrease the sample duration required to detect a contaminant of interest to a selected degree of uncertainty. Preferably, the sample duration is in the range from about 5 min to about 50 min for an aromatic contaminant, such as, for example, toluene with an uptake rate of 1.9–4.2 ng/ppb/min and an adsorptive material with a surface area in the range from about 620 cm$^2$ to about 1440 cm$^2$ using a GCMS instrument to identify the toluene contaminant, where the mass spectrometer is tuned to transmit ions with a mass-to-charge ratio in the range from about 91 to about 93. In another embodiment, for example, using a ¼" Tenax® tube and a gas flow rate in the range from about 0.3 liters/min. to about 3 liters/min, the sample duration is in the range from about 2 months to about 4 months.

Preferably, the analyzer uses a detection technology that is inherently sensitive to, and can identify and quantify organic species at very low concentrations, for example, below 1 ppb (V). Suitable approaches for detecting contaminants using a analyzer 2840 include, for example, gas chromatograph/flame ionization detection (GCFID), and combination chromatography-mass spectrometry techniques and instrumentation. The analyzer may include any system that is capable of measuring organic compounds at very low concentrations including, but not limited to a GCFID with, or without a preconcentrator, a gas chromatography-mass spectrometry (GCMS) with, or without a preconcentrator, a photoacoustic detector with, or without a preconcentrator, and TMS with, or without a preconcentrator, or any combination thereof.

Combination chromatography-mass spectrometry techniques and instrumentation include, but are not limited to, gas chromatography-mass spectrometry (GCMS), liquid chromatography-mass spectrometry, and high performance liquid chromatography-mass spectrometry (HPLC-MS). In addition, techniques, such as tuning the mass spectrometry instrument to transmit only a narrow mass-to-charge ratio range of interest, can be used to increase detection sensitivity. For example, for a typical radio-frequency multipole mass spectrometer, the signal-to-noise (SN) for a given charge-to-mass ration is proportional to the square root of the time the mass spectrometer is transmitting that mass-to-charge ratio. As a result, tuning a mass spectrometer to transmit only a narrow mass-to-charge ratio range can improve, in some cases, the SN for that ratio range by two orders of magnitude versus broader scanning of the mass spectrometer.

In a preferred embodiment, analyses of molecular bases and molecular acids samples includes using ion chromatography methods. Contaminants are identified by retention time and quantified using, for example, individual calibration standards and a 10-point calibration procedure. The Low Detection Limit (LDL) of these chromatographic methods is approximately 0.1 ug/m$^3$ per individual component. In a preferred embodiment, molecular bases and refractory material samples are analyzed using a gas chromatograph (GC) equipped with a mass selective detector (such as, for example, a mass spectrometer) and Thermal Desorption System (TD). The total analytical system (TD/GC/MS) is optimized to separate and quantify analytes with a boiling temperature of hexane and higher with LDL of approximately 0.1 ug/m$^3$ per individual component. Individual components, and thereby contaminants, are identified by a mass spectrometry library search and chromatographic peak position. In one embodiment, contaminant concentrations are quantified against two analytical standards, for example, toluene and hexadecane.

It is to be understood that techniques and instrumentation can be chosen based on the semiconductor processing system and process to which the methods of the present invention are applied. For example, in one embodiment of passive monitoring of contaminants in a filter or filter system, the step of identifying targets a low boiling point contaminant propagated through the filter. This targeted contaminant can serve, for example, as a leading indicator gas. In these embodiments, the analyzer techniques and instrumentation need only be capable of identifying the target contaminant.

In other embodements, identification of a range of contaminant masses is desired. For example, in monitoring first, second, third, and fourth order contamination effects in a photolithography tool, the target contaminants can comprise high molecular weight refractory organics and compounds including carbon atoms within the range of approximately one to thirty carbon atoms $C_1$–$C_{30}$. The first order contaminants may comprise high molecular weight refractory organics such as, for example, $C_6$ siloxanes and $C_6$ iodide with an inorganic component which is not volatilized through combination with oxygen. Second order contaminants may comprise high molecular weight organics, such as, for example, compounds including carbon atoms within the range of approximately six to thirty carbon atoms ($C_6$–$C_{30}$). Third order effects can arise due to the contaminating effects of organics such as $C_3$–$C_6$ that have approximately three to six carbon atoms. Fourth order contaminants include organics such as, for example, methane, that have approximately one to five carbon atoms.

In other embodiments, target contaminants can comprise only first and second order contaminants because first and second order contaminating effects have a greater impact on the contamination of optical systems than third or fourth order contaminants. In these embodiments, the analyzer techniques and instrumentation need only be capable of identifying these target contaminants.

Referring again to FIG. 28, in various embodiments, the methods for passive monitoring of contaminants in a semiconductor processing system of the present invention further comprise a step of evaluating the condition of a filter 2850 of the semiconductor processing system based at least in part on one or more contaminants identified by the analyzer. The filter may be a single filter, multiple filters or a filter system. In one embodiment, the step of evaluating evaluates the condition of a filter based on the concentration of a low boiling point target contaminant propagated through the filter. This targeted contaminant can serve, for example, as a leading indicator gas. Preferably, the targeted contaminant travels faster in the filter than other target contaminants. These methods including a step of evaluating preferably establish a correlation between one or more low molecular weight compounds and one or more high molecular weight compounds to determine the condition of the filter with respect to a one or more contaminants of interest.

Further, the methods for passive monitoring of contaminants in a semiconductor processing system including a step of evaluating the condition of a filter preferably include sampling a gas flow at a multiple locations, such as, for example, upstream, downstream and inside of the filter.

In one embodiment, the methods for passive monitoring of contaminants in a semiconductor processing system of the present invention further comprise a step of measuring at least one of temperature, pressure or flow rate of a gas flow 2860. In another embodiment, the methods for passive monitoring of contaminants in a semiconductor processing system of the present invention further comprise a step of monitoring at least one of temperature and pressure of a gas in the semiconductor processing system 2860. These measurements can be used to provide increased accuracy in the quantitative determination of one or more contaminant concentrations in the semiconductor processing system. For example, an average contaminant concentration in a semiconductor processing system can be determined from a contaminant concentration determined in the identifying step using the gas flow rate, temperature and pressure, assuming a sufficiently equilibrated sampling line. In addition, the temperature, pressure and flow rate measurements can be used in embodiments comprising a step of evaluating the condition of a filter to evaluate the condition of a filter or filter system.

Structures and monitor systems suitable for the step of measuring include, but are not limited to, those discussed in the context of FIG. 27. Preferably, the step of measuring 2860 measures the temperature, pressure, and flow rate in a region adjacent the proximal end of the collection device. In one embodiment, the step of measuring 2860 measures the temperature, pressure and flow rate in a region adjacent to a flow regulator, inside the flow regulator, or both.

In one embodiment, the methods for passive monitoring of contaminants in a semiconductor processing system of the present invention further comprise a step of regulating at least one of temperature, pressure or flow rate of a gas flow 2870. In another embodiment, the methods for passive monitoring of contaminants in a semiconductor processing system of the present invention further comprise a step of regulating at least one of temperature, pressure of a gas in the semiconductor processing system 2870. In various embodiments, the step of regulating regulates temperature, pressure, or both, based at least in part on measurements provided by a monitoring system.

The step of regulating can be used to provide increased accuracy in the quantitative determination of one or more contaminant concentrations in the semiconductor processing system. Structures and regulator systems suitable for the step of regulating include, but are not limited to, those discussed in the context of FIG. 27. Preferably, the step of regulating 2860 regulates the temperature, the pressure, or both, of the flow of gas at least in a region adjacent the proximal end of a collection device. In one embodiment, the step of regulating 2860 regulates the temperature and pressure of a region adjacent to a flow regulator, inside the flow regulator, or both.

In another aspect, the present invention provides systems and methods for detecting airstream backflow in a semiconductor processing system using a differential pressure monitor.

In semiconductor processing, the direction of airstream flow can be critical to controlling system contamination. One area of particular concern is the backflow of an airstream from the track into the stepper. Typically, the airstream flows from the stepper to the track. In certain situations, however, this airstream may be misdirected causing air to backflow into the stepper. Such misdirection can occur, for example, when a processing tool is stopped, a processing tool door is opened, or a system air filter fails.

Misdirected airstream flow can have serious consequences. For example, during backflow -contaminants in the track can be forced into the stepper and potentially onto to the optics of the photolithography tools connected to the stepper.

In one aspect, the present invention provides a system for detecting airstream backflow using a differential pressure monitor. In preferred embodiments, the present invention provides a system for detecting backflow from the track into the stepper. Referring to FIG. 29A, the system detects backflow in a semiconductor processing system comprising an airstream source 2901 (such as, for example, a track) and a delivery region 2903 (such as, for example, a stepper). The system comprises a differential pressure monitor 2905 comprising a first pressure measurement device 2907 positioned at the airstream source 2901, and a second pressure measurement device 2909 positioned at the delivery region 2903. In desired operation of the semiconductor processing system, the pressure, $P_1$, in the source airstream 2901 is greater than in the pressure, $P_2$, in the delivery region 2903; and the airstream 2911 flows from the source 2901 to the delivery region 2903. This situation is illustrated in FIG. 29A.

The differential pressure monitor 2905 monitors the difference in pressure between the pressure, $P_1$, in the source airstream 2901 and the pressure, $P_2$, in the delivery region 2903. When $P_1$ is greater than $P_2$, the differential pressure monitor 2905 provides, for example, no signal, or a signal indicating normal airflow.

When the pressure, $P_2$, in the delivery region 2903 is greater than the pressure, $P_1$, in the source airstream 2901, conditions may exist for airstream backflow 2915. This situation is illustrated in FIG. 29B. When the differential pressure monitor 2905 detects that $P_2$ is greater than $P_1$, the differential pressure monitor 2905 provides a warning signal indicating potential backflow in the semiconductor processing system.

Figure 30A:
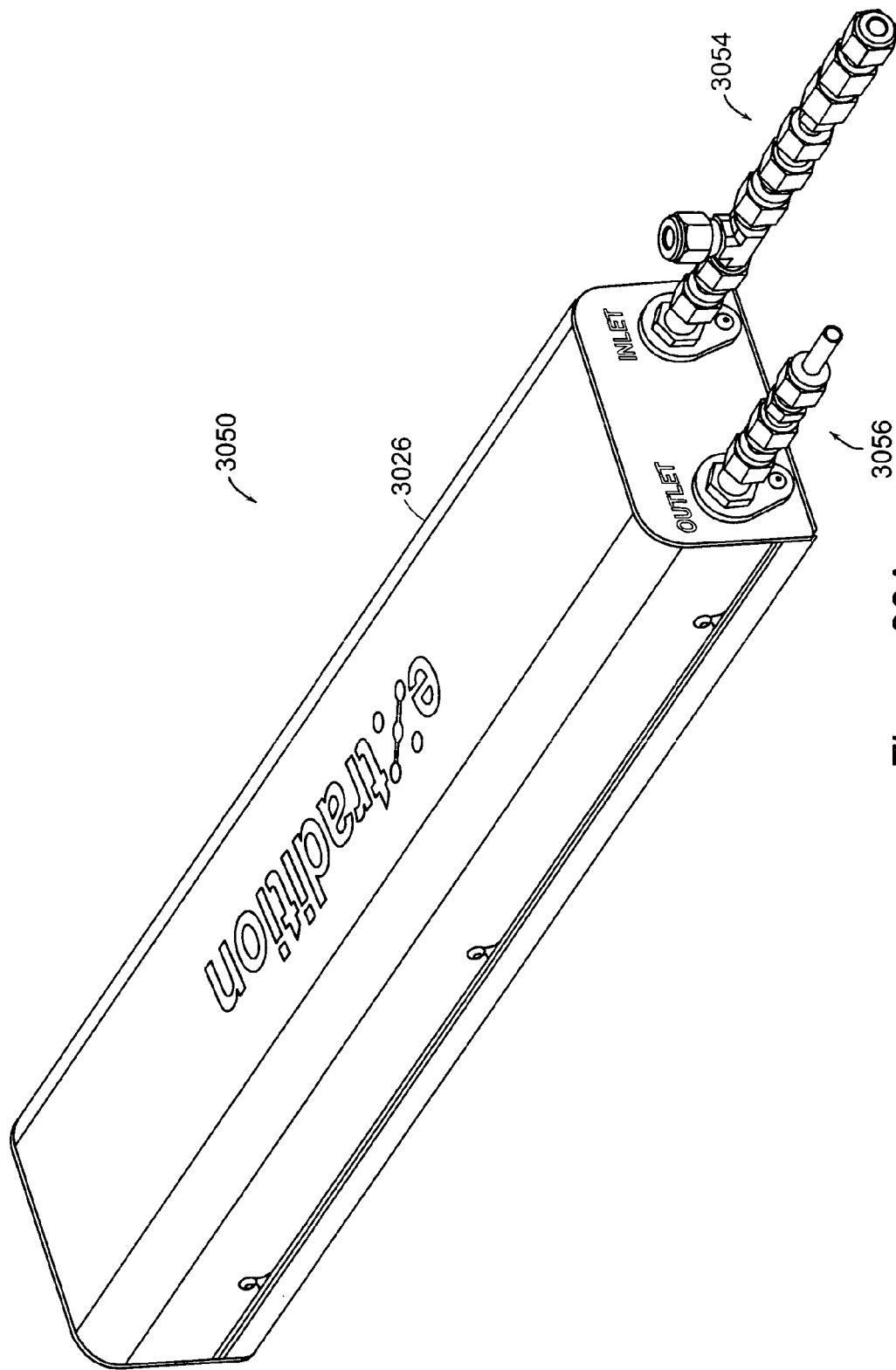
FIGS. 30A–30E illustrate schematic diagrams of a device that functions as a concentrator in a filter system in accordance with a preferred embodiment of the present invention.
Figure 30B:
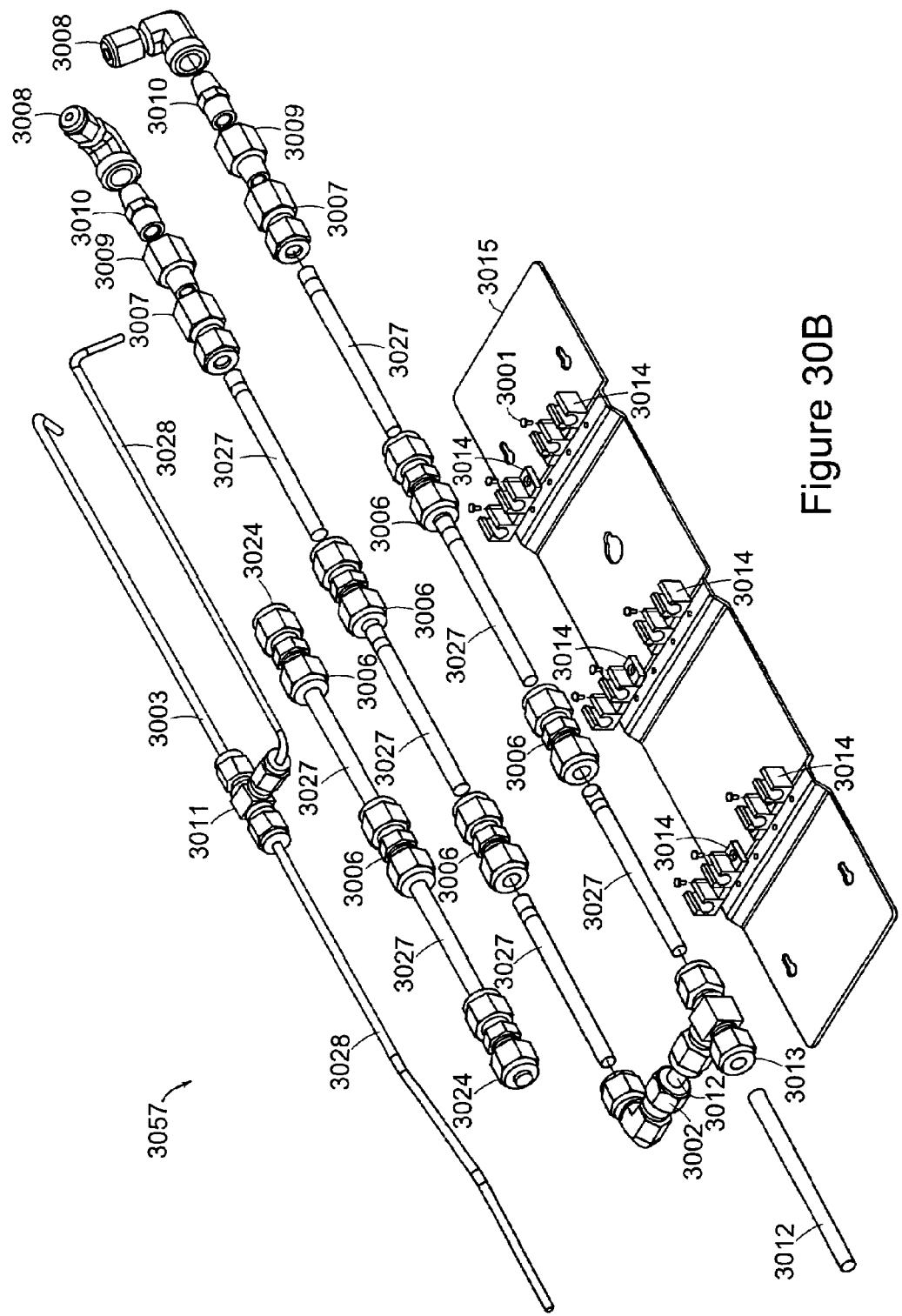
Figure 30C:
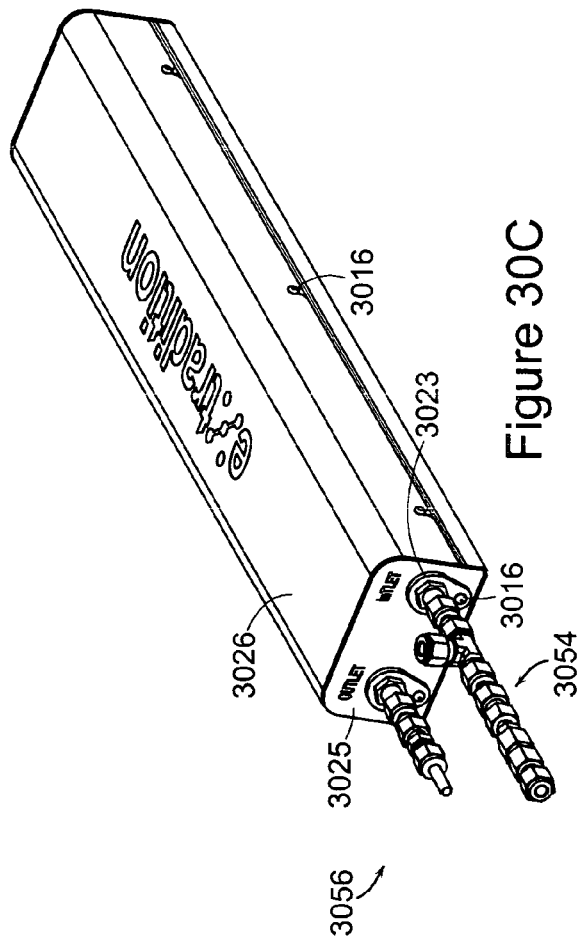
Figure 30D:
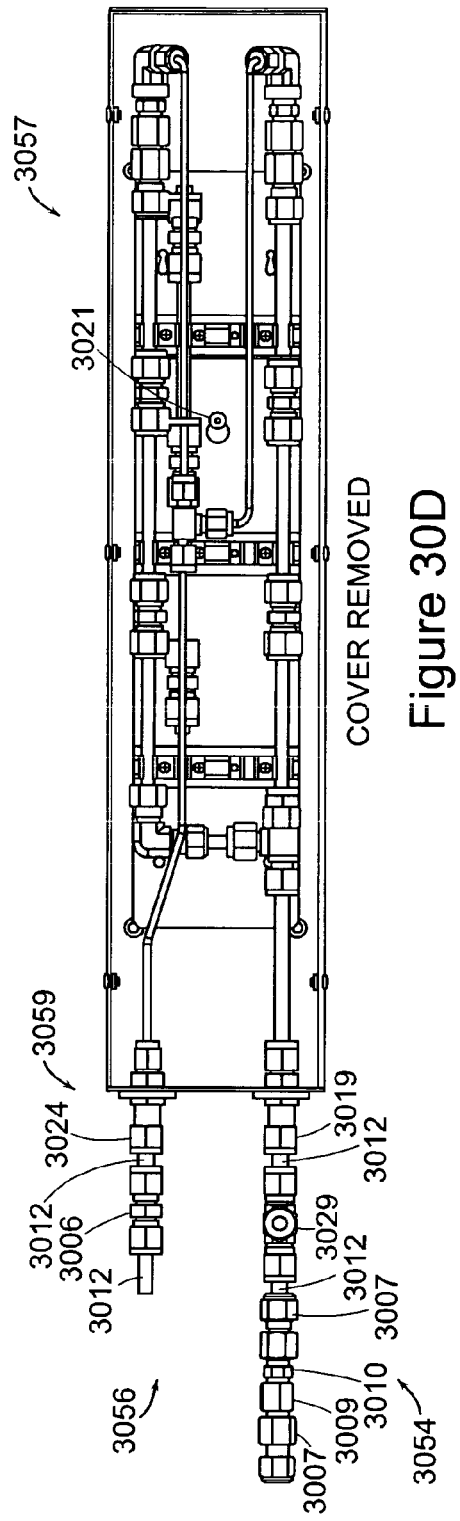
Figure 30E:
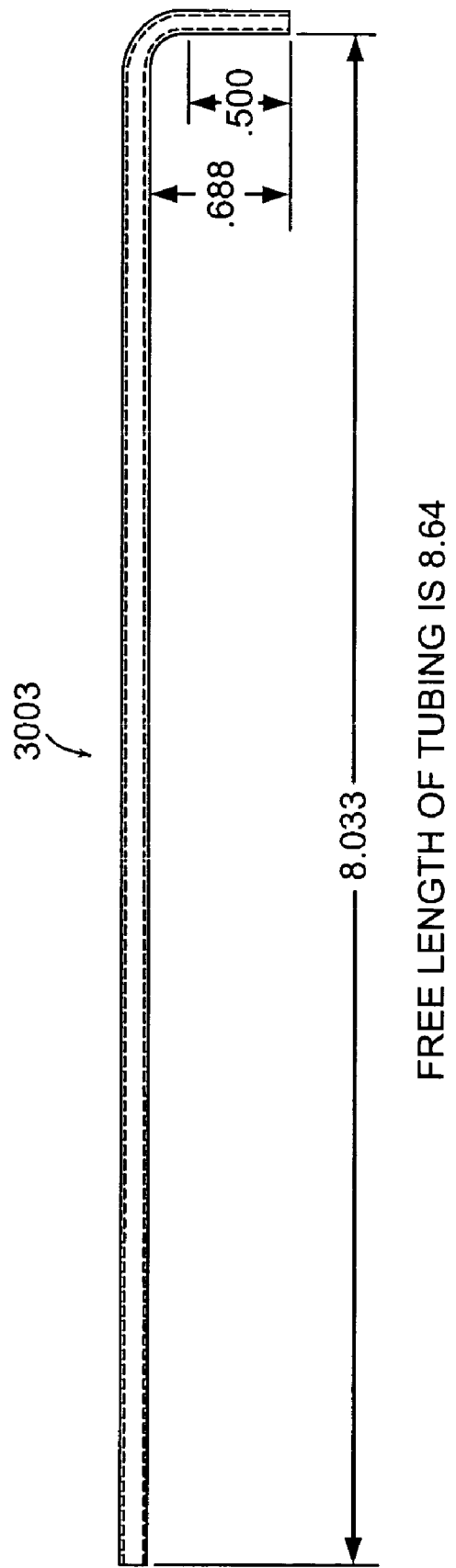
Figure 31A:
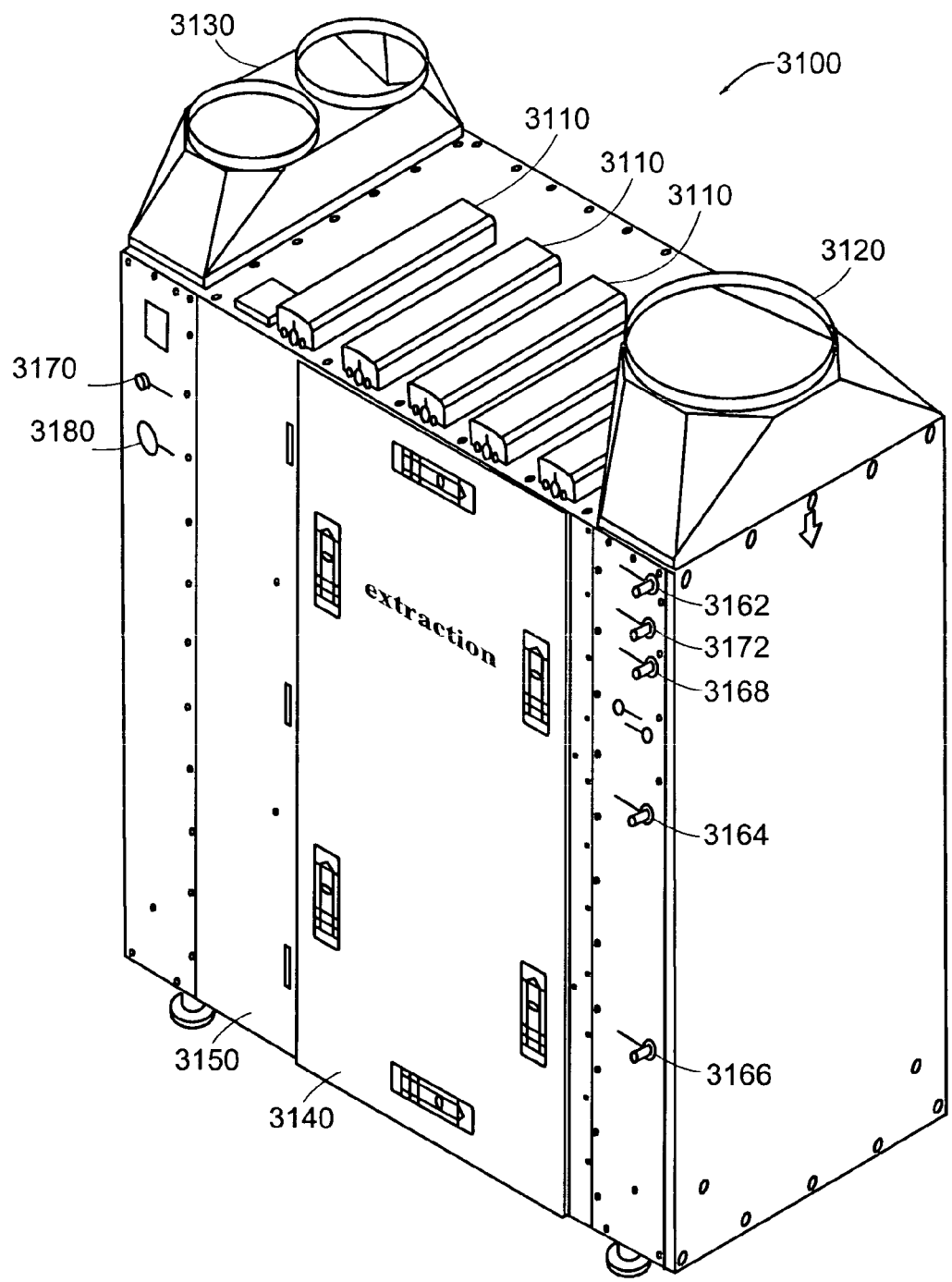
FIGS. 31A–31E illustrate a schematic diagram of a system using a device for monitoring contaminants and performance of a filter system in accordance with a various embodiments of the present invention.
Figure 31B:
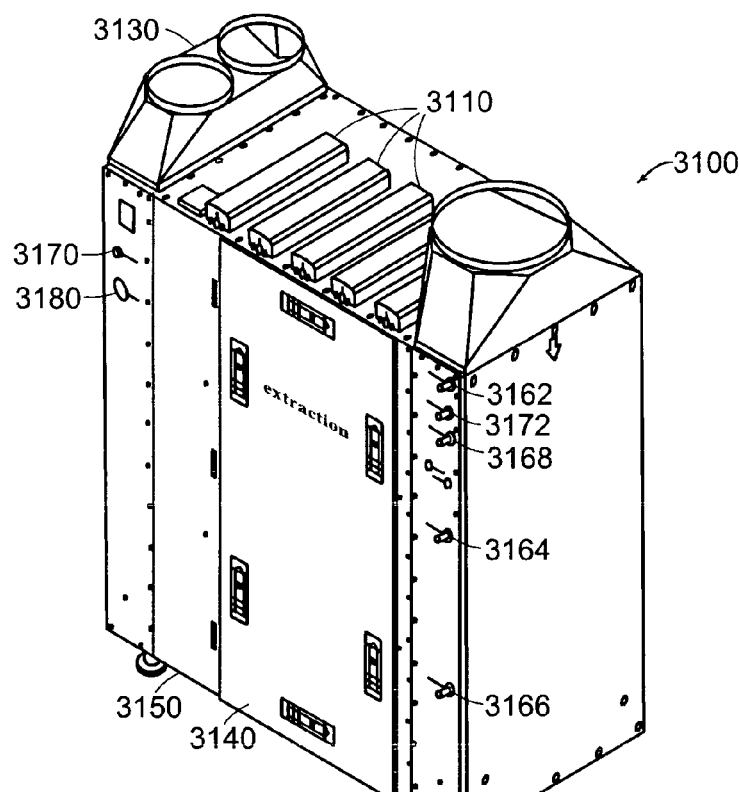
Figure 31E:
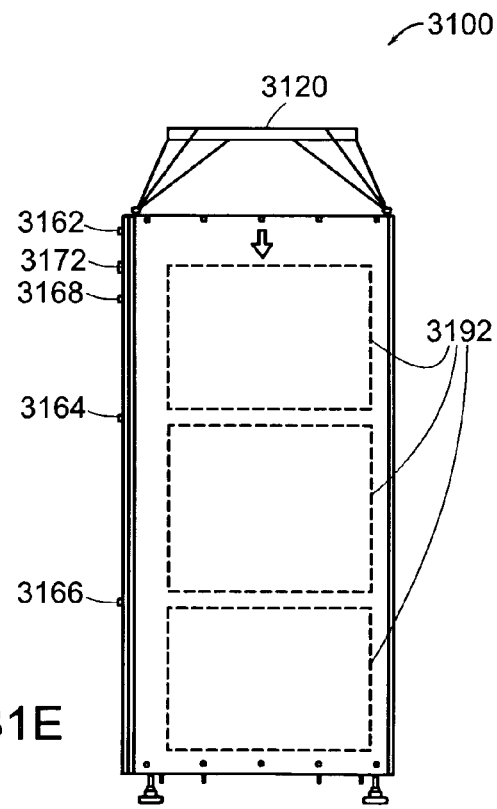
Figure 31C:
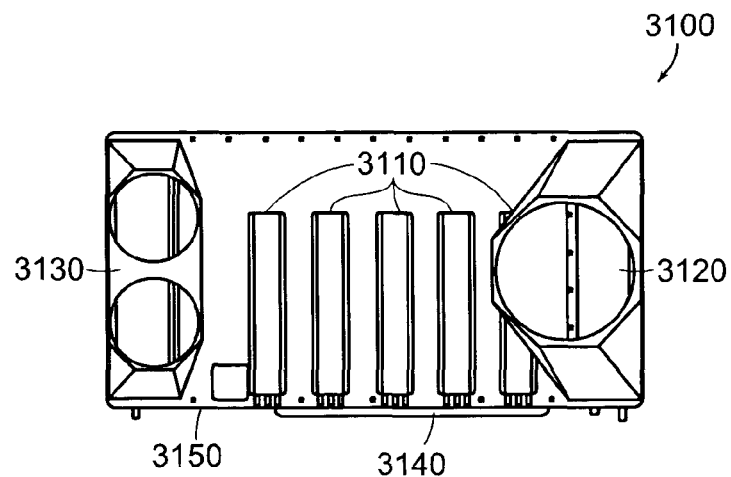
Figure 31D:
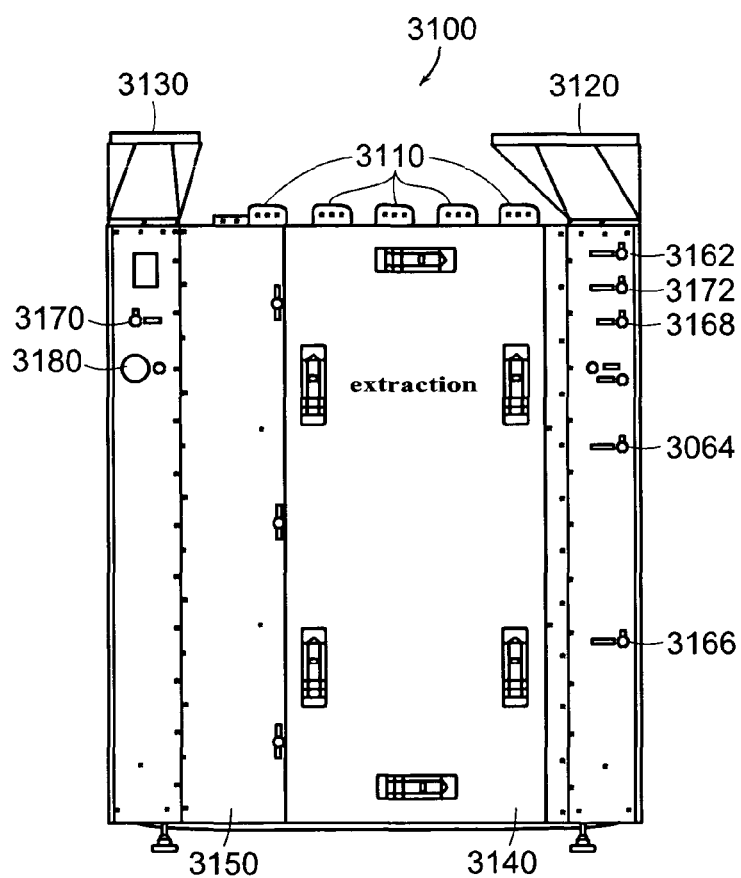

FIGS. 30A–30E illustrate schematic diagrams of another embodiment of a device that can function as a concentrator in a contaminant and filter monitoring system in accordance with a preferred embodiment of the present invention. FIG. 30A is an illustration of one embodiment of the concentrator device 3050, with a cover 3026 in place, and showing one embodiment of an inlet interface 3054 and an outlet interface 3056. FIG. 30B is an exploded assembly drawing of a concentrator 3057, FIG. 30C is an assembly drawing of a concentrator device 3050, and FIG. 30D is an assembly drawing of the concentrator 3057 inserted into a manifold 3059 having an inlet interface 3054 and an outlet interface 3056 where, in one embodiment, the components and mounting hardware of FIGS. 30B–30D are as follows:

4–40×¼" Phillips Head Screw 3001;
¼" Comp. Teflon Elbow Union 002;
⅛" SS Tubing 3003 (FIG. 30E is a scale drawing of one embodiment of a ⅛" SS Tubing 3003);
¼"×¼" Straight Teflon Union 3006;
¼" FPT –¼" Comp. Stainless Steel (SS) Adapter 3007;
⅛" FPT ×⅛" Comp. SS Elbow 3008;
25 Micron Particle Filter 3009;
⅛" NPT Male 2E Orifice 3010;
⅛" SS Comp. Tee 3011;
¼" Teflon Tubing 3012;
¼" Teflon Comp. Tee 3013;
Rubber Multi-Tube Holder 3014;
Refractory Trap Tube Holder Plate 3015;
6–32×¼" Phillips Screws 3016;
¼"×⅛" SS Bulkhead Union 3019;
6–32×¼" Button Head Screw 3021;
Locking Plate for Bulkhead 3023;
¼"×¼" SS Bulkhead Union 3024;
Bulkhead 3025;
Cover 3026;
¼"×3½" Tenax Tube containing about 150 mg of adsorptive material 3027;
⅛" Teflon Tubing 3028; and
¼" SS Comp. Tee 3029.

The filter system including a filter monitoring functionality can be reduced in size using a device such as, for example, the concentrator 3057. A greater volume of contaminants can be collected in the filter system over an interval of time if the temperature is reduced to, for example, 0° C. or lower. Using a concentrator device that includes absorptive materials such as, for example, Tenax® T.A, in a collection device 3027 can also increase the volume of material collected. High boilers (compounds with boiling points greater than about 150° C.), such as, for example, organics having or more six carbon atoms are generally absorbed by Tenax® T.A. Preferably, the total mass of adsorptive materials, such as, for example, Tenax® T.A. is greater than about 0.05 grams (g). In another embodiment, the total mass of adsorptive material is in the range from about 0.05 g to about 1 g.

In another embodiment, absorptive materials for use in the collection device 3027 include, for example, carbon traps such as supplied by, for example, Supelco can be used in embodiments including low boilers. Other embodiments include a combination of the collection devices 3027 for high and low boilers, which can be arranged in parallel and/or in series. In addition, the collection device 3027 can be a single device instead of multiple devices arranged in parallel and/or series.

In preferred embodiments, the concentrator 3057 includes two series of collection devices 3027 in parallel. A series of collection devices enables one to better resolve differences in contaminant uptake along a length of adsorption material because the collection device corresponding to a given location along the length of adsorptive material can be analyzed separately from the others. In comparison, such resolution is lost when a single collection device, of equal length to the series, is used because length dependence information is lost due to contaminants desorbing from the single collection device independent of their position along the length of adsorptive material.

Having two substantially identical series of collection devices in parallel is preferred because the redundancy inherent in this configuration increases the reliability of the contaminant analysis by providing a measure of the variation in collection properties between collection devices and provide a measure of variance for the data. An example of one preferred embodiment of two substantially identical series of collection devices 3027 in parallel is illustrated in FIGS. 303B and 30D.

FIGS. 31A–31E illustrate a schematic diagram of a system for monitoring contaminants and the performance of a filter system in accordance with a various embodiments of the present invention. In various embodiments, the system 3100 includes a plurality of concentrator devices 3110 (such as, for example, illustrated in FIGS. 25A–25C and/ or 30A–30E) for monitoring contaminants and the performance of a filter system. The filter system includes an inlet interface 3120, a filter module 3140 having a plurality of filters 3192 (schematically illustrated in FIG. 31E), a HEPA filter module 3150 having a HEPA filter, an output interface 3130, and a compressed air inlet 3172 for actuation of system pneumatics. The outlet interface 3130 can also, in other embodiments, be coupled to a vacuum system if evacuation of the system for determining contamination is required. The inlet and outlet interfaces preferably have sealed surfaces for environmental isolation.

The system 3100 includes interstack sampling ports 3162, 3164, 3166 for sampling the gas stream between filters 3192 or after the filters 3192. The system also includes an inlet sample port 3168 for sampling the input gas stream prior to filtration and an outlet sample port 3170 for sampling the gas stream after the HEPA filter module 3150 but prior to return through the output interface 3130. Preferably, the system also includes a pressure regulation device proximate to the inlet interface 3120 and a pressure gauge 3180 to measure pressure in the system.

In one embodiment, the filter module 3140 includes an adequate valving arrangement to allow accurate sampling of the various sampling ports 3162, 3164, 3166, 3168, 3170 by the concentrator devices 3110. A single concentrator device 3110 or multiple concentrator devices 3110 can be used to monitor the output of a sampling port and collect a sample for post-collection analysis. For example, in one embodiment, one concentrator device 3110 is connected to each of the five sampling ports. In another embodiment, multiple concentrator devices 3110 can be connected to a single sampling port, for example, where contamination concentration is anticipated to be low, such as at the outlet sampling port 3170.

The system can further include a controller/processor, such as a proportional integral controller and a control module, A preferred embodiment includes electronically controlled valves to impose a duty cycle for sampling per concentrator device. The duty cycle can be programmable. The electronically controlled valves can assist in embodiments having high concentrations of impurities as they can address the potential of overload. Preferably, the controlled valves are pneumatically actuated with compressed clean dry air.

The post-collection analysis of the material collected by a concentrator device can provide quantitative and qualitative measures of the contamination present in a gas stream in the semiconductor processing environment. Analysis tools such as, for example, GCMS or GCFID can be used to detect the contaminants. It may also provide for monitoring of the performance of the filter system.

In some embodiments the concentrator devices can be cooled using a thermoelectric cooling device. Organics can be more readily condensed and collected using the low temperature embodiment. A fewer number of traps are required for the low temperature embodiment since the organics can be collected post condensation. An embodiment of the low temperature system can further include heat sinks to dissipate the heat energy generated.

The claims should not be read as limited to the described order or elements unless stated to that effect. Therefore, all embodiments that come within the scope and spirit of the following claims and equivalents thereto are claimed as the invention.

What is claimed is:

1. A system for determining and monitoring contamination in a photolithography instrument, comprising at least one collection device in fluid communication with a gas flow extending through an optical system of the photolithography instrument, the collection device having an adsorptive material and a saturation capacity for a lower molecular weight contaminant, the collection device being operated past the saturation capacity of the lower molecular weight contaminant while continuing to adsorb higher molecular weight contaminants in the gas flow.

2. The system of claim 1, wherein the adsorptive material comprises glass spheres having predetermined surface properties for adsorption of contaminants.

3. The system of claim 1, wherein the collection device is tubular.

4. The system of claim 1, further comprising a collection device that is not in fluid communication with the gas flow.

5. The system of claim 1, wherein the collection device is at least one of glass and coated glass material.

6. The system of claim 1, wherein the adsorptive material comprises the polymer Tenax®.

7. The system of claim 1, wherein the contamination includes at least one of refractory compounds, high molecular weight compounds and low molecule weight compounds.

8. A contamination analysis apparatus in a photolithography system having an optical element comprising:

a collection device comprising a first material having a surface property of the optical element coupled to a gas flow, the collection device being coupled to a light source such that light is optically coupled to a surface of the material and having an adsorptive material with a saturation capacity to adsorb contaminants in the gas flow.

9. The contamination analysis apparatus of claim 8, wherein the adsorptive material comprises a polymer that absorbs higher molecular weight organic compounds.

10. The contamination analysis apparatus of claim 8, wherein the adsorptive material comprises glass spheres.

11. The contamination analysis apparatus of claim 8, wherein the contaminants include at least one of refractory compounds, high molecular weight compounds and low molecular weight compounds.

12. A filtering system for removing contamination in a semiconductor processing system, comprising at least one collection device in fluid communication with a gas flow extending through an optical system of the semiconductor processing system, at least one collection device having a selectively permeable membrane that filters contaminants including a refractory compound, a high molecular weight compound and a low molecular weight compound from the gas flow, the collection device being operated past a saturation of the membrane to absorb the low molecular weight compound.

13. The filtering system of claim 12, wherein the collection device is coupled to a vacuum source to increase a pressure gradient across the selective membrane.

14. The filtering system of claim 12, wherein the gas flow comprises clean dry air, nitrogen, and/or other inert gases.

15. The filtering system of claim 12, further comprising a regenerative adsorption device in fluid communication with an output permeate stream from the selectively permeable membrane.

16. The filtering system of claim 12, further comprising a second collection device in fluid communication with a residue stream of the collection device, the second collection device having a second membrane that is selectively permeable to oxygen and water.

* * * * *